(12) United States Patent
Borrebaeck et al.

(10) Patent No.: US 10,859,572 B2
(45) Date of Patent: Dec. 8, 2020

(54) BIOMARKER SIGNATURES AND USES THEREOF

(71) Applicant: Immunovia AB, Lund (SE)

(72) Inventors: Carl Arne Krister Borrebaeck, Lund (SE); Lars Bertil Christer Wingren, Södra Sandby (SE)

(73) Assignee: Immunovia AB, Lund (SE)

( * ) Notice: Subject to any disclaimer, the term of this patent is extended or adjusted under 35 U.S.C. 154(b) by 0 days.

(21) Appl. No.: 15/990,335

(22) Filed: May 25, 2018

(65) Prior Publication Data

US 2019/0219573 A1    Jul. 18, 2019

Related U.S. Application Data

(63) Continuation of application No. 13/820,981, filed as application No. PCT/GB2011/051673 on Sep. 7, 2011, now abandoned.

(30) Foreign Application Priority Data

Sep. 7, 2010  (GB) ................................... 1014837.7

(51) Int. Cl.
*G01N 33/564* (2006.01)
*G01N 33/68* (2006.01)
*A61K 38/00* (2006.01)
*B82Y 30/00* (2011.01)

(52) U.S. Cl.
CPC ............ *G01N 33/564* (2013.01); *B82Y 30/00* (2013.01); *G01N 33/6893* (2013.01); *G01N 2800/104* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David | |
| 4,486,530 A | 12/1984 | David | |
| 5,856,090 A | 1/1999 | Epstein | |
| 2006/0177814 A1 | 8/2006 | Behrens | |
| 2013/0288912 A1 | 10/2013 | Borrebaeck | |

FOREIGN PATENT DOCUMENTS

| WO | WO 1998/037186 | 8/1998 |
|---|---|---|
| WO | WO 02/26831 | 4/2002 |
| WO | WO 2009/068857 | 6/2009 |
| WO | WO 2012/032345 | 3/2012 |
| WO | WO 2015/038069 | 3/2015 |
| WO | WO 2015/067969 | 5/2015 |
| WO | WO 2015/189591 | 12/2015 |
| WO | WO 2017/211893 | 12/2017 |
| WO | WO 2017/211896 | 12/2017 |

OTHER PUBLICATIONS

Carlsson et al., Serum protein profiling of systemic lupus erythematosus and systemic sclerosis using recombinant antibody microarrays, 2011, Mol. Cell Proteomics, 10(5).
Gladman et al., Systemic lupus erythematosus disease activity index 2000, 2002, J. Rheumatol., 29(2):288-91.
Jason W. Bauer et al., Elevated serum levels of interferon-regulated chemokines are biomakers for active human systemic lupus erythematosus. PLoS Medicine, Dec. 2006, vol. 3, Issue 12, pp. 2274-2284.
Jason W. Bauer et al., Interferon-regulated chemokines as biomarkers of systemic lupus erythematosus disease activity. A Validation Study. Arthritis & Rheumatism, vol. 60, No. 10, Oct. 2009, pp. 3098-3107.
Anders Carlsson et al., Serum proteome profiling of metastatic breast cancer using recombinant antibody microarrays. European Journal of Cancer 44 (2008) pp. 472-480.
L. Pala et al., Pathophysiology—Relationship between GLP-1 levels and dipeptidyl peptidase-4 activity in different glucose tolerance conditions. Diabetic Medicine, 27 (2010) pp. 691-695.
Brad H. Rovin, Biomarker discovery in human SLE nephritis. Bulletin of the NYU Hospital for Joint Disease (2007); 65(3): pp. 187-193.
Brad H. Rovin et al., Biomarkers for lupus nephritis: the quest continues. Clin J Am Nephrol 4: (2009) pp. 1858-1865.
Bardera et al., Update on screening methodologies. Future Med. Chem. (2009) 1(2) pp. 253-256.
P.J. Utz, Multiplexed assays for identification of biomarkers and surrogate markers in systemic lupus erythematosus.www.lupus.journal.com, pp. 204-311.
Neifred Villegas-Zambrano et al., Correlation between clinical activity and serological markers in a wide cohort of patients with systemic lupus erythematosus. Contemporary Challenges in Autoimmunity: Ann. N.Y. Acad. Sci. 1173: pp. 60-66 (2009).
Ingvarsson et al., Journal of Proteome Research, 2007, vol. 6, pp. 3527-3536.
Wingren et al., Identification of serum biomarker associated with pancreatic center, Cancer Res., 72(10), pp. 2481-2490, 2012.
Data sheet for Affymetrix U95A GeneChip.
Abraham, D. J., Krieg, T., Distler, J., and Distler, 0. (2009) Overview of pathogenesis of systemic sclerosis, Rheumatology (Oxf.) 48 Suppl 3, iii3-7.
Ahearn JM LC, Kao AH, Manzi S. Biomarkers for systemic lupus erythematosus. Transl Res 2012 159(4):326-42.

(Continued)

*Primary Examiner* — Gary B Nickol
*Assistant Examiner* — Jegatheesan Seharaseyon
(74) *Attorney, Agent, or Firm* — Knobbe Martens Olson & Bear LLP

(57) ABSTRACT

The invention provides a method for determining a Systemic Lupus Erythematosus-associated disease state in a subject comprising the steps of (a) providing a sample to be tested; and (b) measuring the presence and/or amount in the test sample of one or more biomarker(s) selected from the group defined in Table 1, wherein the presence and/or amount in the test sample of the one or more biomarker(s) selected from the group defined in Table 1 is indicative of a Systemic Lupus. The invention also provides an array and a kit suitable for use in the methods of the invention.

9 Claims, 33 Drawing Sheets

(56) References Cited

OTHER PUBLICATIONS

Asherson, "Catastrophic antiphospholipid syndrome: international consensus statement on classification criteria and treatment guidelines", Lupus, (2003), vol. 12, No. 7, pp. 530-534.
Atamas, S. P., and White, B. (2003) Cytokine regulation of pulmonary fibrosis in scleroderma, Cytokine Growth Factor Rev. 14, 537-550.
Beirne, P., Pantelidis, P., Charles, P., Wells, A. U., Abraham, D. J., Denton, C. P., Welsh, K. I., Shah, P. L., du Bois, R. M., and Kelleher, P. (2009) Multiplex immune serum biomarker profiling in sarcoidosis and systemic sclerosis, Eur. Respir. J. 34, 1376-1382.
Better, Science, (1988), vol. 240, p. 1041.
Bird et al., Science, (1988), vol. 242, p. 423.
Bombardier et al., Arthritis Rheum., (1992), vol. 35, No. 6, pp. 630-640.
Borrebaeck CK, Wingren C. Recombinant Antibodies for the Generation of Antibody Arrays. In: Korf U, editor. Protein Microarrays. Methods in Molecular Biology. 785: Humana Press; 2011. p. 247-62.
Borrebaeck, C. A. K., and Wingren, C. (2009) Design of high-density antibody microarrays for disease proteomics: Key technological issues, J. Proteomics 72, 928-935.
Borrebaeck, C.A. and C. Wingren, High-throughput proteomics using antibody microarrays: an update. Expert Rev Mol Diagn, 2007. 7(5):673-86.
Borrebaeck, Carl A K and Wingren, Christer. Transferring proteomic discoverys into clinical practice. Expert rev. proteomics. 2009, vol. 6(1), pp. 11-13.
Brito TN, Vilar MJ, Almeida JB, et al. Measuring eosinophiluria, urinary eosinophil cationic protein and urinary interleukin-5 in patients with Lupus Nephritis. Allergy Asthma Clin Immunol 2014; 10: 61.
Capper ER, Maskill JK, Gordon C, Blakemore AI. Interleukin (IL)-10, IL-1ra and IL-12 profiles in active and quiescent systemic lupus erythematosus: could longitudinal studies reveal patient subgroups of differing pathology? Clin Exp Immunol 2004; 138: 348-56.
Carlsson A PO, Ingvarsson J, Widegren B, Salford L, Borrebaeck CA, Wingren C. Plasma proteome profiling reveals biomarker patterns associated with prognosis and therapy selection in glioblastoma multiforme patients. Proteomics Clin Appl. 2010 4(6-7): 591-602.
Carlsson A WC, Kristensson M, Rose C, Ferne M, Olsson H, Jernstrom H, Ek S, Gustavsson E, Ingvar C, Ohlsson M, Peterson C, Borrebaeck CA. Molecular serum portraits in patients with primary breast cancer predict the development of distant metastases. Proc Natl Acad Sci U S A. 2011 108(34): 14252-7.
Chen, C. H. (2008) Review of a current role of mass spectrometry for proteome research, Anal. Chim. Acta 624, 16-36.
Chew C, Pemberton PW, Husain AA, Haque S, Bruce IN. Serum cystatin C is independently associated with renal impairment and high sensitivity C-reactive protein in systemic lupus erythematosus. Clin Exp Rheumatol 2013; 31: 251-5.
Chih-chung, C., and Chih-Jen, L. (2007) LIBSVM: a library for support vector machines., http/::www.csie.ntu.edu.tw/cjlin/libsvm.
Choe JY, Kim SK. Serum TWEAK as a biomarker for disease activity of systemic lupus erythematosus. Inflamm Res 2016; 65: 479-88.
Chothia and Lesk, 1987 'Canonical structures for the hypervariable regions of immunoglobulins' J. Mal. Biol., 196: 901-917.
Chothia et al., 1989 'Conformations of immunoglobulin hypervariable regions' Nature, 342:877-883.
Clackson et al., Nature, (1991), vol. 352, pp. 624-628.
Cockwell, Paul and Adu, Dwomoa. Glomerulonephritis. Encyclopedia of life sciences. 2001, pp. 1-12.
Cook, R.J., et al., Prediction of short term mortality in systemic lupus erythematosus with time dependent measures of disease activity. J Rheumatol, 2000. 27(8):1892-5.
Cordeiro, Ana C and Isenberg, David A. Novel therapies in lupus—focus on nephritis. Acto reumatol port. 2008, vol. 33, pp. 157-169.
Cravatt, B. F., Simon, G. M., and Yates, J. R., 3rd. (2007) The biological impact of mass-spectrometry-based proteomics, Nature 450, 991-1000.
Daugherty et al., Protein Eng, (1998), vol. 11, No. 9, pp. 825-832.
Daugherty et al., Protein Eng, (1999), vol. 12, No. 7, pp. 613-621.
D'Cruz DP KM, Hughes GR. Systemic lupus erythematosus. Lancet. 2007 369(9561):587-96.
De Sanctis JB, Garmendia JV, Chaurio R, Zabaleta M, Rivas L. Total and biologically active CD154 in patients with SLE. Autoimmunity 2009; 42: 263-5.
Dexlin-Mellby L SA, Centlow M, Nygren S, Hansson SR, Borrebaeck CA, Wingren C. Tissue proteome profiling of preeclamptic placenta using recombinant antibody microarrays. Proteomics Clin Appl. 2010 4(10-11):794-807.
Doran, J. P., and Veale, D. J. (2008) Biomarkers in systemic sclerosis, Rheumatology (Oxf.) 47 Suppl 5, v36-38.
Duan, H., Fleming, J., Pritchard, D. K., Amon, L. M., Xue, J., Arnett, H. A., Chen, G., Breen, P., Buckner, J. H., Molitor, J. A., Elkan, K. B., and Schwartz, S. M. (2008) Combined analysis of monocyte and lymphocyte messenger RNA expression with serum protein profiles in patients with scleroderma, Arthritis Rheum. 58, 1465-1474.
Edworthy, "Analysis of the 1982 ARA lupus criteria data set by recursive partitioning methodology: new insights into the relative merit of individual criteria", J. Rheumatol., (1988), vol. 15, No. 10, pp. 1493-1498.
Eisen, M. B., Spellman, P. T., Brown, P. 0., and Botstein, D. (1998) Cluster analysis and display of genome-wide expression patterns, Proc. Natl. Acad. Sci. U.S.A. 95, 14863-14868.
Eisenberg R. Why can't we find a new treatment for SLE? J Autoimmun 2009; 32: 223-30.
Ellmark, P., Ingvarsson, J., Carlsson, A., Lundin, B. S., Wingren, C., and Borrebaeck, C. A. K. (2006) Identification of protein expression signatures associated with Helicobacter pylori infection and gastric adenocarcinoma using recombinant antibody microarrays, Mal. Cell. Proteomics 5, 1638-1646.
Fattal I, Shental N, Mevorach D, et al. An antibody profile of systemic lupus erythematosus detected by antigen microarray. Immunology 2010; 130: 337-43.
Fraker et al., Biochem. Biophys. Res. Comm., (1978), vol. 80, pp. 49-57.
Fu, Q., Chen, X., Cui, H., Guo, Y., Chen, J., Shen, N., and Bao, C. (2008) Association of elevated transcript levels of interferon-inducible chemokines with disease activity and organ damage in systemic lupus erythematosus patients, Arthritis Res. Ther. 10, R112.
Gerszten, R. E., Accurso, F., Bernard, G. R., Caprioli, R. M., Klee, E.W., Klee, G.G., Kulla, I., Laguna, T. A., Roth, F. P., Sabatine, M., Srinivas, P., Wang, T. J., and Ware, L. B. (2008) Challenges in translating plasma proteomics from bench to bedside: update from the NHLBI Clinical Proteomics Programs, Am. J. Physiol. 295, L16-22.
Gibson DS, Banha J, Penque D, Costa L, Conrads TP, Cahill DJ, et al. Diagnostic and prognostic biomarker discovery strategies for autoimmune disorders. Journal of proteomics. Apr. 18, 2010;73(6): 1045-60.
Gigante A, Gasperini ML, Afeltra A, et al. Cytokines expression in SLE nephritis. Eur Rev Med Pharmacol Sci 2011, 15-24.
Gunneriusson, Appl Environ Microbial, (1999), vol. 65, No. 9, pp. 4134-4140.
Gustavsson E, Ek S, Steen J, et al. Surrogate antigens as targets for proteome-wide binder selection. New Biotechnology 2011; 28: 302-11.
Haab, B. B. (2006) Applications of antibody array platforms, Curr. Opin. Biotechnol. 17, 415-421.
Hahn et al., 2012, Arthritis Care & Research, 64(6):797-808.
Hanash, S. (2003) Disease proteomics, Nature 422, 226-232.
Hanash, S. M., Pitteri, S. J., and Faca, V. M. (2008) Mining the plasma proteome for cancer biomarkers, Nature 452, 571-579.
Hanes, Pluckthun, Proc Natl Acad Sci Usa, (1997), vol. 94, No. 10, pp. 4937-4942.
He, Taussig, Nucleic Acids Res, (1997), vol. 25, No. 24, pp. 5132-5134.

(56) References Cited

OTHER PUBLICATIONS

Hesselstrand, R., Scheja, A., and Akesson, A. (1998) Mortality and causes of death in a Swedish series of systemic sclerosis patients, Ann. Rheumatic Dis. 57, 682-686.
Hochberg, M. C. (1997) Updating the American College of Rheumatology revised criteria for the classification of systemic lupus erythematosus, Arthritis Rheum. 40, 1725.
Huang W, Hu C, Zeng H, et al. Novel systemic lupus erythematosus autoantigens identified by human protein microarray technology. Biochem Biophys Res Commun 2012; 418: 241-6.
Hughes, "Is it lupus? The St. Thomas' Hospital "alternative" criteria", Clin. Exp. Rheumatol., (1998), vol. 16, No. 3, pp. 250-252.
Hughes, Khamashta, "Seronegative antiphospholipid syndrome", Ann. Rheum. Dis., (2003), vol. 62, No. 12, p. 1127.
Huston et al., Proc. Natl. Acad. Sci. USA, (1988), vol. 85, p. 5879.
Ihaka R, Gentleman R. A language for data analysis and graphics. J Comp Graph Stat. 1996; 5: 299-314.
Ingvarsson, Johan, et al. Detection of pancreatic cancer using antibody microarray-based serum protein profiling. Proteomics. 2008, vol. 8, pp. 2211-2219.
Jenkins, R.E., Pennington, S.R., Proteomics, (2001), vol. 2, pp. 13-29.
Jin T, Almehed K, Carlsten H, Forsblad-d'Elia H. Decreased serum levels of TGF-beta1 are associated with renal damage in female patients with systemic lupus erythematosus. Lupus. Mar. 2012;21(3):310-8. PubMed PMID: 22072025.
Kenan, Methods Mol Biol, (1999), vol. 118, pp. 217-231.
Kerr LD, Adelsberg BR, Schulman P, Spiera H. Factor B activation products in patients with systemic lupus erythernatosus. A marker of severe disease activity. Arthritis Rheum 1989;32:1406-13.
Kieke et al., Proc Natl Acad Sci USA, (1999), vol. 96, No. 10, pp. 5651-5656.
Kingsmore, S. F. (2006) Multiplexed protein measurement: technologies and applications of protein and antibody arrays, Nat. Rev. Drug Discov. 5, 310-320.
Klareskog, Lars, Saxne, Tore and Yvonne, Enman. Reumatologi. Studentlitteratur. 2005, p. 144.
Kristensson M, Olsson K, Carlson J, et al. Design of recombinant antibody microarrays for urinary proteomics. Proteomics Clin Appl 2012 6:291-6.
Kunik, Ashkenazi and Ofran, 2012, 'Paratome: an online tool for systematic identification of antigen-binding regions in antibodies based on sequence or structure' Nucl. Acids Res., 40: W521-W524.
Lal et al., Drug Discov Today, (2002), vol. 7, No. 18, pp. 143-149.
Lefranc et al., 2003 IMGT unique numbering for immunoglobulin and T cell receptor variable domains and Ig superfamily V-like domains. Dev. Comp. Immunol., 27:55-77.
Lefranc et al., 2005 'IMGT unique numbering for immunoglobulin and T cell receptor constant domains and Ig superfamily C-like domains' Dev. Comp. Immunol., 29:185-203.
LeRoy, E. C., Black, C., Fleischmajer, R., Jablonska, S., Krieg, T., Medsger, T. A., Jr., Rowell, N., and Wollheim, F. (1988) Scleroderma (systemic sclerosis): classification, subsets and pathogenesis, J. Rheumatol. 15, 202-205.
Lertnawapan R, Bian A, Rho YH, et al. Cystatin C is associated with inflammation but not atherosclerosis in systemic lupus erythematosus. Lupus 2012; 21: 279-87.
Li QZ, Xie C, Wu TF, et al. Identification of autoantibody clusters that best predict lupus disease activity using glomerular proteome arrays. J Clin Invest 2005; 115 (12): 3428-39.
Li QZ, Zhou J, Wandstrat AE, et al. Protein array autoantibody profiles for insights into systemic lupus erythematosus and incomplete lupus syndromes. Clin Exp Immunol 2007; 147: 60-70.
Liu CC MS, Kao AH, Navratil JS, Ahearn JM. Cell-bound complement biomarkers for systemic lupus erythematosus: from benchtop to bedside. Rheum Dis Clin North Am 2010 36(1):161-72.
Liu CC, Ahearn JM. The search for lupus biomarkers. Best practice & research. Aug. 2009;23(4):507-23.
Liu CC, Kao AH, Hawkins OM, Manzi S, Sattar A, Wilson N, et al. Lymphocyte-bound complement activation products as biomarkers for diagnosis of systemic lupus erythematosus. Clinical and translational science. Aug. 2009;2(4):300-8.
Liu Bi-Cheng, et al. Application of antibody array technology in the analysis of urinary cytokine profiles in patients with chronic kidney disease. Am J Nephrol. 2006, vol. 26, pp. 483-490.
Liu, C. C., Manzi, S., and Ahearn, J. M. (2005) Biomarkers for systemic lupus erythematosus: a review and perspective, Curr. Opin. Rheumatol. 17, 543-549.
Lorber, M., Gershwin, M. E., and Shoenfeld, Y. (1994) The coexistence of systemic lupus erythematosus with other autoimmune diseases: the kaleidoscope of autoimmunity, Sem. Arthritis and Rheum. 24, 105-113.
Lu MM, Wang J, Pan HF, et al. Increased serum RANTES in patients with systemic lupus erythematosus. Rheumatol Int 2012; 32: 1231-3.
Manzi S, Navratil JS, Ruffing MJ, Liu CC, Danchenko N, Nilson SE, et al. Measurement of erythrocyte C4d and complement receptor 1 in systemic lupus erythematosus. Arthritis and rheumatism. Nov. 2004;50(11):3596-604.
Marks et al., J Mol Biol, (1991), vol. 222, No. 3, pp. 581-597.
Masi, A. T. (1988) Classification of systemic sclerosis (scleroderma): relationship of cutaneous subgroups in early disease to outcome and serologic reactivity, J. Rheumatol. 15, 894-898.
Matucci-Cerinic, M., Steen, V., Nash, P., and Hachulla, E. (2009) The complexity of managing systemic sclerosis: screening and diagnosis, Rheumatology (Oxf.) 48 Suppl 3, iii8-13.
Mayes, M. 0., Lacey, J. V., Jr., Beebe-Dimmer, J., Gillespie, B. W., Cooper, B., Laing, T. J., and Schottenfeld, D. (2003) Prevalence, incidence, survival, and disease characteristics of systemic sclerosis in a large US population, Arthritis Rheum. 48, 2246-2255.
Merrill JT BJ. The role of biomarkers in the assessment of lupus. Best Pract Res Clin Rheumatol. 2005 19(5):709-26.
Misra R, Gupta R. Biomarkers in lupus nephritis. Int J Rheum Dis 2015; 18: 219-32.
Miyara M, Chader D, Sage E, et al. Sialyl Lewis x (CD15s) identifies highly differentiated and most suppressive FOXP3high regulatory T cells in humans. Proc Natl Acad Sci U S A 2015; 112: 7225-30.
Mok CC LC. Pathogenesis of systemic lupus erythematosus. J Clin Pathol. 2003 56(7): 481-490.
Mok CC. Biomarkers for lupus nephritis: a critical appraisal. J Biomed Biotechnol 2010; 638413.
Mosley, K., Tam, F. W., Edwards, R. J., Crozier, J., Pusey, C. D., and Lightstone, L. (2006) Urinary proteomic profiles distinguish between active and inactive lupus nephritis, Rheumatology (Oxf.) 45, 1497-1504.
Narain S RH, Satoh M, Sarmiento M, Davidson R, Shuster J, Sobel E, Hahn P, Reeves WH. Diagnostic accuracy for lupus and other systemic autoimmune diseases in the community setting. Arch Intern Med. 2004 164(22):2435-41.
Navratil JS, Manzi S, Kao AH, Krishnaswami S, Liu CC, Ruffing MJ, et al. Platelet C4d is highly specific for systemic lupus erythematosus. Arthritis and rheumatism. Feb. 2006; 54(2):670-4. PubMed PMID: 16447243.
Nemoto et al., FESS LETT, (1997), vol. 414, No. 2, pp. 405-408.
Olsson N, Wallin S, James P, Borrebaeck Cak, Wingren C. Epitope-specificity of recombinant antibodies reveals promiscuous peptide-binding properties. Protein Science. 2012;21(12):1897-910.
Omenn, G. S., et al., (2005) Overview of the HUPO Plasma Proteome Project: results from the pilot phase with 35 collaborating laboratories and multiple analytical groups, generating a core dataset of 3020 proteins and a publicly-available database, Proteomics, 5, 3226-3245.
Ouyang H, Shi YB, Su N, Li LY. [Abnormality and significance of interleukin-9 and CD4(+)interleukin-9(+) T-cells in peripheral blood of patients with systemic lupus erythematosus]. Zhonghua Yi Xue Za Zhi 2013; 93: 99-103.
Pascual, V., Farkas, L., and Banchereau, J. (2006) Systemic lupus erythematosus: all roads lead to type I interferons, Curr. Opin. Immunol. 18, 676-682.

(56) References Cited

OTHER PUBLICATIONS

Pauly F, Dexlin-Mellby L, Ek S, et al. Protein Expression Profiling of Formalin-Fixed Paraffin-Embedded Tissue Using Recombinant Antibody Microarrays. Journal of Proteome Research 2013; 12: 5943-53.

Persson J, Backstrom M, Johansson H, Jirstrom K, Hansson GC, Ohlin M. Molecular Evolution of Specific Human Antibody against MUC1 Mucin Results in Improved Recognition of the Antigen on Tumor Cells. Tumor Biology. 2009;30(4):221-31.

Petersson L, Dexlin-Mellby L, Bengtsson AA, Sturfelt G, Borrebaeck CAK, Wingren C. Multiplexing of miniaturized planar antibody arrays for serum protein profiling—a biomarker discovery in SLE nephritis. Lab on a Chip 2014;14(11):1931-42.

Petri M, Orbai AM, Alarcon GS, Gordon C, Merrill JT, Fortin PR, et al. Derivation and validation of the Systemic Lupus International Collaborating Clinics classification criteria for systemic lupus erythematosus. Arthritis and rheumatism. Aug. 2012; 64(8):2677-86. PubMed PMID: 22553077. Pubmed Central PMCID: 3409311.

Pickering MC, Walport MJ. Links between complement abnormalities and systemic lupus erythematosus. Rheumatology (Oxford) 2000; 39: 133-41.

Pitashny, M., Schwartz, N., Qing, X., Hojaili, B., Aranow, C., Mackay, M., and Putterman, C. (2007) Urinary lipocalin-2 is associated with renal disease activity in human lupus nephritis, Arthritis Rheum. 56, 1894-1903.

Pope, J. E. (2002) Scleroderma overlap syndromes, Curr. Opin. Rheumatol. 14, 704-710.

Putterman C, Wu A, Reiner-Benaim A, et al. SLE-key((R)) rule-out serologic test for excluding the diagnosis of systemic lupus erythematosus: Developing the ImmunArray iCHIP((R)). J Immunol Methods 2016; 429: 1-6.

Radstake, T. R., van Bon, L., Breen, J., Hussiani, A., Hesselstrand, R., Wuttge, D. M., Deng, Y., Simms, R., Lubberts, E., and Lafyatis, R. (2009) The pronounced Th17 profile in systemic sclerosis (SSc) together with intracellular expression of TGFbeta and IFNgamma distinguishes SSc phenotypes, PloS one 4, e5903.

Rahman A ID. Systemic lupus erythematosus. N Engl J Med. 2008 358(9):929-39.

S. Manzi. Lupus update: perspective and clinical pearls. Cleve Clin J Med. 2009 76(2):137-42.

Sangle, "Livedo reticularis and pregnancy morbidity in patients negative for antiphospholipid antibodies", Ann. Rheum. Dis., (2005), vol. 64, No. 1, pp. 147-148.

Santi et al., J Mol Biol, (2000), vol. 296, No. 2, pp. 497-508.

Schervish, Mark J. (Nov. 1987). "A Review of Multivariate Analysis". Statistical Science 2 (4): 396-413.

Schur, Peter H. Systemic Lupus Erythematosus. Encyclopedia of Life Sciences. 2009, pp. 1-11.

Schwartz, Noa, Michaelson, Jennifer S and Putterman, Chaim. Lipocalin-2, TWEAK, and other cytokines as urinary biomarkers for lupus nephritis. Ann. N.Y. Acad. Sci. 2007, vol. 1109, pp. 265-274.

Sedighi S, Aghaei M, Musavi S, Nomali M. Relationship between Serum Level of Interleukin-2 in Patients with Systemic Lupus Erythematosus and Disease Activity in Comparison with Control Group. J Clin Diagn Res 2014; 8: MC16-8.

Shusta et al., J Mol Biol, (1999), vol. 292, No. 5, pp. 949-956.

Sjoholm, A. G., Martensson, U., and Sturfelt, G. (1997) Serial analysis of autoantibody responses to the collagen-like region of C1q, collagen type II, and double stranded DNA in patients with systemic lupus erythematosus, J. Rheumatol. 24, 871-878.

Skerra et al., Science, (1988), vol. 240, p. 1038.

Smith EL SR. The American College of Rheumatology criteria for the classification of systemic lupus erythematosus: strengths, weaknesses, and opportunities for improvement. Lupus 1999;8(8):586-95.

Smith, Science, (1985), vol. 228, No. 4705, pp. 1315-1317.

Soderlind E SL, Jirholt P, Kobayashi N, Alexeiva V, Aberg AM, Nilsson A, Jansson B, Ohlin M, Wingren C, Danielsson L, Carlsson R, Borrebaeck CA. Recombining germline-derived CDR sequences for creating diverse single-framework antibody libraries. Nat Biotechnol 2000 18(8):852-6.

Stahl-Hallengren, C., Jonsen, A., Nived, O., and Sturfelt, G. (2000) Incidence studies of systemic lupus erythematosus in Southern Sweden: increasing age, decreasing frequency of renal manifestations and good prognosis, J. Rheumatol. 27, 685-691.

Sturfelt G, and Sjoholm, A. G. Complement components, complement activation, and acute phase response in systemic lupus erythematosus. Int Arch Allergy Appl Immunol. 1984;75:75-83.

Sturfelt, G., Sjoholm, A. G., and Svensson, 8. (1983) Complement components, C1 activation and disease activity in SLE, Int. Arch. Allergy Appl. Immunol. 70, 12-18.

Su DL, Lu ZM, Shen MN, Li X, Sun LY. Roles of pro- and anti-inflammatory cytokines in the pathogenesis of SLE. J Biomed Biotechnol 2012; 347141.

Suh CH, Kim HA. Cytokines and their receptors as biomarkers of systemic lupus erythematosus. Expert review of molecular diagnostics. Mar. 2008; 8(2): 189-98.

Sui W HX, Che W, Yang M, Dai Y. The applied basic research of systemic lupus erythematosus based on the biological omics. Genes Immun. 2013 14(3):133-46.

Suzuki, M., Ross, G. F., Wiers, K., Nelson, S., Bennett, M., Passo, M. H., Devarajan, P., and Brunner, H. I. (2007) Identification of a urinary proteomic signature for lupus nephritis in children, Ped. Nephol. 22, 2047-2057.

Talaat RM, Mohamed SF, Bassyouni IH, Raouf AA. Th1/Th2/Th17/Treg cytokine imbalance in systemic lupus erythematosus (SLE) patients: Correlation with disease activity. Cytokine 2015; 72: 146-53.

Tan EM CA, Fries JF, Masi AT, McShane DJ, Rothfield NF, Schaller JG, Talal N, Winchester RJ. The 1982 revised criteria for the classification of systemic lupus erythematosus. Arthritis Rheum 1982 25(11):1271-7.

Thompson et al., 1994, Nucl. Acid Res. 22: 4673-4680.

Thongboonkerd, Visith. Practical points in urinary proteomics. Journal of proteome research. 2007, vol. 6, pp. 3881-3890.

Tjalsma H, Schaeps RM, Swinkels DW. Immunoproteomics: From biomarker discovery to diagnostic applications. Proteomics Clin Appl 2008; 2: 167-80.

Tsokos GC. Systemic lupus erythematosus. N Engl J Med 2011; 365: 2110-21.

Umare V, Pradhan V, Nadkar M, et al. Effect of proinflammatory cytokines (IL-6, TNF-alpha, and IL-1beta) on clinical manifestations in Indian SLE patients. Mediators Inflamm 2014:385297.

Urquizu-Padilla, M., Balada, E., Cortes, F., Perez, E. H., Vilardell-Tarres, M., and Ordi-Ros, J. (2009) Serum levels of soluble CD40 ligand at flare and at remission in patients with systemic lupus erythematosus, J. Rheumatol. 36, 953-960.

Varga J. Systemic sclerosis: an update. Bulletin of the NYU hospital for joint diseases. 2008;66(3):198-202.

Varga, J. and Abraham, D. (2007) Systemic sclerosis: a prototypic multisystem fibrotic disorder, J. Clin. Invest. 117, 557-567.

Vazgiourakis VM, Zervou MI, Choulaki C, Bertsias G, Melissourgaki M, Yilmaz N, et al. A common SNP in the CD40 region is associated with systemic lupus erythematosus and correlates with altered CD40 expression: implications for the pathogenesis. Annals of the rheumatic diseases. Dec. 2011;70(12):2184-90.

VC.. Kyttaris. Systemic lupus erythematosus: from genes to organ damage. Methods Mal Biol 2010;662:265-83.

Walport MJ. Complement and systemic lupus erythematosus. Arthritis research. 2002;4 Suppl 3:S279-93.

Ward etal., Nature, (1989), vol. 341, p. 544.

Wingren C BC. Antibody microarray analysis of directly labelled complex proteomes. Curr Opin Biotechnol. 2008 19(1):55-61.

Wingren C IJ, Dexlin L, Szul D, Borrebaeck CA. Design of recombinant antibody microarrays for complex proteome analysis: choice of sample labeling-tag and solid support. Proteomics 2007 7(17):3055-65.

Wingren, C., and Borrebaeck, C. A. K. (2006) Antibody microarrays: current status and key technological advances, Omics 10, 411-427.

(56) References Cited

OTHER PUBLICATIONS

Wingren, C., and Borrebaeck, C. A. K. (2007) Progress in miniaturization of protein arrays—a step closer to high-density nanoarrays, Drug Discov. Today 12, 813-819.
Wingren, C., Ingvarsson, J., Lindstedt, M., and Borrebaeck, C. A. K. (2003) Recombinant antibody microarrays—a viable option?, Nat. Biotechnol. 21, 223.
Wingren, Christer and Borrebaeck, Carl A K. Antibody-based microarrays. Microchip methods in diagnostics. 2009, vol. 509, pp. 57-83.
Winter, Milstein, Nature, (1991), vol. 349, pp. 293-299.
Wu and Kabat, 1970, 'An analysis of the sequences of the variable regions of Bence Jones proteins and myeloma light chains and their implications for antibody complementarity.' J. Exp. Med., 132:211-250.
Wuttge, D. M., Wildt, M., Geborek, P., Wollheim, F. A., Scheja, A., and Akesson, A. (2007) Serum IL-15 in patients with early systemic sclerosis: a potential novel marker of lung disease, Arthritis Res. Ther. 9, R85.
Yamamoto, T. (2009) Scleroderma—pathophysiology, Eur. J. Dermatol. 19, 14-24.
Yee, Chee-Seng, et al. Assessment of disease activity and quality of life in systemic lupus erythematosus—new aspects. Best practice & research clinical Rheumatology (2009), vol. 23, pp. 457-467.
Zhang W, Shi Q, Xu X, et al. Aberrant CD40-induced NF-kappaB activation in human lupus B lymphocytes. PLoS One 2012; 7: e41644.
GenBank database—ht /www.ncbi.nlm.nih.gov/genbank/.
Burges, 1998, Data Mining and Knowledge Discovery, 2:121-167.
Zola, Monoclonal Antibodies: A manual of techniques, (CRC Press, 1988).
J G R Hurrell, Monoclonal Hybridoma Antibodies: Techniques and applications, (CRC Press, 1982).
J-F Chatal, Monoclonal Antibodies in Immunoscintigraphy, CRC Press, 1989.
Delfani et al., Deciphering systemic lupus erythematosus-associated serum biomarkers reflecting apoptosis and disease activity, Lupus, 26(4): 373-387, 2016.
Cristianini N, Shawe-Taylor J. An introduction to support vector machines and other kernel-based learning methods. Cambridge Univeristy Press 2000.
Crowther, The ELISA Guidebook (Methods in Molecular Biology), 2000, Humana Press.
Steinhauer C, Wingren C, Hager AC, Borrebaeck CA. Single framework recombinant antibody fragments designed for protein chip applications. Biotechniques 2002; Suppl:38-45.
Wingren C, Steinhauer C, Ingvarsson J, Persson E, Larsson K, Borrebaeck CA. Microarrays based on affinity-tagged single-chain Fv antibodies: sensitive detection of analyte in complex proteomes. Proteomics 2005; 5:1281-91.
Delfani P, Dexlin Mellby L, Nordstrom M, Holmer A, Ohlsson M, Borrebaeck CA, et al. Technical Advances of the Recombinant Antibody Microarray Technology Platform for Clinical Immunoproteomics. PLoS One. 2016; 11(7):e0159138.
Lewis et al., 2016, World J Gastroenterol. 22(32): 7175-7185.
Johnson We, Li C, Rabinovic A. Adjusting batch effects in microarray expression data using empirical Bayes methods. Biostatistics. 2007; 8(1):118-27.
Thomas, S.L., Griffiths, C., Smeeth, L., Rooney, C. & Hall, A.J. Burden of mortality associated with autoimmune diseases among females in the United Kingdom. Am J Public Health 100, 2279-2287 (2010).
Walsh, S.J. & Rau, L.M. Autoimmune diseases: a leading cause of death among young and middle-aged women in the United States. Am J Public Health 90, 1463-1466 (2000).
Manoussakis, M.N. et al. Sjogren's syndrome associated with systemic lupus erythematosus: clinical and laboratory profiles and comparison with primary Sjogren's syndrome. Arthritis and rheumatism 50, 882-891 (2004).
Toro-Dominguez, D., Carmona-Saez, P. & Alarcon-Riquelme, M.E. Shared signatures between rheumatoid arthritis, systemic lupus erythematosus and Sjogren's syndrome uncovered through gene expression meta-analysis. Arthritis research & therapy 16, 489 (2014).
Alexander, E.L., Hirsch, T.J., Arnett, F.C., Provost, T.T. & Stevens, M.B. Ro(SSA) and La(SSB) antibodies in the clinical spectrum of Sjogren's syndrome. J Rheumatol 9, 239-246 (1982).
Falk, R.J. & Jennette, J.C. Anti-neutrophil cytoplasmic autoantibodies with specificity for myeloperoxidase in patients with systemic vasculitis and idiopathic necrotizing and crescentic glomerulonephritis. N Engl J Med 318, 1651-1657 (1988).
Rekvig, O.P. Anti-dsDNA antibodies as a classification criterion and a diagnostic marker for systemic lupus erythematosus: critical remarks. Clin Exp Immunol 179, 5-10 (2015).
Tervaert, J.W. et al. Autoantibodies against myeloid lysosomal enzymes in crescentic glomerulonephritis. Kidney Int 37, 799-806 (1990).
Rasmussen, A. et al. Previous diagnosis of Sjogren's Syndrome as rheumatoid arthritis or systemic lupus erythematosus. Rheumatology (Oxford) 55, 1195-1201 (2016).
Haller-Kikkatalo, K. et al. Demographic associations for autoantibodies in disease-free individuals of a European population. Sci Rep 7, 44846 (2017).
Tan, E.M. et al. Range of antinuclear antibodies in "healthy" individuals. Arthritis and rheumatism 40, 1601-1611 (1997).
Wandstrat, A.E. et al. Autoantibody profiling to identify individuals at risk for systemic lupus erythematosus. Journal of autoimmunity 27, 153-160 (2006).
Borrebaeck, C.A., Sturfelt, G. & Wingren, C. Recombinant antibody microarray for profiling the serum proteome of SLE. Methods Mal Biol 1134, 67-78 (2014).
Vitali, C. et al. Classification criteria for Sjogren's syndrome: a revised version of the European criteria proposed by the American-European Consensus Group. Annals of the rheumatic diseases 61, 554-558 (2002).
Sall, A. et al. Generation and analyses of human synthetic antibody libraries and their application for protein microarrays. Protein engineering, design & selection: PEDS 29, 427-437 (2016).
Skoog, P. et al. Tumor tissue protein signatures reflect histological grade of breast cancer. PloS one 12, e0179775 (2017).
Wu, Y.W. & Wooldridge, P.J. The impact of centering first-level predictors on individual and contextual effects in multilevel data analysis. Nursing research 54, 212-216 (2005).
Benjamini and Hochberg. Controlling the false discovery rate: a practical and powerful approach to multiple testing. Journal of the Royal Statistical Society Series B 57, 12 (1995).
Cooper, G.S., Bynum, M.L. & Somers, E.C. Recent insights in the epidemiology of autoimmune diseases: improved prevalence estimates and understanding of clustering of diseases. Journal of autoimmunity 33, 197-207 (2009).
Arbuckle, M.R. et al. Development of autoantibodies before the clinical onset of systemic lupus erythematosus. N Engl J Med 349, 1526-1533 (2003).
Eriksson, C. et al. Autoantibodies predate the onset of systemic lupus erythematosus in northern Sweden. Arthritis research & therapy 13, R30 (2011).
Van Gaalen, F.A. et al. Autoantibodies to cyclic citrullinated peptides predict progression to rheumatoid arthritis in patients with undifferentiated arthritis: a prospective cohort study. Arthritis and rheumatism 50, 709-715 (2004).
Visser, H., le Cessie, S., Vos, K., Breedveld, F.C. & Hazes, J.M. How to diagnose rheumatoid arthritis early: a prediction model for persistent (erosive) arthritis. Arthritis and rheumatism 46, 357-365 (2002).
Mohan, C. & Assassi, S. Biomarkers in rheumatic diseases: how can they facilitate diagnosis and assessment of disease activity? BMJ 351, h5079 (2015).
Petersson, L. et al. Miniaturization of multiplexed planar recombinant antibody arrays for serum protein profiling. Bioanalysis 6, 1175-1185 (2014).

(56) References Cited

OTHER PUBLICATIONS

Chen, M., Daha, M.R. & Kallenberg, C.G. The complement system in systemic autoimmune disease. Journal of autoimmunity 34, J276-286 (2010).

Pickart, C.M. Mechanisms underlying ubiquitination. Annu Rev Biochem 70, 503-533 (2001).

Weissman, A.M. Themes and variations on ubiquitylation. Nat Rev Mol Cell Biol 2, 169-178 (2001).

Espinosa, A. et al. The Sjogren's syndrome-associated autoantigen Ro52 is an E3 ligase that regulates proliferation and cell death. J Immunol 176, 6277-6285 (2006).

Feldmann, M. & Maini, R.N. Anti-TNF alpha therapy of rheumatoid arthritis: what have we learned? Annu Rev Immunol 19, 163-196 (2001).

Lipsky, P.E. et al. Infliximab and methotrexate in the treatment of rheumatoid arthritis. Anti-Tumor Necrosis Factor Trial in Rheumatoid Arthritis with Concomitant Therapy Study Group. N Engl J Med 343, 1594-1602 (2000).

Choy, E.H. et al. Therapeutic benefit of blocking interleukin-6 activity with an anti-interleukin-6 receptor monoclonal antibody in rheumatoid arthritis: a randomized, double-blind, placebo-controlled, dose-escalation trial. Arthritis and rheumatism 46, 3143-3150 (2002).

Kaleta, B. Role of osteopontin in systemic lupus erythematosus. Arch Immunol Ther Exp (Warsz) 62, 475-482 (2014).

Liu et al., Biomarkers in systemic lupus erythematosus: challenges and prospects for the future. Ther Adv Musculoskel Dis, 5(4), 210-233, 2013.

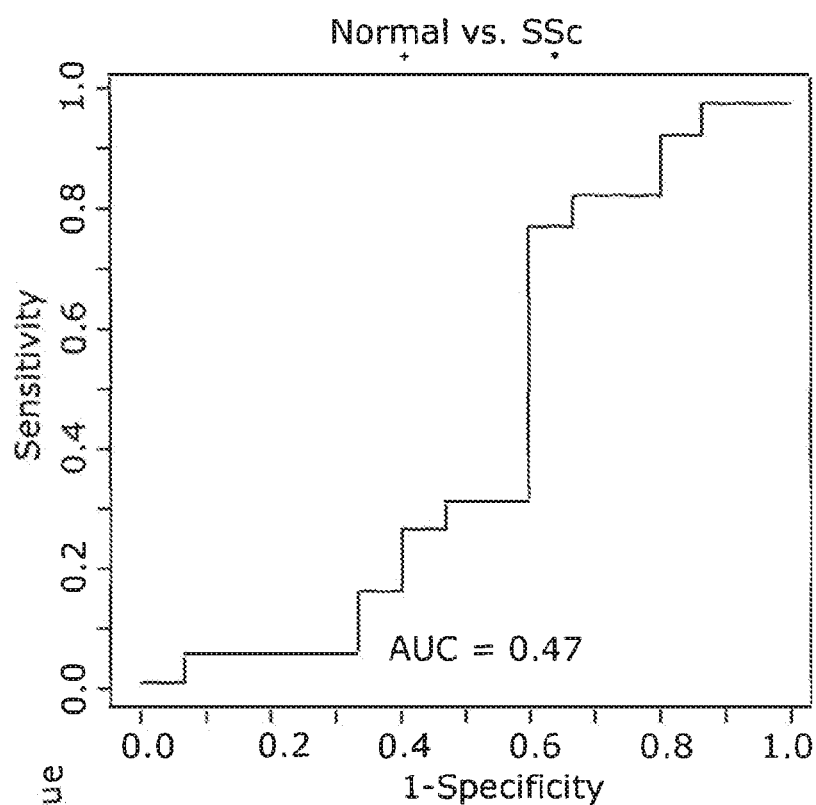
Fig. 1A(1)
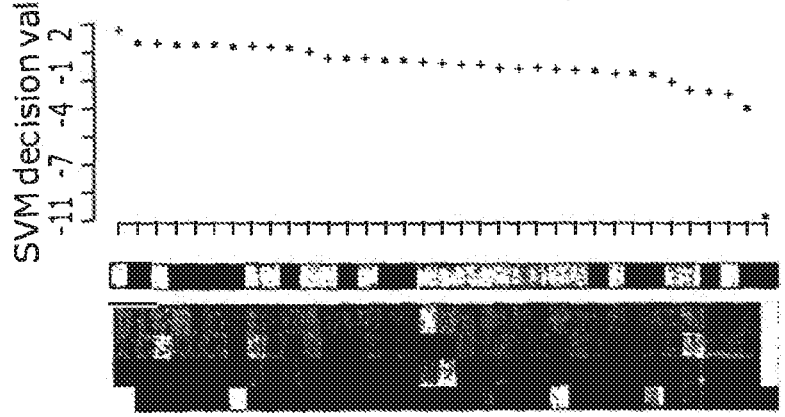
Fig. 1A(2)
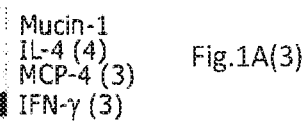
Fig. 1A(3)

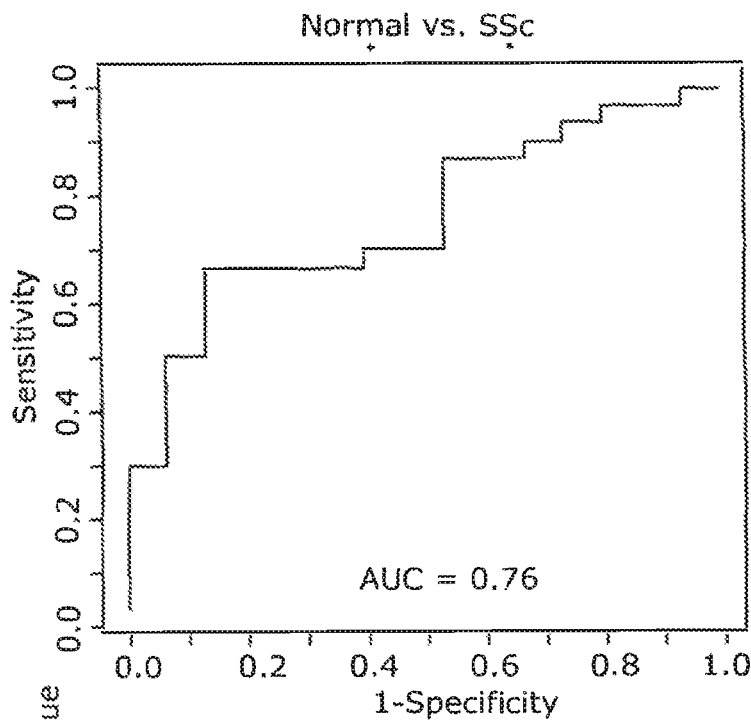
Fig. 1B(1)
Fig. 1B(2)
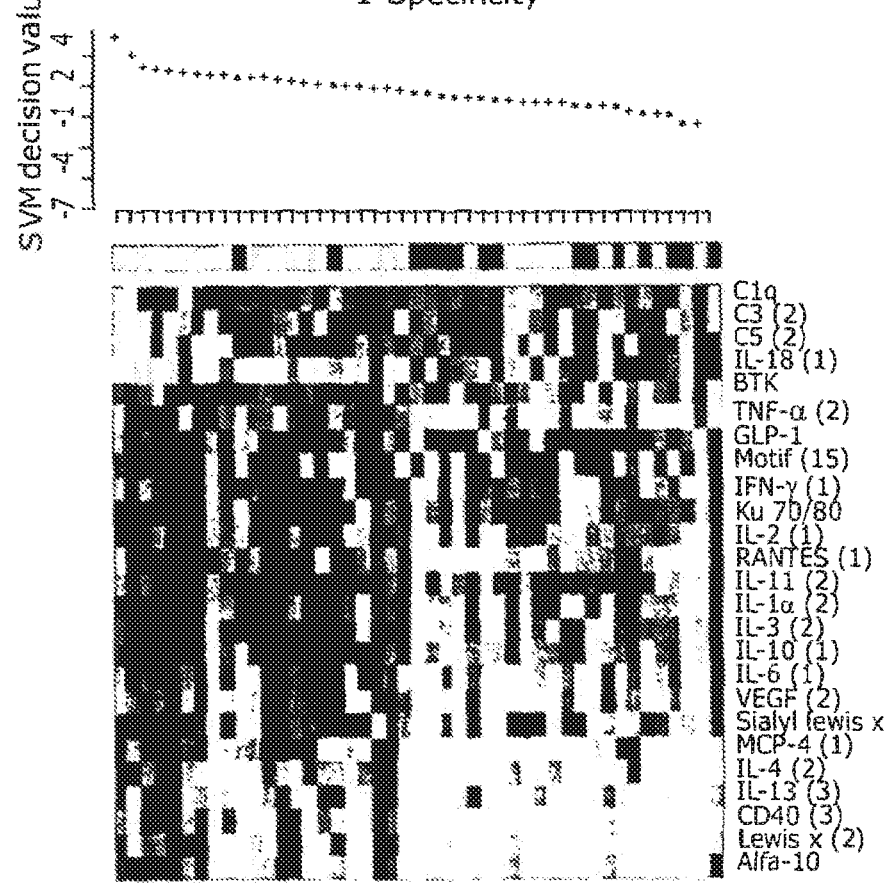
Fig. 1B(3)

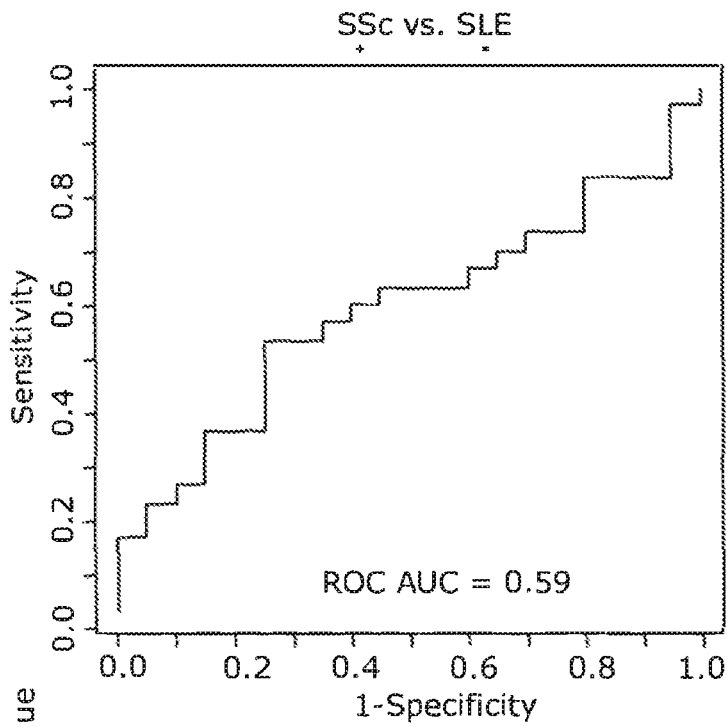
Fig. 1C(1)
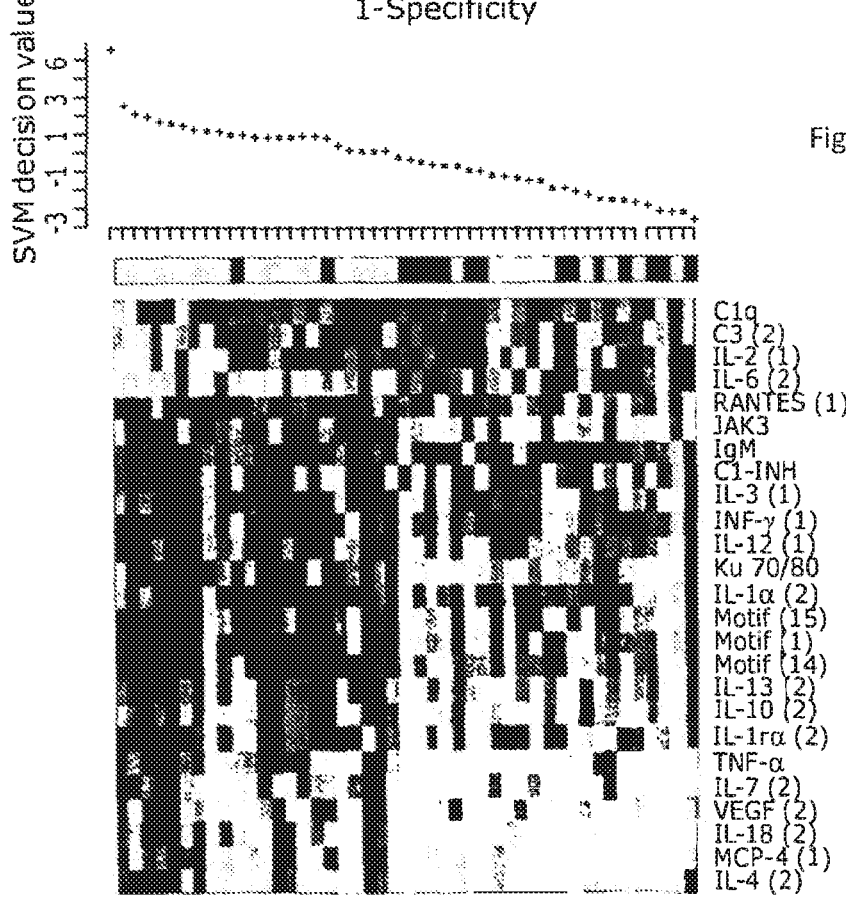
Fig. 1C(2)
Fig. 1C(3)

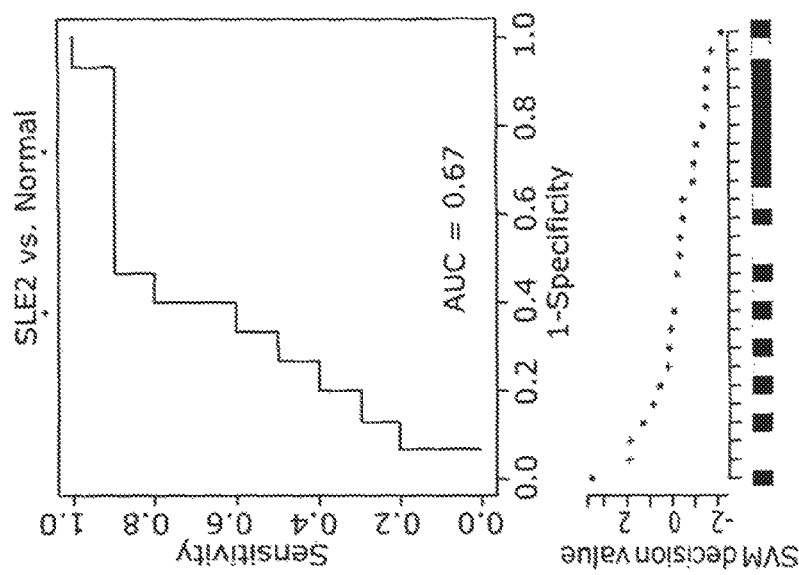
Fig. 3B(1) Fig. 3B(2)
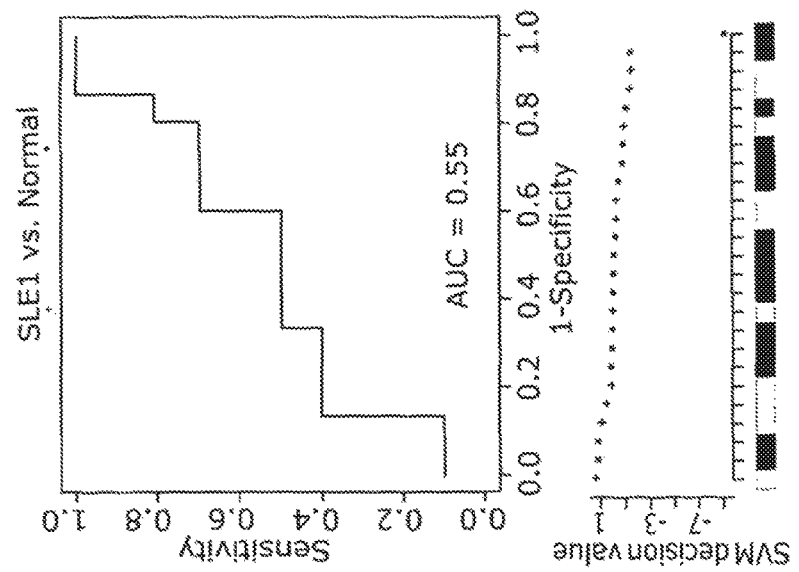
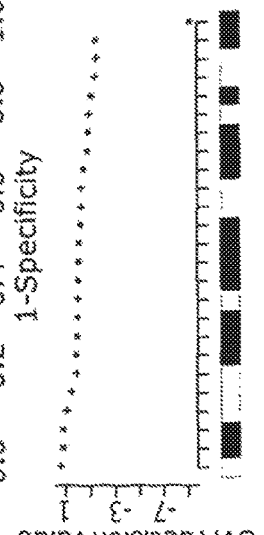
Fig. 3A(1) Fig. 3A(2)

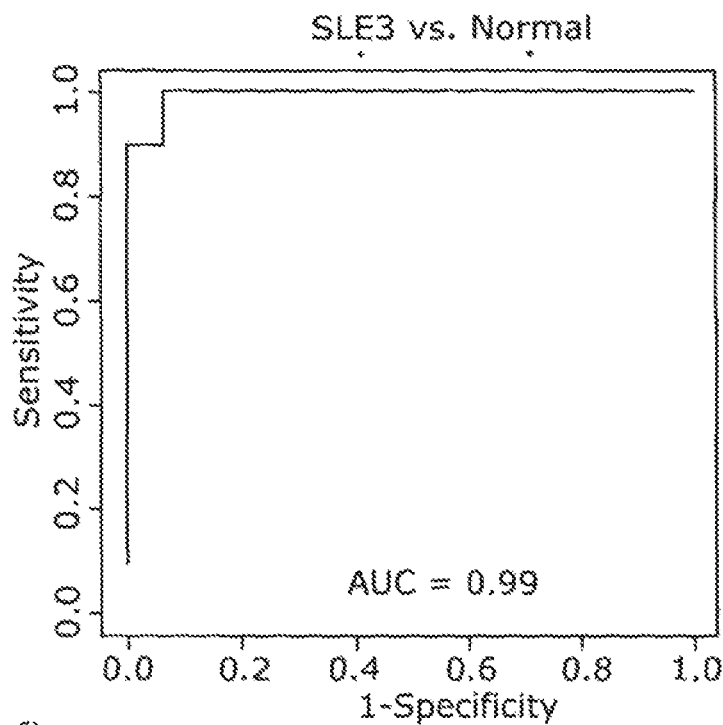
Fig. 3C(1)
Fig 3C(2)
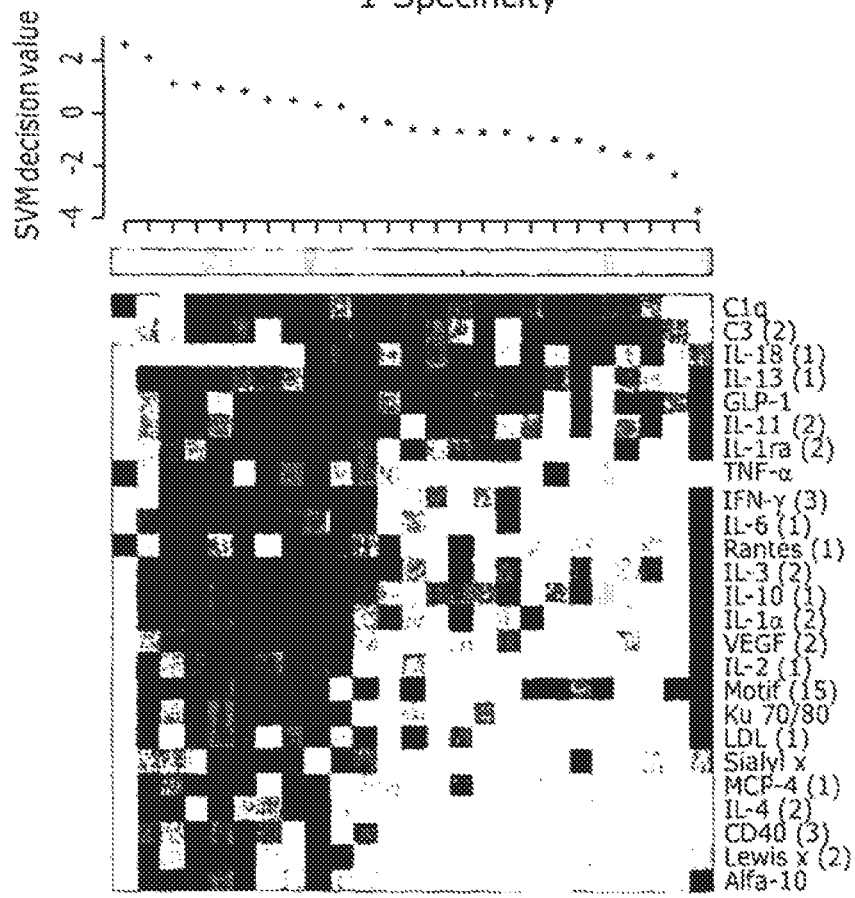
Fig 3C(3)

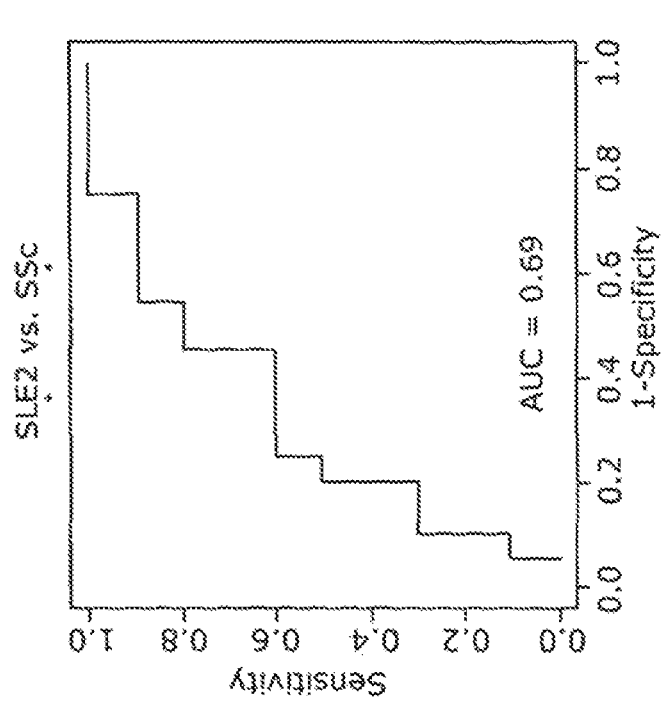
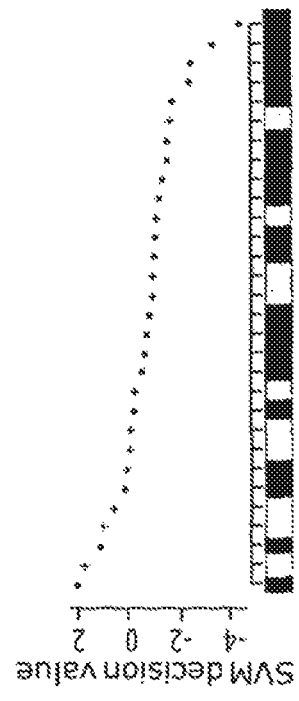
Fig. 4B(1)          Fig. 4B(2)
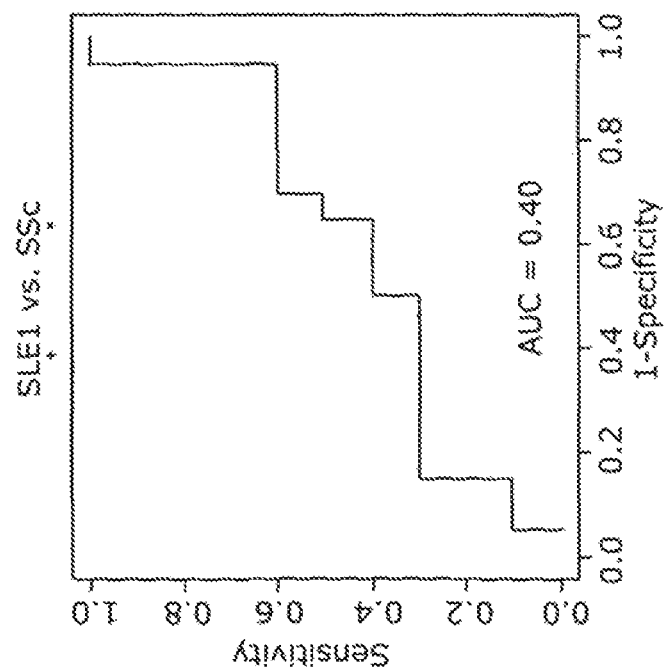
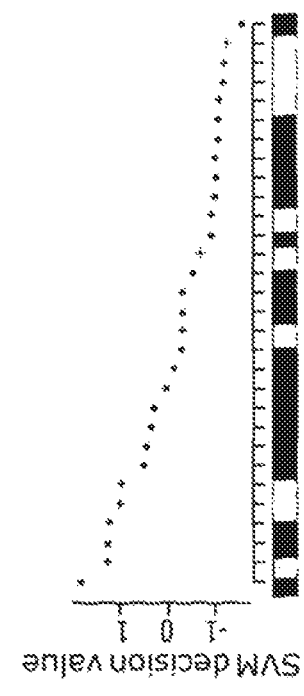
Fig. 4A(1)          Fig. 4A(2)

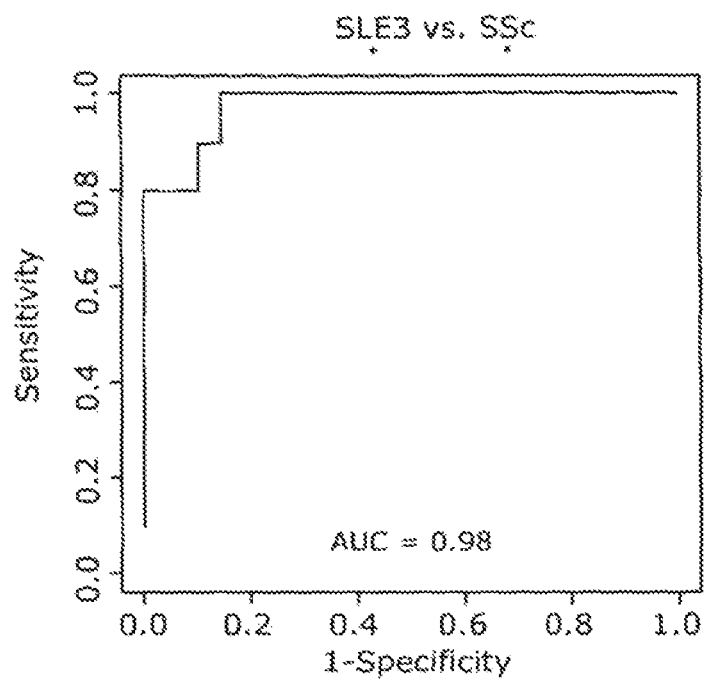
Fig. 4C(1)
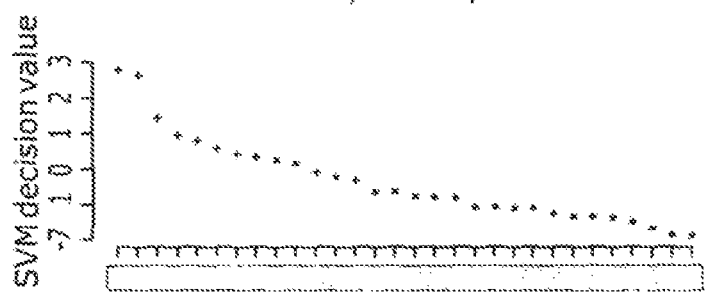
Fig. 4C(2)
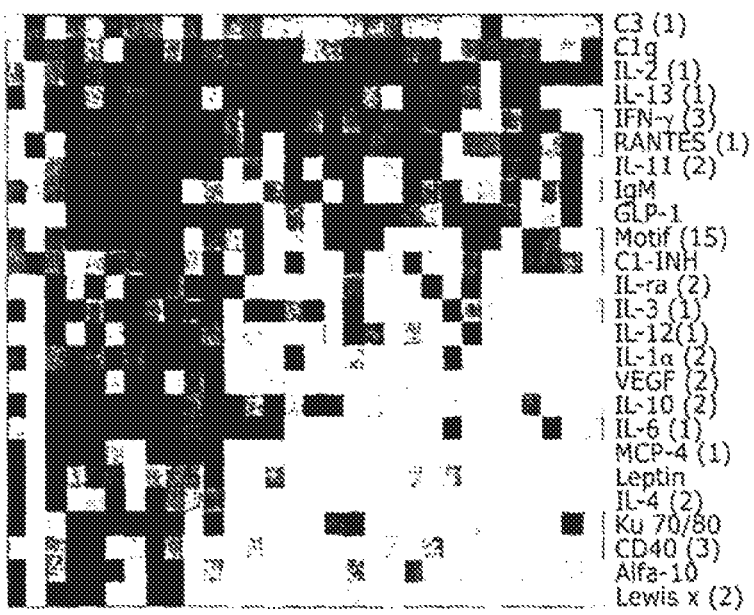
Fig. 4C(3)

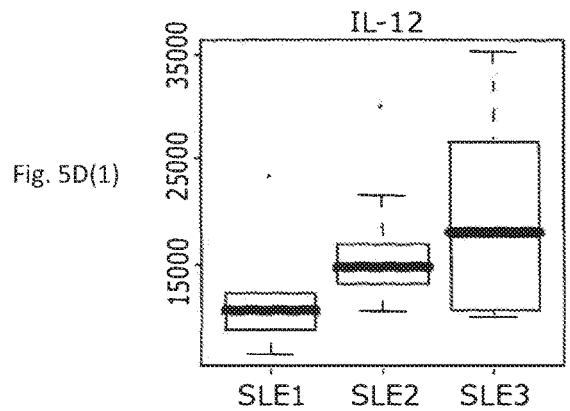
Fig. 5D(1)
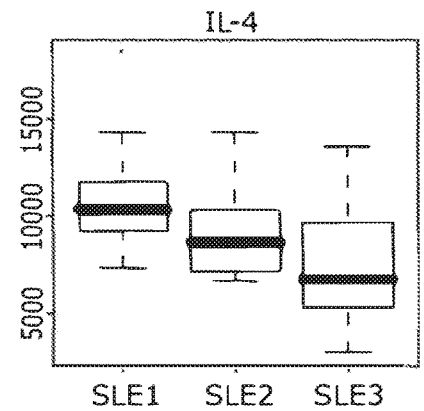
Fig. 5D(4)
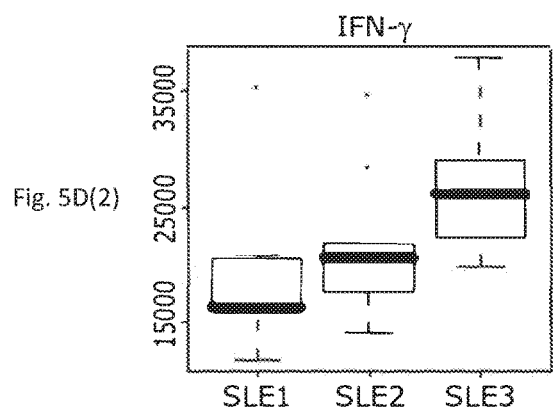
Fig. 5D(2)
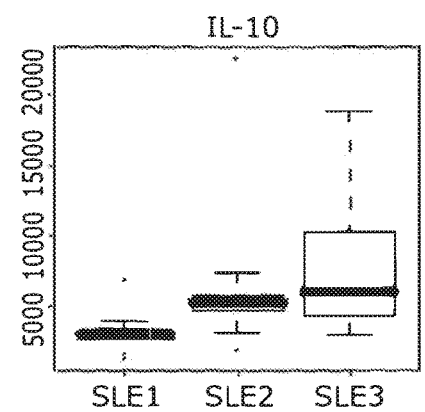
Fig. 5D(5)
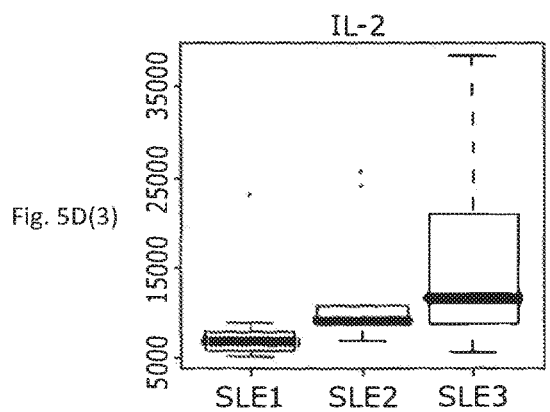
Fig. 5D(3)
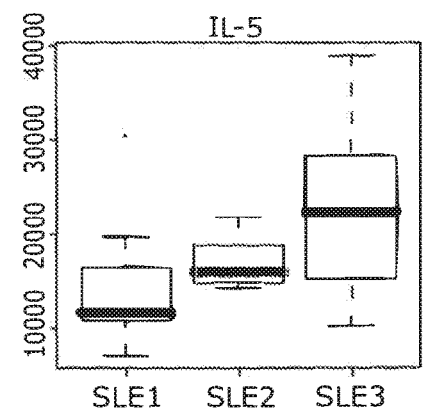
Fig. 5D(6)

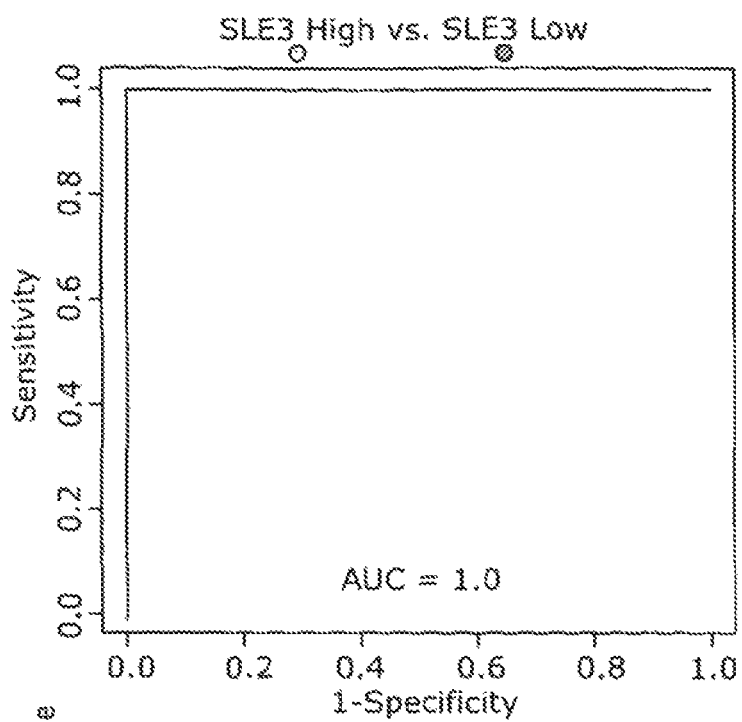
Fig. 7A
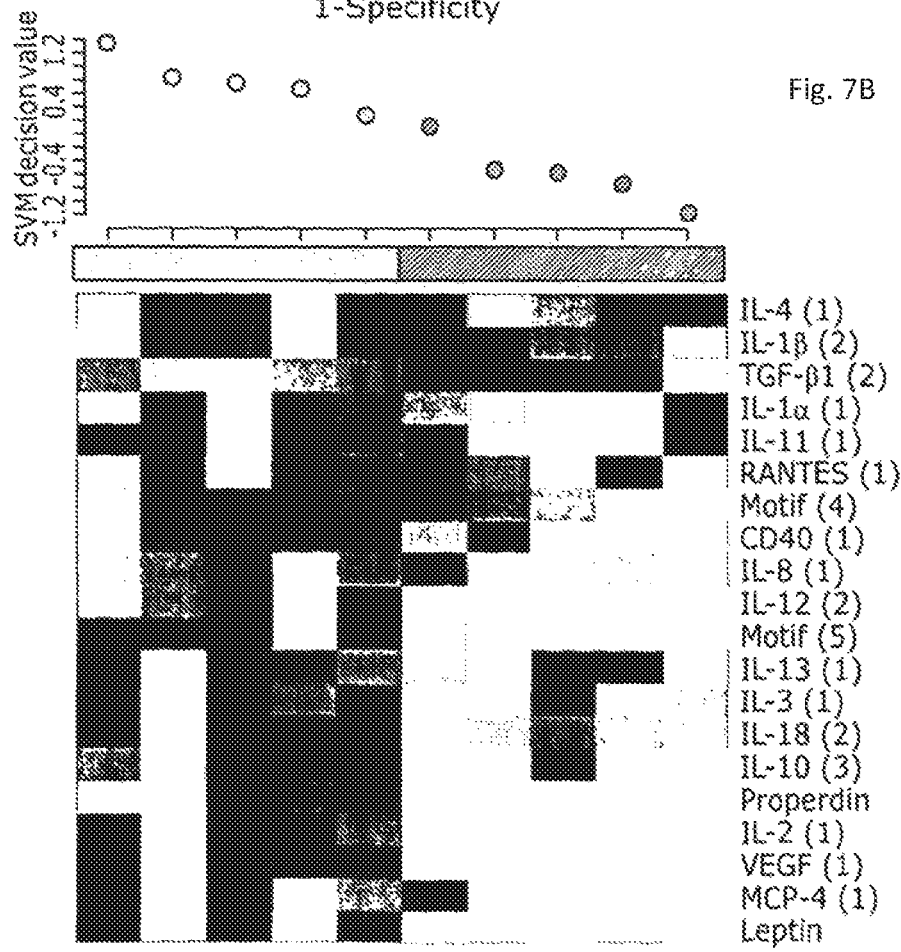
Fig. 7B
Fig. 7C

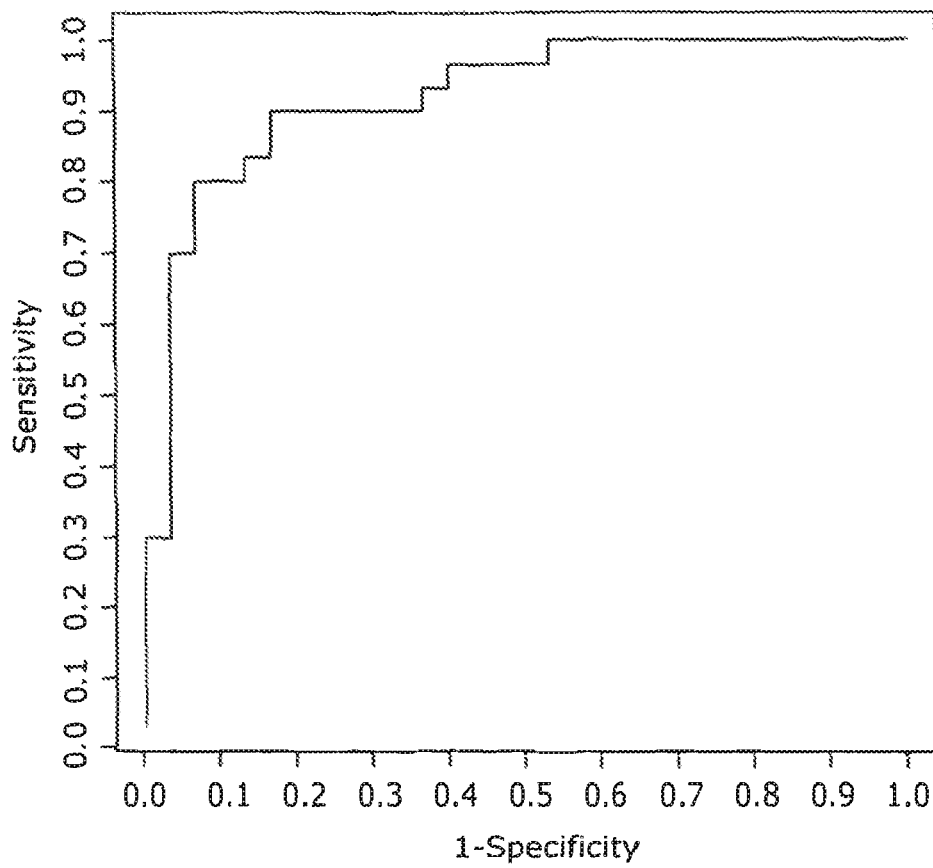
Fig. 11A
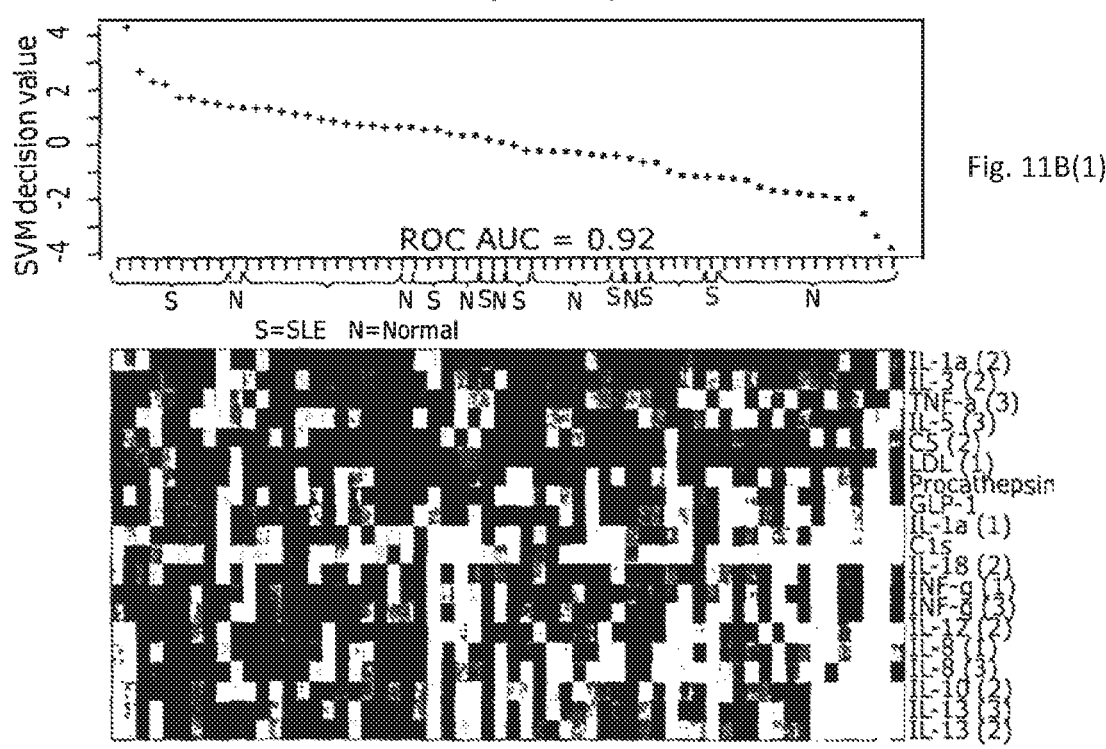
Fig. 11B(1)
Fig 11B(2)

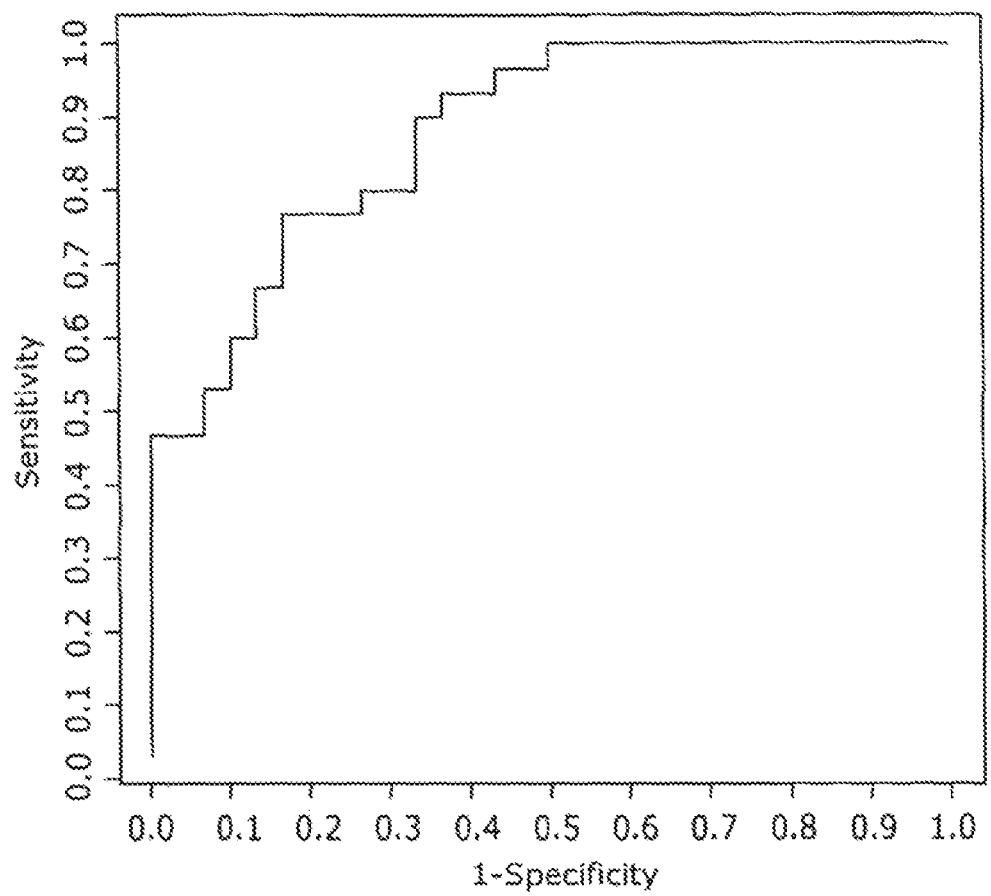
Fig. 11C(1)
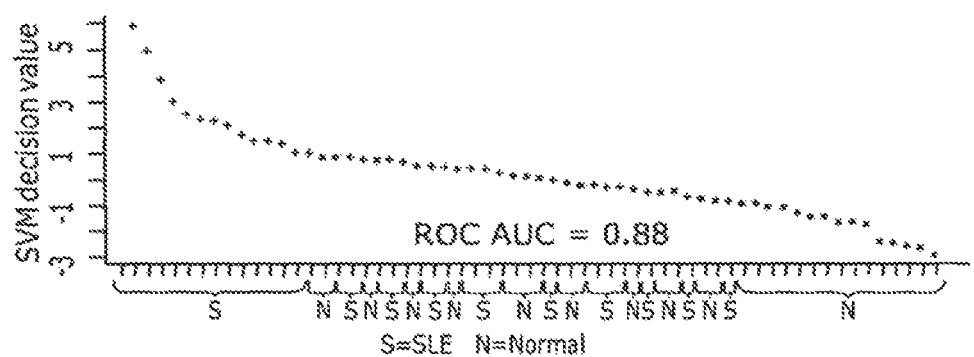
Fig. 11C(2)
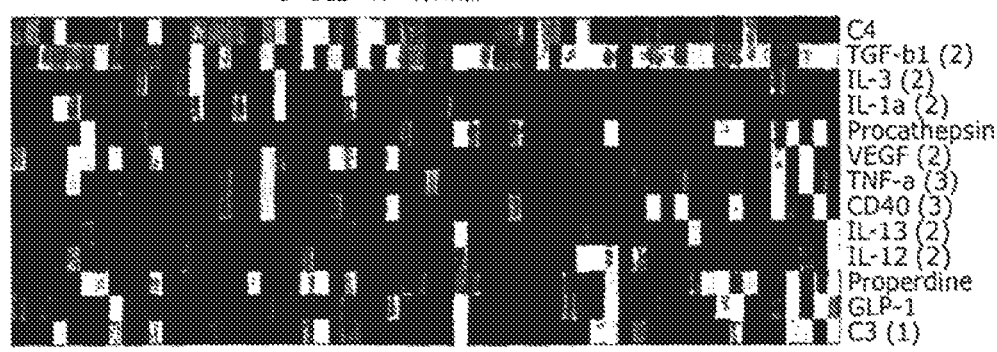
Fig 11D

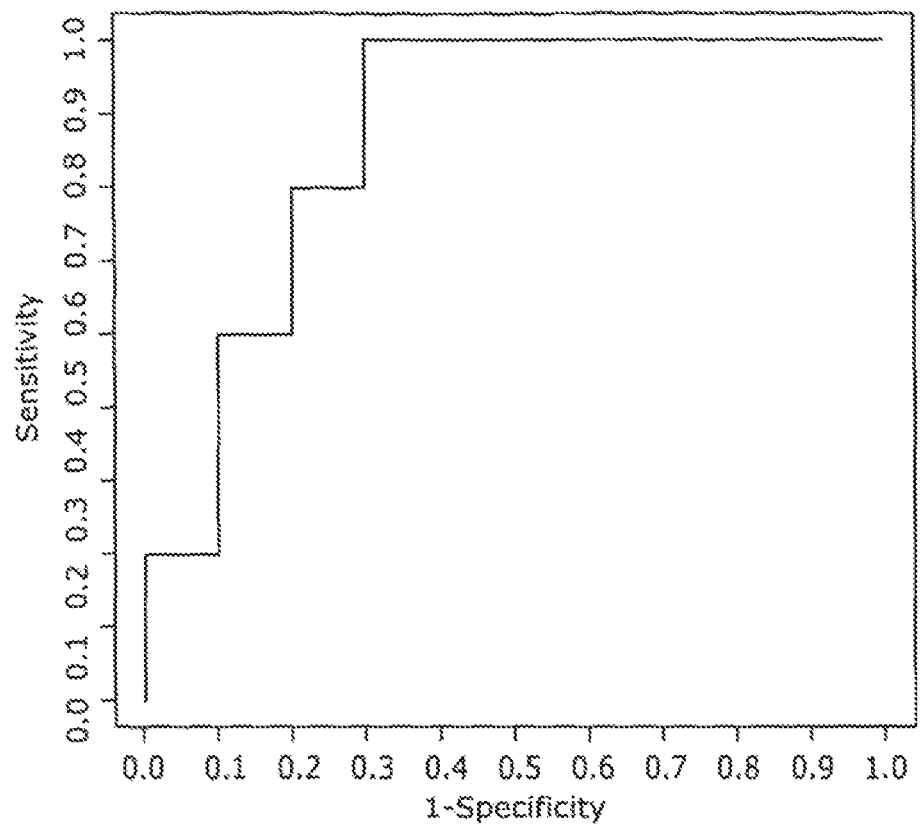
Fig 13A
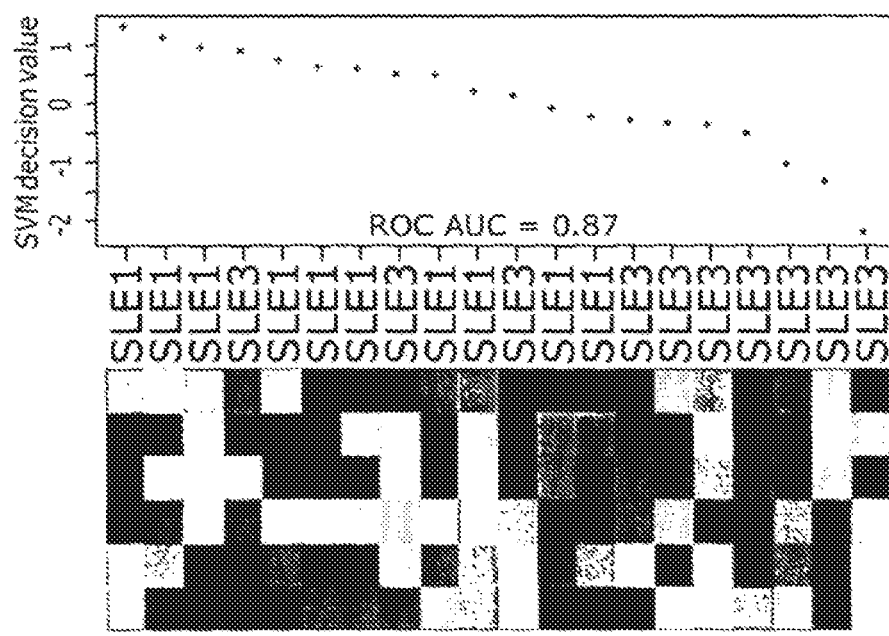
Fig. 13B(1)
Fig. 13B(2)

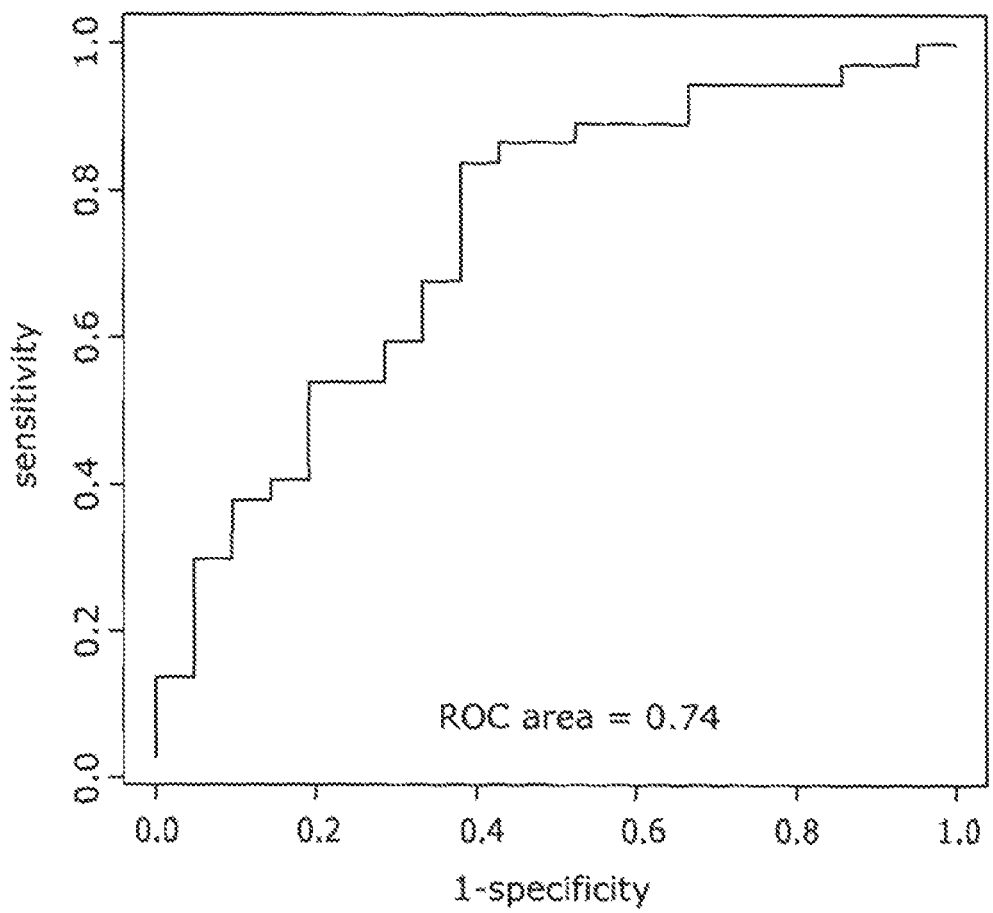
Fig. 17A(1)
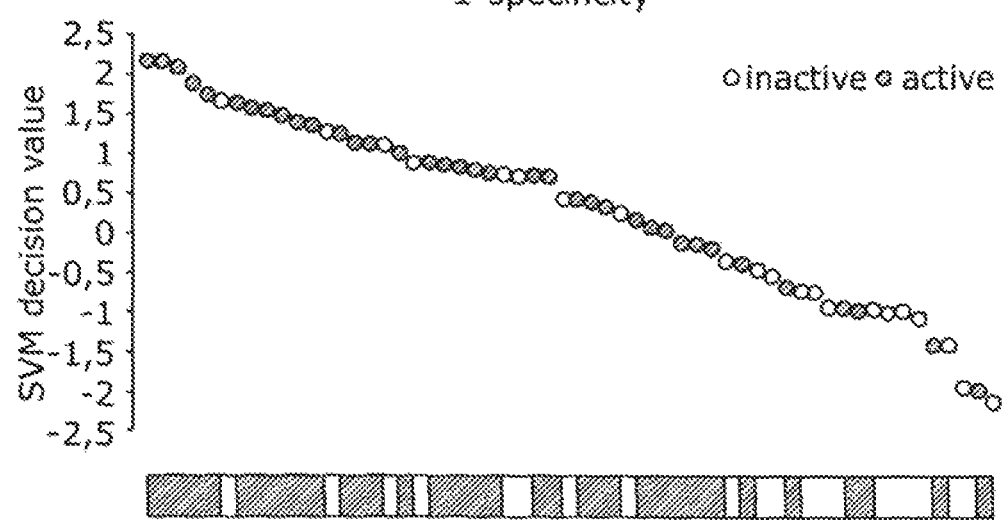
Fig. 17A(2)

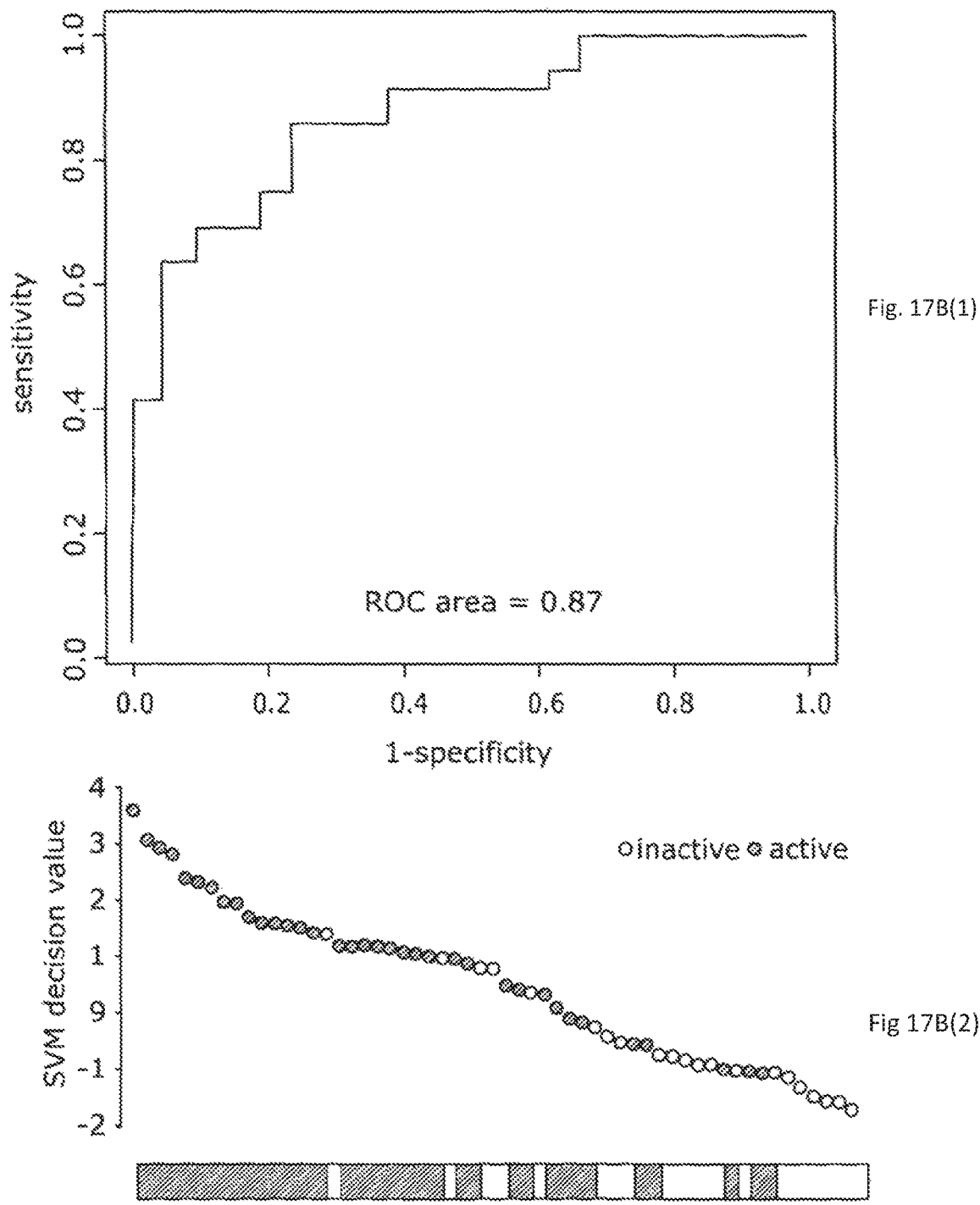
Fig. 17B(1)
Fig 17B(2)

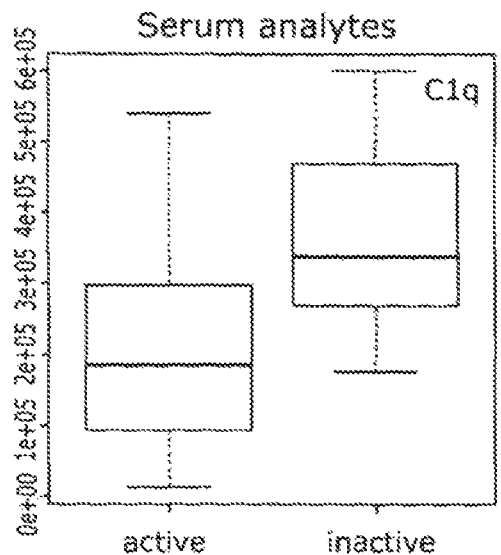
Fig. 18B(1)
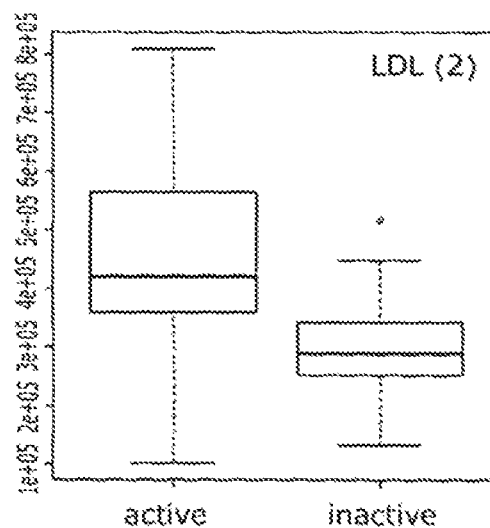
Fig. 18B(2)
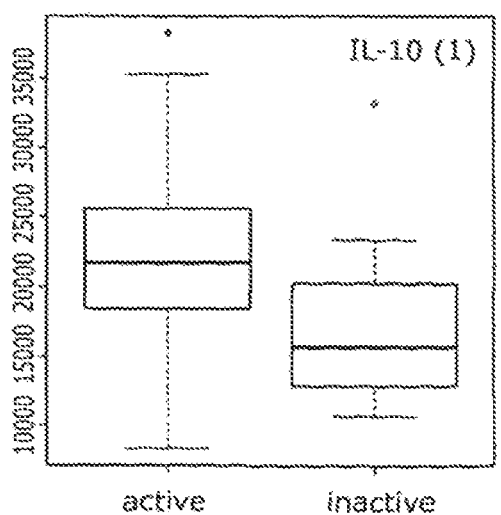
Fig. 18B(3)

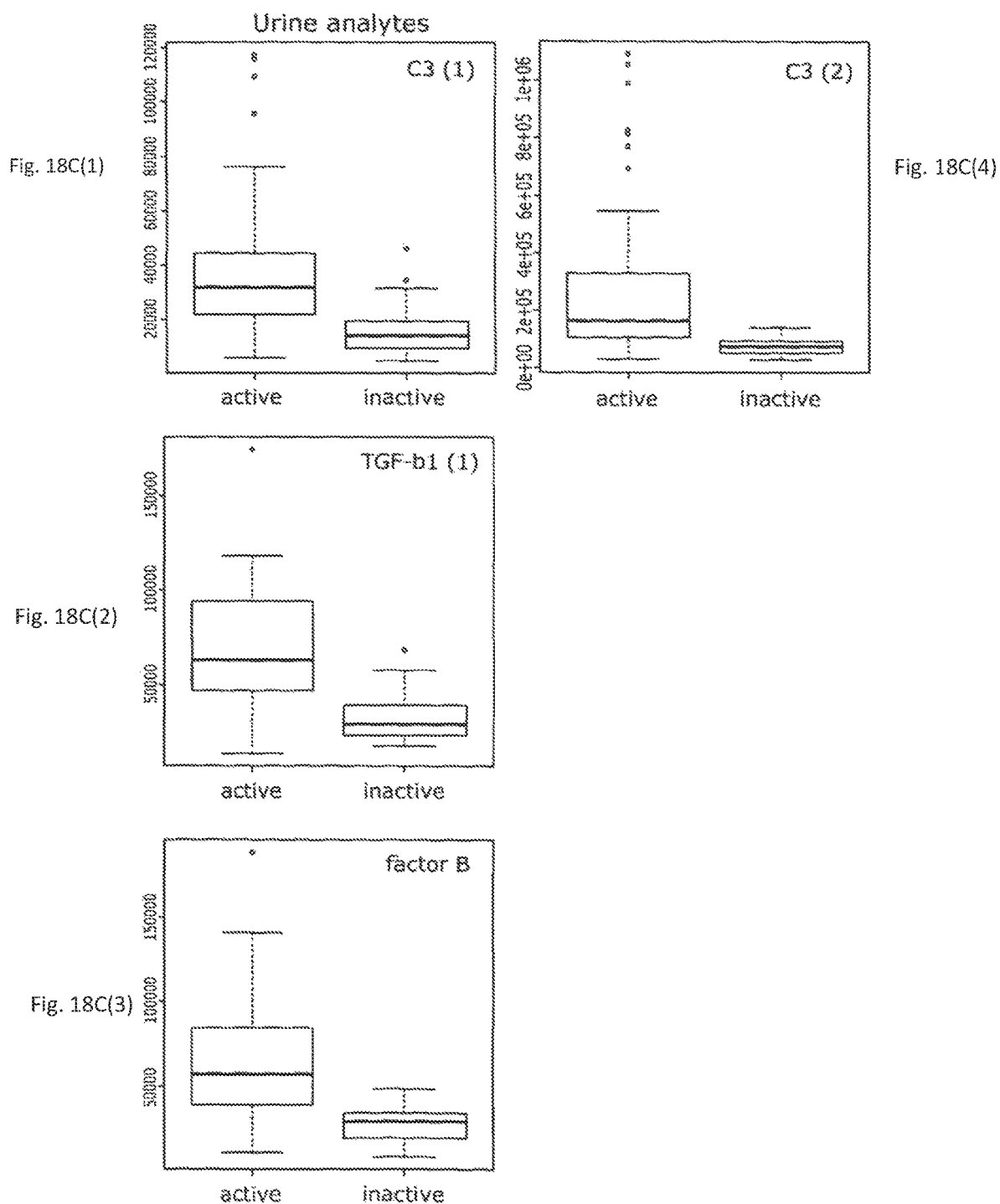

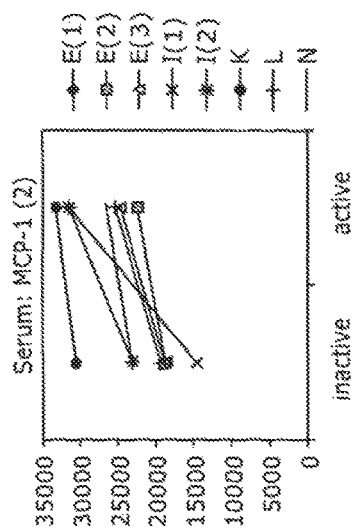
Fig. 19B(1)
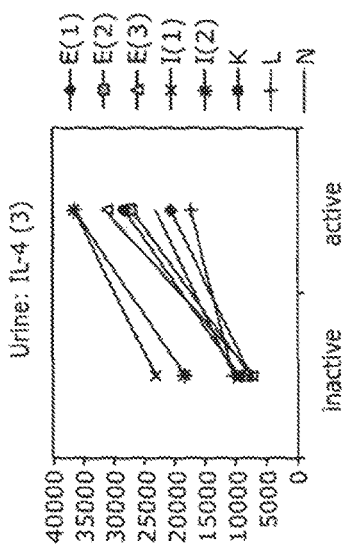
Fig. 19C(1)
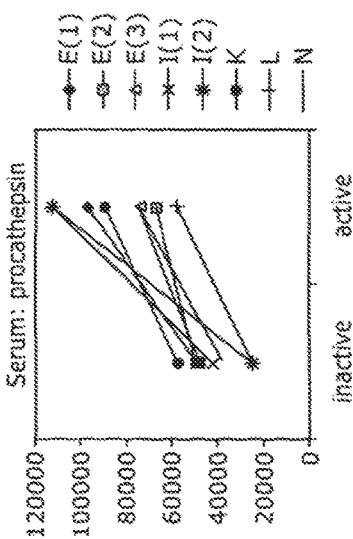
Fig. 19B(2)
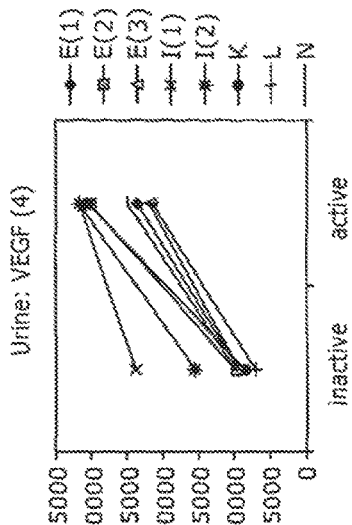
Fig. 19C(2)

BIOMARKER SIGNATURES AND USES THEREOF

The contents of each priority document listed in the accompanying Application Data Sheet is incorporated in its entirety by reference herein.

FIELD OF INVENTION

The present invention relates to biomarkers for the diagnosis, characterisation and prognosis of Systemic Lupus Erythematosus (SLE), as well as signatures and arrays thereof and methods for use of the same.

BACKGROUND

Systematic lupus erythematosus is a chronic, multisystem autoimmune disease with a broad range of possible clinical and serological presentations. It is characterized by a loss of tolerance to host antigens and development of pathogenic autoantibodies that damage target organs, such as skin, lungs, heart, joints, brain and kidney. SLE is estimated to worldwide affect 0.1% of the population, predominantly women between their 20s and early 40s. The pathogenesis of SLE is still largely unknown, although both genetic and environmental factors are probably involved in disease development. Establishing a diagnosis of lupus is difficult and relies on a list of eleven classification criteria that were developed over twenty years ago by the American College of Rheumatology (ACR). These classification criteria can guide the initial assessment of the patient with SLE but are not sufficient to adequately diagnose SLE, pin-point the phenotypic subclasses of SLE with high confidence, or to predict disease flares and remissions. The latter features are key criteria for optimizing the treatment of the diseases. In fact, there currently exist no multiplexed serum biomarker signatures able to resolve these key unmet clinical issues.

Hence, there is an urgent need to identify biomarkers that will improve diagnosis, classification and prognosis of SLE.

Against this background, the inventors have now developed a proteomic approach to determining a Systemic Lupus Erythematosus-associated disease state in a subject and have identified biomarkers for diagnosing, characterizing and prognosing Systemic Lupus Erythematosus.

SUMMARY OF THE INVENTION

Accordingly, in a first aspect the invention provides a method for determining a Systemic Lupus Erythematosus-associated disease state in a subject comprising the steps of:
  a) providing a sample to be tested; and
  b) measuring the presence and/or amount in the test sample of one or more biomarker(s) selected from the group defined in Table 1;
wherein the presence and/or amount in the test sample of the one or more biomarker(s) selected from the group defined in Table 1 is indicative of a Systemic Lupus Erythematosus-associated disease state.

Thus, the invention provides protein signatures for determining a Systemic Lupus Erythematosus-associated disease state in a subject.

By "protein signature" we include the meaning of a combination of the presence and/or amount of serum proteins present in an individual having SLE and which can be distinguished from a combination of the presence and/or amount of serum proteins present in an individual not afflicted with SLE, i.e. a normal, or healthy, individual.

By "Systemic Lupus Erythematosus-associated disease state" we include the diagnosis, prognosis and/or characterisation of phenotypic subtype of SLE in the subject.

Preferably, the individual is a human, but may be any mammal such as a domesticated mammal (preferably of agricultural or commercial significance including a horse, pig, cow, sheep, dog and cat).

In one embodiment, the method further comprises the steps of:
  c) providing a control sample from an individual with a different Systemic Lupus Erythematosus-associated disease state to the test subject; and
  d) measuring the presence and/or amount in the control sample of the one or more biomarkers measured in step (b);
wherein the Systemic Lupus Erythematosus-associated disease state is identified in the event that the presence and/or amount in the test sample of the one or more proteins measured in step (b) is different from the presence and/or amount in the control sample.

In one embodiment, step (b) comprises or consists of measuring the presence and/or amount in the test sample of one or more of the biomarkers defined in Table 1A, for example, two of the biomarkers defined in Table 1A.

Hence, in one embodiment, step (b) comprises or consists of measuring the presence and/or amount in the test sample of Glucagon like peptide-1 (GLP-1). Alternatively or additionally, step (b) comprises or consists of measuring the presence and/or amount in the test sample of Procathepsin W. Alternatively or additionally, step (b) comprises or consists of measuring the presence and/or amount in the test sample of Angiomotin. Alternatively or additionally, step (b) comprises or consists of measuring the presence and/or amount in the test sample of C1 esterase inhibitor. Alternatively or additionally, step (b) comprises or consists of measuring the presence and/or amount in the test sample of C1q. Alternatively or additionally, step (b) comprises or consists of measuring the presence and/or amount in the test sample of C1 s. Alternatively or additionally, step (b) comprises or consists of measuring the presence and/or amount in the test sample of C3. Alternatively or additionally, step (b) comprises or consists of measuring the presence and/or amount in the test sample of C4. Alternatively or additionally, step (b) comprises or consists of measuring the presence and/or amount in the test sample of C5. Alternatively or additionally, step (b) comprises or consists of measuring the presence and/or amount in the test sample of CD40. Alternatively or additionally, step (b) comprises or consists of measuring the presence and/or amount in the test sample of Eotaxin. Alternatively or additionally, step (b) comprises or consists of measuring the presence and/or amount in the test sample of Complement factor B (Factor B). Alternatively or additionally, step (b) comprises or consists of measuring the presence and/or amount in the test sample of IgM. Alternatively or additionally, step (b) comprises or consists of measuring the presence and/or amount in the test sample of IL-10. Alternatively or additionally, step (b) comprises or consists of measuring the presence and/or amount in the test sample of IL-11. Alternatively or additionally, step (b) comprises or consists of measuring the presence and/or amount in the test sample of IL-12. Alternatively or additionally, step (b) comprises or consists of measuring the presence and/or amount in the test sample of IL-13. Alternatively or additionally, step (b) comprises or consists of measuring the presence and/or amount in the test sample of IL-16. Alternatively or additionally, step (b) comprises or consists of measuring the presence and/or amount in the test sample of IL-18. Alternatively or additionally, step (b) comprises or consists of measuring the presence and/or amount in the test sample of IL-1a. Alternatively or additionally, step (b) comprises or consists of measuring the presence and/or amount in the test sample of IL-1-ra. Alternatively or additionally, step (b) comprises or consists of measuring the presence and/or amount in the test sample of IL-2. Alternatively or additionally, step (b) comprises or consists of measuring the presence and/or amount in the test sample of IL-3. Alternatively or additionally, step (b) comprises or consists of measuring the presence and/or amount in the test sample of IL-4. Alternatively or additionally, step (b) comprises or consists of measuring the presence and/or amount in the test sample of IL-5. Alternatively or additionally, step (b) comprises or consists of measuring the presence and/or amount in the test sample of IL-6. Alternatively or additionally, step (b) comprises or consists of measuring the presence and/or amount in the test sample of IFN-g. Alternatively or additionally, step (b) comprises or consists of measuring the presence and/or amount in the test sample of Integrin alfa-10. Alternatively or additionally, step (b) comprises or consists of measuring the presence and/or amount in the test sample of LDL. Alternatively or additionally, step (b) comprises or consists of measuring the presence and/or amount in the test sample of Leptin. Alternatively or additionally, step (b) comprises or consists of measuring the presence and/or amount in the test sample of Lewis x/CD15. Alternatively or additionally, step (b) comprises or consists of measuring the presence and/or amount in the test sample of Monocyte chemotactiv protein-1 (MCP-1). Alternatively or additionally, step (b) comprises or consists of measuring the presence and/or amount in the test sample of Mucine 1. Alternatively or additionally, step (b) comprises or consists of measuring the presence and/or amount in the test sample of RANTES. Alternatively or additionally, step (b) comprises or consists of measuring the presence and/or amount in the test sample of Sialo Lewis x. Alternatively or additionally, step (b) comprises or consists of measuring the presence and/or amount in the test sample of TGF-b. Alternatively or additionally, step (b) comprises or consists of measuring the presence and/or amount in the test sample of Tumor necrosis factor-alfa (TNF-a). Alternatively or additionally, step (b) comprises or consists of measuring the presence and/or amount in the test sample of VEGF. Alternatively or additionally, step (b) comprises or consists of measuring the presence and/or amount in the test sample of IFN-a. Alternatively or additionally, step (b) comprises or consists of measuring the presence and/or amount in the test sample of Monocyte chemotactiv protein-4 (MCP-4). Alternatively or additionally, step (b) comprises or consists of measuring the presence and/or amount in the test sample of Properdin. Alternatively or additionally, step (b) comprises or consists of measuring the presence and/or amount in the test sample of GM-CSF. Alternatively or additionally, step (b) comprises or consists of measuring the presence and/or amount in the test sample of IL-7. Alternatively or additionally, step (b) comprises or consists of measuring the presence and/or amount in the test sample of Integrin alfa-11.

Alternatively or additionally, step (b) comprises or consists of measuring the presence and/or amount in the test sample of TM peptide. Alternatively or additionally, step (b) comprises or consists of measuring the presence and/or amount in the test sample of Tumor necrosis factor beta (TNF-b). Alternatively or additionally, step (b) comprises or consists of measuring the presence and/or amount in the test sample of Tyrosine protein kinase JAK3. Alternatively or additionally, step (b) comprises or consists of measuring the presence and/or amount in the test sample of Tyrosine protein kinase BTK. Alternatively or additionally, step (b) comprises or consists of measuring the presence and/or amount in the test sample of IL-8. Alternatively or additionally, step (b) comprises or consists of measuring the presence and/or amount in the test sample of IL-1b. Alternatively or additionally, step (b) comprises or consists of measuring the presence and/or amount in the test sample of Monocyte chemotactiv protein-3 (MCP-3). Alternatively or additionally, step (b) comprises or consists of measuring the presence and/or amount in the test sample of IL-9. Alternatively or additionally, step (b) comprises or consists of measuring the presence and/or amount in the test sample of Glucagon like peptide-1 receptor (GLP-1 R). Alternatively or additionally, step (b) comprises or consists of measuring the presence and/or amount in the test sample of CD40 ligand (CD40-L). Alternatively or additionally, step (b) comprises or consists of measuring the presence and/or amount in the test sample of Lewis y. Alternatively or additionally, step (b) comprises or consists of measuring the presence and/or amount in the test sample of HLA-DR. Alternatively or additionally, step (b) comprises or consists of measuring the presence and/or amount in the test sample of ICAM-1. Alternatively or additionally, step (b) comprises or consists of measuring the presence and/or amount in the test sample of Ku 70/80.

In one embodiment, the biomarker mRNA and/or amino acid sequences correspond to those available on the GenBank database and natural variants thereof. In a further embodiment, the biomarker mRNA and/or amino acid sequences correspond to those available on the GenBank database on 7 Sep. 2010.

Generally, the Systemic Lupus Erythematosus-associated disease state in a subject is determined with an ROC AUC of at least 0.55, for example with an ROC AUC of at least, 0.60, 0.65, 0.70, 0.75, 0.80, 0.85, 0.90, 0.95, 0.96, 0.97, 0.98 or with an ROC AUC of at least 0.99. Preferably, the Systemic Lupus Erythematosus-associated disease state in an individual is determined with an ROC AUC of at least 0.85.

Typically, the Systemic Lupus Erythematosus-associated disease state in a subject is determined using a support vector machine (SVM), such as those available from http://cran.r-project.org/web/packages/e1071/index.html (e.g. e1071 1.5-24). However, any other suitable means may also be used.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training datapoints of any class (so-called functional margin), since in general the larger the margin the lower the generalization error of the classifier. For more information on SVMs, see for example, Burges, 1998, Data Mining and Knowledge Discovery, 2:121-167.

In one embodiment of the invention, the SVM is 'trained' prior to performing the methods of the invention using proteome samples from subjects assigned to known patient groups (namely, those patients in which the Systemic Lupus Erythematosus-associated disease state is present versus those patients in which it is absent). By running such training samples, the SVM is able to learn what biomarker profiles are associated with the Systemic Lupus Erythematosus-associated disease state. Once the training process is complete, the SVM is then able whether or not the proteome sample tested is from a subject a Systemic Lupus Erythematosus-associated disease state.

However, this training procedure can be by-passed by pre-programming the SVM with the necessary training parameters. For example, a Systemic Lupus Erythematosus-associated disease state in a subject can be determined using the SVM parameters detailed in Table 15, based on the measurement of some or all the biomarkers listed in Table 1.

It will be appreciated by skilled persons that suitable SVM parameters can be determined for any combination of the biomarkers listed Table 1 by training an SVM machine with the appropriate selection of data (i.e. biomarker measurements in proteome samples from known patient groups.

Preferably, the method of the invention has an accuracy of at least 75%, for example 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% accuracy.

Preferably, the method of the invention has a sensitivity of at least 75%, for example 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sensitivity.

Preferably, the method of the invention has a specificity of at least 75%, for example 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% specificity.

By "accuracy" we mean the proportion of correct outcomes of a method, by "sensitivity" we mean the proportion of all positive chemicals that are correctly classified as positives, and by "specificity" we mean the proportion of all negative chemicals that are correctly classified as negatives.

In one embodiment, step (b) comprises or consists of measuring the presence and/or amount in the test sample of one or more of the biomarkers defined in Table 1B, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37 or 38 of the biomarkers defined in Table 1B.

In one embodiment, step (b) comprises or consists of measuring the presence and/or amount in the test sample of one or more of the biomarkers defined in Table 10, for example, 2 or 3 of the biomarkers defined in Table 10.

In one embodiment, step (b) comprises or consists of measuring the presence and/or amount in the test sample of one or more of the biomarkers defined in Table 1D, for example, 2, 3, 4, 5, 6 or 7 of the biomarkers defined in Table 1D.

In one embodiment, step (b) comprises or consists of measuring the presence and/or amount in the test sample the biomarker defined in Table 1E.

In one embodiment, step (b) comprises or consists of measuring the presence and/or amount in the test sample of one or more of the biomarkers defined in Table 1F, for example, two of the biomarkers defined in Table 1F.

In one embodiment, step (b) comprises or consists of measuring the presence and/or amount in the test sample of one or more of the biomarkers defined in Table 1G, for example, two of the biomarkers defined in Table 1G.

In one embodiment, step (b) comprises or consists of measuring the presence and/or amount in the test sample of one or more of the biomarkers defined in Table 1H, for example, 2, 3 or 4 of the biomarkers defined in Table 1H.

In one embodiment, step (b) comprises or consists of measuring the presence and/or amount in the test sample of the biomarker defined in Table 1I.

In one preferred embodiment, the method is for diagnosing Systemic Lupus Erythematosus in an individual; wherein the presence and/or amount in the test sample of the one or more biomarker(s) selected from the group defined in Table 1 is indicative of whether the individual has Systemic Lupus Erythematosus. For example, step (b) may comprise or consist of measuring the presence and/or amount in the test sample of all of the biomarkers defined in Table 1A, Table 1B, Table 10, Table 1D, Table 1E and/or Table 1I.

By "diagnosing" we mean determining whether a subject is suffering from SLE. Conventional methods of diagnosing SLE are well known in the art.

The American College of Rheumatology established eleven criteria in 1982 (see Tan et al., 1982, The 1982 revised criteria for the classification of systemic lupus Erythematosus, *Arthritis. Rheum.*, 25:1271-7), which were revised in 1997 as a classificatory instrument to operationalise the definition of SLE in clinical trials (see Hochberg, 1997, Updating the American College of Rheumatology revised criteria for the classification of systemic lupus Erythematosus, *Arthritis. Rheum.*, 40:1725). For the purpose of identifying patients for clinical studies, a person is taken to have SLE if any 4 out of 11 symptoms are present simultaneously or serially on two separate occasions.

| Criterion | Definition |
| --- | --- |
| 1. Malar Rash | Fixed erythema, flat or raised, over the malar eminences, tending to spare the nasolabial folds |
| 2. Discoid rash | Erythematous raised patches with adherent keratotic scaling and follicular plugging; atrophic scarring may occur in older lesions |
| 3. Photosensitivity | Skin rash as a result of unusual reaction to sunlight, by patient history or physician observation |
| 4. Oral ulcers | Oral or nasopharyngeal ulceration, usually painless, observed by physician |
| 5. Nonerosive Arthritis | Involving 2 or more peripheral joints, characterized by tenderness, swelling, or effusion |
| 6. Pleuritis or Pericarditis | Pleuritis--convincing history of pleuritic pain or rubbing heard by a physician or evidence of pleural effusion OR Pericarditis--documented by electrocardiogram or rub or evidence of pericardial effusion |
| 7. Renal Disorder | Persistent proteinuria > 0.5 grams per day or > than 3+ if quantitation not performed OR Cellular casts--may be red cell, hemoglobin, granular, tubular, or mixed |
| 8. Neurologic Disorder | Seizures in the absence of offending drugs or known metabolic derangements; e.g., uremia, ketoacidosis, or electrolyte imbalance OR Psychosis in the absence of offending drugs or known metabolic derangements, e.g., uremia, ketoacidosis, or electrolyte imbalance |

-continued

| Criterion | Definition |
| --- | --- |
| 9. Hematologic Disorder | Hemolytic anemia--with reticulocytosis OR Leukopenia--<4,000/mm3 on ≥2 occasions OR Lyphopenia--<1,500/mm3 on ≥2 occasions OR Thrombocytopenia--<100,000/mm3 in the absence of offending drugs |
| 10. Immunologic Disorder | Anti-DNA: antibody to native DNA in abnormal titer OR Anti-Sm: presence of antibody to Sm nuclear antigen OR Positive finding of antiphospholipid antibodies on: (a) an abnormal serum level of IgG or IgM anticardiolipin antibodies, (b) a positive test result for lupus anticoagulant using a standard method, or (c) a false-positive test result for at least 6 months confirmed by Treponema pallidum immobilization or fluorescent treponemal antibody absorption test |
| 11. Antinuclear Antibody | An abnormal titer of antinuclear antibody by immunofluorescence or an equivalent assay at any point in time and in the absence of drugs |

Some people, especially those with antiphospholipid syndrome, may have SLE without four of the above criteria, and also SLE may present with features other than those listed in the criteria (see Asherson et al., 2003, Catastrophic antiphospholipid syndrome: international consensus statement on classification criteria and treatment guidelines, *Lupus*, 12(7): 530-4; Sangle et al., 2005, Livedo *reticularis* and pregnancy morbidity in patients negative for antiphospholipid antibodies, *Ann. Rheum. Dis.*, 64(1):147-8; and Hughes and Khamashta, 2003, Seronegative antiphospholipid syndrome, *Ann. Rheum. Dis.*, 62(12):1127).

Recursive partitioning has been used to identify more parsimonious criteria (see Edworthy et al., 1988, Analysis of the 1982 ARA lupus criteria data set by recursive partitioning methodology: new insights into the relative merit of individual criteria, *J. Rheumatol.*, 15(10):1493-8). This analysis presented two diagnostic classification trees:
Simplest classification tree: SLE is diagnosed if a person has an immunologic disorder (anti-DNA antibody, anti-Smith antibody, false positive syphilis test, or LE cells) or malar rash.
Full classification tree: Uses 6 criteria.

Other alternative set of criteria has been suggested, the St. Thomas' Hospital "alternative" criteria in 1998 (see Hughes, 1998, Is it lupus? The St. Thomas' Hospital "alternative" criteria, *Clin. Exp. Rheumatol.*, 16(3):250-2).

However, these criteria were not intended to be used to diagnose individuals. They are time-consuming, subjective, require a high degree of experience to use effectively and have a high frequency of excluding actual SLE sufferers (i.e., diagnosing SLE patients as non-SLE patients). The present invention addresses these problems, providing objective SLE diagnosis.

In a further preferred embodiment, the method is for characterising Systemic Lupus Erythematosus in an individual; wherein the presence and/or amount in the test sample of the one or more biomarker(s) selected from the group defined in Table 1 is indicative of whether the individual has Systemic Lupus Erythematosus, subtype 1, subtype 2 or subtype 3. For example, step (b) may comprise or consist of measuring the presence and/or amount in the test sample of all of the biomarkers defined in Table 1A, Table 1B, Table 10, Table 1D, Table 1F and/or Table 1I.

By "characterising" or "classifying" we include determining the phenotypic subtype of SLE in a subject. SLE1 comprises skin and musculoskeletal involvement but lacks serositis, systemic vasculitis and kidney involvement. SLE2 comprises skin and musculoskeletal involvement, serositis and systemic vasculitis but lacks kidney involvement. SLE3 comprises skin and musculoskeletal involvement, serositis, systemic vasculitis and SLE glomerulonephritis. SLE1, SLE2 and SLE3 represent mild, moderate and severe SLE disease states respectively.

In a further preferred embodiment, the method is for prognosing Systemic Lupus Erythematosus in an individual; wherein the sample to be tested in step (b) is a blood or serum sample and wherein the presence and/or amount in the test sample of the one or more biomarker(s) selected from the group defined in Table 1 is indicative of the prognosis of the Systemic Lupus Erythematosus in the individual. For example, step (b) may comprise or consist of measuring the presence and/or amount in the test sample of all of the biomarkers defined in Table 1A, Table 1B, Table 10, Table 1E, Table 1F and/or Table 1G.

By "prognosis" we include the act or process of predicting the severity and/or probable course and outcome of SLE in a subject, e.g. determining survival probability. SLE disease severity and progression are conventionally determined through a clinical assessment and scoring using the following (SLEDAI) criteria (see Bombardier et al., 1992, *Arthritis Rheum.*, 35(6):630-40):

| Wt | Descriptor | Definition |
| --- | --- | --- |
| 8 | Seizure | Recent onset. Exclude metabolic, infectious or drug cause. |
| 8 | Psychosis | Altered ability to function in normal activity due to severe disturbance in the perception of reality. Include hallucinations, incoherence, marked loose associations, impoverished thought content, marked illogical thinking, bizarre, disorganized, or catatonic behaviour. Excluded uraemia and drug causes. |
| 8 | Organic Brain Syndrome | Altered mental function with impaired orientation, memory or other intelligent function, with rapid onset fluctuating clinical features. Include clouding of consciousness with reduced capacity to focus, and inability to sustain attention to environment, plus at least two of the following: perceptual disturbance, incoherent speech, insomnia or daytime drowsiness, or increased or decreased psychomotor activity. Exclude metabolic, infectious or drug causes. |
| 8 | Visual Disturbance | Retinal changes of SLE. Include cytoid bodies, retinal hemorrhages, serious exodate or hemorrhages in the choroids, or optic neuritis. Exclude hypertension, infection, or drug causes. |

-continued

| Wt | Descriptor | Definition |
|---|---|---|
| 8 | Cranial Nerve Disorder | New onset of sensory or motor neuropathy involving cranial nerves. |
| 8 | Lupus Headache | Severe persistent headache: may be migrainous, but must be non-responsive to narcotic analgesia. |
| 8 | CVA | New onset of cerebrovascular accident(s). Exclude arteriosclerosis. |
| 8 | Vasculitis | Ulceration, gangrene, tender finger nodules, periungual, infarction, splinter hemorrhages, or biopsy or angiogram proof of vasculitis. |
| 4 | Arthritis | More than 2 joints with pain and signs of inflammation (i.e. tenderness, swelling, or effusion). |
| 4 | Myositis | Proximal muscle aching/weakness, associated with elevated creatine phosphokinase/adolase or electromyogram changes or a biopsy showing myositis. |
| 4 | Urinary Casts | Heme-granular or red blood cell casts. |
| 4 | Hematuria | >5 red blood cells/high power field. Exclude stone, infection or other cause. |
| 4 | Proteinuria | >0.5 gm/24 hours. New onset or recent increase of more than 0.5 gm/24 hours. |
| 4 | Pyuria | >5 white blood cells/high power field. Exclude infection. |
| 2 | New Rash | New onset or recurrence of inflammatory type rash. |
| 2 | Alopecia | New onset or recurrence of abnormal, patchy or diffuse loss of hair. |
| 2 | Mucosal Ulcers | New onset or recurrence of oral or nasal ulcerations. |
| 2 | Pleurisy | Pleuritic chest pain with pleural rub or effusion, or pleural thickening. |
| 2 | Pericarditis | Pericardial pain with at least one of the following: rub, effusion, or electrocardiogram confirmation. |
| 2 | Low Complement | Decrease in CH50, C3, or C4 below the lower limit of normal for testing laboratory. |
| 2 | Increased DNA binding | >25% binding by Fan assay or above normal range for testing laboratory. |
| 1 | Fever | >38° C. Exclude infectious cause |
| 1 | Thrombocytopenia | <l00,000 platelets/mm3 |
| 1 | Leukopenia | <3,000 White blood cell/mm3. Exclude drug causes. |

The corresponding score/weight is applied if a descriptor is present at the time of visit or in the proceeding 10 days. The score is then totalled. A skilled person will appreciate that the SLEDAI boundaries of low, mid and high severity SLE may vary according to the patient group being assessed.

Thus, in one embodiment the lower range for low severity SLE may be any one of 1, 2, 3, 4, 5, 6, 7, 8, 9, 10, 11, 12, 13, 14, 15, 16, 17, 18, 19 or 20; the upper range for low severity SLE may be any one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45; the lower range for mid severity SLE may be any one of 5, 6, 7, 8, 9, 10, 11, 12, 13, 14, 15, 16, 17, 18, 19 or 20; the upper range for mid severity SLE may be any one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85; the lower range for high severity SLE may be any one of 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95; the upper range for high severity SLE may be any one of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 105 or 105; with the provisos that the lower range of a particular severity level must be of a lower score than its higher range and the ranges of each severity level may not overlap.

However, in one embodiment a total SLEDAI score of 3-6 indicates low severity SLE, a score of 9-19 indicates mid-severity SLE and a score of 22-34 indicates high severity SLE. In a further embodiment a total SLEDAI score of 1-6 indicates low severity SLE, a score of 7-20 indicates mid-severity SLE and a score of indicates high severity SLE.

An increase in SLEDAI score of >3 from the previous assessment indicates mild or moderate flare. An increase in SLEDAI score of >12 from the previous assessment indicates severe flare. A decrease in SLEDAI score of >3 from the previous assessment indicates mild or moderate remission. A decrease in SLEDAI score of >12 from the previous assessment indicates advanced remission. An increase or decrease in SLEDAI score of 3 indicates stable (neither flaring nor non-flaring) SLE.

However, as for SLE diagnostic criteria, the assessment of the SLEDAI criteria is time-consuming, highly subjective and requires a high degree of experience to perform effectively. The present invention addresses these problems, providing objective analysis of disease activity, allowing an equivalent SLEDAI score and/or an equivalent change in SLEDAI score over time (for example, in the previous 10 days) to be attributed to the subject being tested.

In one embodiment, the method is for prognosing Systemic Lupus Erythematosus in an individual; the sample to be tested in step (b) is a urine sample; and the presence and/or amount in the test sample of the one or more biomarker(s) selected from the group defined in Table 1 is indicative of the prognosis of the Systemic Lupus Erythematosus in the individual. For example, step (b) may comprise or consist of measuring the presence and/or amount in the test sample of all of the biomarkers defined in Table 1A, Table 1B, Table 1D, Table 1E, Table 1F, Table 1G and/or Table 1H.

In one embodiment, the control sample of step (c) is provided from a healthy individual or an individual with Systemic Lupus Erythematosus.

For example, the control sample of step (c) may be provided from an individual with:
(i) active (i.e. flaring) Systemic Lupus Erythematosus (i.e. increase of >3 in SLEDAI score from previous assessment (or in previous 10 days));
(ii) moderate (i.e. neither flaring nor non-flaring; no change in SLEDAI score of >3 from previous assessment (or in previous 10 days)) Systemic Lupus Erythematosus; and/or
(iii) passive/remissive (i.e. non-flaring; decrease of >3 in SLEDAI score from previous assessment (or in previous 10 days)) Systemic Lupus Erythematosus.

The control sample of step (c) may be provided from an individual with Systemic Lupus Erythematosus subtype 1 (SLE-1), Systemic Lupus Erythematosus subtype 2 (SLE-2) or Systemic Lupus Erythematosus subtype 3 (SLE-3).

In one embodiment, step (b) and/or step (d) is performed using a first binding agent capable of binding to the one or more biomarker(s).

Binding agents (also referred to as binding molecules) can be selected from a library, based on their ability to bind a given motif, as discussed below.

In one embodiment, the first binding agent is an antibody or a fragment thereof.

Thus, a fragment may contain one or more of the variable heavy ($V_H$) or variable light ($V_L$) domains. For example, the term antibody fragment includes Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544).

The term "antibody variant" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

A general review of the techniques involved in the synthesis of antibody fragments which retain their specific binding sites is to be found in Winter & Milstein (1991) Nature 349, 293-299.

Additionally or alternatively at least one type, more typically all of the types, of the binding molecules is an aptamer.

Molecular libraries such as antibody libraries (Clackson et al, 1991, Nature 352, 624-628; Marks et al, 1991, J Mol Biol 222(3): 581-97), peptide libraries (Smith, 1985, Science 228(4705): 1315-7), expressed cDNA libraries (Santi et al (2000) J Mol Biol 296(2): 497-508), libraries on other scaffolds than the antibody framework such as affibodies (Gunneriusson et al, 1999, Appl Environ Microbiol 65(9): 4134-40) or libraries based on aptamers (Kenan et al, 1999, Methods Mol Biol 118, 217-31) may be used as a source from which binding molecules that are specific for a given motif are selected for use in the methods of the invention.

The molecular libraries may be expressed in vivo in prokaryotic (Clackson et al, 1991, op. cit.; Marks et al, 1991, op. cit.) or eukaryotic cells (Kieke et al, 1999, Proc Natl Acad Sci USA, 96(10):5651-6) or may be expressed in vitro without involvement of cells (Hanes & Pluckthun, 1997, Proc Natl Acad Sci USA 94(10):4937-42; He & Taussig, 1997, Nucleic Acids Res 25(24):5132-4; Nemoto et al, 1997, FEBS Lett, 414(2):405-8).

In cases when protein based libraries are used often the genes encoding the libraries of potential binding molecules are packaged in viruses and the potential binding molecule is displayed at the surface of the virus (Clackson et al, 1991, op. cit.; Marks et al, 1991, op. cit; Smith, 1985, op. cit.).

The most commonly used such system today is filamentous bacteriophage displaying antibody fragments at their surfaces, the antibody fragments being expressed as a fusion to the minor coat protein of the bacteriophage (Clackson et al, 1991, op. cit.; Marks et al, 1991, op. cit). However, also other systems for display using other viruses (EP 39578), bacteria (Gunneriusson et al, 1999, op. cit.; Daugherty et al, 1998, Protein Eng 11(9):825-32; Daugherty et al, 1999, Protein Eng 12(7):613-21), and yeast (Shusta et al, 1999, J Mol Biol 292(5):949-56) have been used.

In addition, recently, display systems utilising linkage of the polypeptide product to its encoding mRNA in so called ribosome display systems (Hanes & Pluckthun, 1997, op. cit.; He & Taussig, 1997, op. cit.; Nemoto et al, 1997, op. cit.), or alternatively linkage of the polypeptide product to the encoding DNA (see U.S. Pat. No. 5,856,090 and WO 98/37186) have been presented.

When potential binding molecules are selected from libraries one or a few selector peptides having defined motifs are usually employed. Amino acid residues that provide structure, decreasing flexibility in the peptide or charged, polar or hydrophobic side chains allowing interaction with the binding molecule may be used in the design of motifs for selector peptides. For example—
(i) Proline may stabilise a peptide structure as its side chain is bound both to the alpha carbon as well as the nitrogen;
(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically selection of binding molecules may involve the use of array technologies and systems to analyse binding to spots corresponding to types of binding molecules.

In one embodiment, the antibody or fragment thereof is a recombinant antibody or fragment thereof (such as an scFv)

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

In one embodiment, the antibody or fragment thereof is selected from the group consisting of: scFv; Fab; a binding domain of an immunoglobulin molecule.

In one embodiment, the one or more biomarker(s) in the test sample is labelled with a detectable moiety.

In one embodiment, the one or more biomarker(s) in the control sample is labelled with a detectable moiety (which may be the same or different from the detectable moiety used to label the test sample).

By a "detectable moiety" we include the meaning that the moiety is one which may be detected and the relative amount and/or location of the moiety (for example, the location on an array) determined.

Detectable moieties are well known in the art.

A detectable moiety may be a fluorescent and/or luminescent and/or chemiluminescent moiety which, when exposed to specific conditions, may be detected. For example, a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

Alternatively, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, 19F, $^{13}$C, $^{15}$N, $^{17}$O, gadolinium, manganese or iron. Clearly, the agent to be detected (such as, for example, the one or more proteins in the test sample and/or control sample described herein and/or an antibody molecule for use in detecting a selected protein) must have sufficient of the appropriate atomic isotopes in order for the detectable moiety to be readily detectable.

The radio- or other labels may be incorporated into the agents of the invention (i.e. the proteins present in the samples of the methods of the invention and/or the binding agents of the invention) in known ways. For example, if the binding moiety is a polypeptide it may be biosynthesised or may be synthesised by chemical amino acid synthesis using suitable amino acid precursors involving, for example, fluorine-19 in place of hydrogen. Labels such as 99mTc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

Preferably, the detectable moiety is selected from the group consisting of: a fluorescent moiety, a luminescent moiety, a chemiluminescent moiety, a radioactive moiety, and an enzymatic moiety.

In one embodiment, step (b) is performed using an array.

In one embodiment, step (d) is performed using an array.

For example, the array may be a bead-based array or a surface-based array.

In one embodiment, the array is selected from the group consisting of macroarrays, microarrays and nanoarrays.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. By using well-known techniques, such as contact or non-contact printing, masking or photolithography, the location of each spot can be defined. For reviews see Jenkins, R. E., Pennington, S. R. (2001, *Proteomics*, 2, 13-29) and Lal et al (2002, *Drug Discov Today* 15; 7(18 Suppl):S143-9).

Typically, the array is a microarray. By "microarray" we include the meaning of an array of regions having a density of discrete regions of at least about 100/cm$^2$, and preferably at least about 1000/cm$^2$. The regions in a microarray have typical dimensions, e.g., diameters, in the range of between about 10-250 µm, and are separated from other regions in the array by about the same distance. The array may also be a macroarray or a nanoarray.

Once suitable binding molecules (discussed above) have been identified and isolated, the skilled person can manufacture an array using methods well known in the art of molecular biology.

In one embodiment, step (b) is performed using an assay comprising a second binding agent capable of binding to the one or more proteins, the second binding agent having a detectable moiety.

In one embodiment, step (d) is performed using an assay comprising a second binding agent capable of binding to the one or more proteins, the second binding agent having a detectable moiety.

In one embodiment, the second binding agent is an antibody or a fragment thereof (for example, as described above in relation to the first binding agent).

Typically, the assay is an ELISA (Enzyme Linked Immunosorbent Assay) which typically involve the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is also employed used since this can readily be detected by its reaction with enzyme-linked avidin or streptavidin to which it binds with great specificity and affinity.

It will be appreciated by persons skilled in the art that there is a degree of fluidity in the biomarker composition of the signatures of the invention. Thus, different combinations of the biomarkers may be equally useful in the diagnosis, prognosis and/or characterisation of SLE. In this way, each biomarker (either alone or in combination with one or more other biomarkers) makes a contribution to the signature.

In one embodiment, step (b) comprises or consists of measuring the presence and/or amount in the test sample of C1s, C5, GLP-1, IL-10, IL-12, IL-18, IL-1a, IL-3, IL-5, IL-8, INF-gamma, LDL, procathepsin and TNF-alpha.

In one embodiment, step (b) comprises or consists of measuring the presence and/or amount in the test sample of C3, C4, CD40, GLP-1, IL-12, IL-13, IL-1a, IL-3, Procathepsin, Properdin, TGF-beta1, TNF-alpha and VEGF.

In one embodiment, step (b) comprises or consists of measuring the presence and/or amount in the test sample of the biomarkers listed in Table 2A, Table 2B, Table 2C, Table 2D, Table 2E, Table 2F, Table 2G, Table 2H, Table 21, Table 2J and Table 2K.

In one embodiment, step (b) comprises or consists of measuring the presence and/or amount in the test sample of the biomarkers listed in Table 3A, Table 3B, Table 3C, Table 3D, Table 3E, Table 3F, Table 3G, Table 3H, Table 31, Table 3J, Table 3K, Table 3L, Table 3M, Table 3N, Table 3O, Table 3P, Table 3Q, Table 3R, Table 3S or Table 3T.

In one embodiment, step (b) comprises or consists of measuring the presence and/or amount in the test sample of the biomarkers listed in Table 4A, Table 4B Table 4C or Table 4D.

A second aspect of the invention provides an array for determining a Systemic Lupus Erythematosus-associated disease state in an individual comprising one or more binding agent as defined above in relation to the first aspect of the invention.

In one embodiment, the array is for use in a method according to the first aspect of the invention.

In another embodiment the array is for determining a disease state defined in the first aspect of the invention comprising or consisting of measuring the presence and/or amount of a corresponding biomarker or group of biomarkers defined in the first aspect of the invention.

In a further embodiment the array is an array defined in the first aspect of the invention.

In one embodiment, the one or more binding agent is capable of binding to all of the proteins defined in Table 1.

A third aspect of the invention provides the use of one or more biomarkers selected from the group defined in Table 1 as a biomarker for determining a Systemic Lupus Erythematosus-associated disease state in an individual.

In one embodiment, all of the biomarkers defined in Table 1 are used as a biomarker for determining a Systemic Lupus Erythematosus-associated disease state in an individual.

A third aspect of the invention provides a kit for determining a Systemic Lupus Erythematosus-associated disease state in an individual comprising:
i) one or more first binding agent as defined above in relation to the first aspect of the invention; and
ii) instructions for performing the method of the first aspect of the invention.

BRIEF DESCRIPTION OF THE DRAWINGS

Preferred, non-limiting examples which embody certain aspects of the invention will now be described with reference to the following tables and figures:

FIGS. 1A(1)-1A(3) depict expression profiling of serum proteomes for classification of healthy controls vs. SSc patients.

FIGS. 1B(1)-1B(3) depict expression profiling of serum proteomes for classification of healthy controls vs. SLE patients.

FIGS. 1C(1)-1C(3) depict expression profiling of serum proteomes for classification of SSc vs. SLE patients.

FIGS. 3A(1)-3A(2) depict expression profiling of serum proteomes for classification of SLE1 vs. control patients.

FIGS. 3B(1)-3B(2) depict expression profiling of serum proteomes for classification of SLE2 vs. control patients.

FIGS. 3C(1)-3C(3) depict expression profiling of serum proteomes for classification of SLE3 vs. control patients.

FIGS. 4A(1)-4A(2) depict expression profiling of serum proteomes for classification of SLE1 vs. SSc patients.

FIGS. 4B(1)-4B(2) depict expression profiling of serum proteomes for classification of SLE2 vs. SSc patients.

FIGS. 4C(1)-4C(3) depict expression profiling of serum proteomes for classification of SLE3 vs. SSc patients.

FIGS. 5D(1)-5D(6) depict boxplots of microarray signal intensities for key cytokines.

FIGS. 7A-7C depict expression profiling of subsets of SLE3 reflecting disease activity using a 135 recombinant antibody microarray.

FIG. 11A depicts a receiver operator curve for patients with active SLE vs. healthy control patients.

FIGS. 11B(1)-11B(2) depict classification of the serum samples using SVM prediction values.

FIGS. 11C(1)-11C(2) depict a receiver operator curve for patients with inactive SLE vs. healthy control patients.

FIG. 11D depicts classification of SLE serum samples from remission time.

FIG. 13A depicts a receiver operator curve for SLE1 subgroup vs. SLE3.

FIGS. 13B(1)-13B(2) depict classification of serum samples using SVM prediction values and two-way hierarchial cluster analysis of 6 differentially expressed analytes.

FIGS. 17A(1)-17A(2) depict a receiver operator curve and classification based on SVM decision values for serum samples.

FIGS. 17B(1)-17B(2) depict a receiver operator curve and classification based on SVM decision values for urine samples.

FIGS. 18B(1)-18B(3) depict box plots of signal intensities of three serum analytes.

FIGS. 18C(1)-18C(4) depict box plots of signal intensities of three urine analytes.

FIGS. 19B(1)-19B(2) depict signal intensities of the top two ranked serum analytes.

FIGS. 19C(1)-19C(2) depict signal intensities of the top two ranked urine analytes.

FIG. 1—Expression profiling of serum proteomes from SSc and SLE using a 135 recombinant antibody microarray. The samples were classified using a leave-one-out cross validation approach with a SVM, and illustrated as ROC curves. Differentially expressed analytes are shown in heat maps, green—down-regulated, red—up-regulated, and black—equal levels. A) Classification of healthy controls vs. SSc. Four differentially expressed analytes, recognized by 5 antibodies, were identified. B) Classification of healthy controls vs. SLE. Forty non-redundant differentially expressed analytes, recognized by 58 antibodies were identified, of which the 25 highest ranked, i.e. significantly differentially expressed (p-values), analytes are shown. C) Classification of SSc. vs. SLE. Forty-two non-redundant differentially expressed analytes, recognized by 62 antibodies were identified, of which the 25 highest ranked analytes (p-values) are shown.

FIG. 2—Expression profiling of serum proteomes from clinical subsets of SSc, dcSSc and lcSSc, using a 135 recombinant antibody microarray. A) Classification of dcSSc and lcSSc vs. healthy controls based on all 135 antibodies, using a SVM-based leave-one-out cross validation test, expressed in terms of AUC values. AUC values obtained when using only significantly differentially expressed analytes are given within brackets. B) Significantly differentially expressed analytes are shown in a heat map. Seven differentially expressed analytes, recognized by 7 antibodies were identified for dcSSc vs. controls; 5 analytes, recognized by 5 antibodies for lcSSc vs. controls; while none were observed for dcSSc vs. lcSSc. Green—down-regulated, red—up-regulated, and black—equal levels.

FIG. 3—Expression profiling of phenotypic subsets of SLE reflecting increased disease severity, including SLE1 (least symptoms), SLE2, and SLE3 (most severe symptoms), using a 135 recombinant antibody microarray. The samples were classified using a leave-one-out cross validation approach with a SVM, and illustrated as ROC curves. Differentially expressed analytes are shown in heat maps, green—down-regulated, red—up-regulated, and black—equal levels. A) Classification of SLE1 vs. controls. B) Classification of SLE2 vs. controls. C) Classification of SLE3 vs. controls. The top 25 highest ranked, i.e. significantly differentially expressed (p-values), analytes are shown. D) Fifteen significantly differentially expressed analytes, recognized by 17 antibodies, were identified for SLE1 vs. controls; 29 analytes, recognized by 36 antibodies for SLE2 vs. controls; and 44 analytes recognized by 72 antibodies for SLE3 vs. controls.

FIG. 4—Expression profiling of phenotypic subsets of SLE reflecting increased disease severity and SSc, using a 135 recombinant antibody microarray. The samples were classified using a leave-one-out cross validation approach with a SVM, and illustrated as ROC curves. Differentially expressed analytes are shown in heat maps, green—down-regulated, red—up-regulated, and black—equal levels. A) Classification of SLE1 vs. SSc. B) Classification of SLE2 vs. SSc. C) Classification of SLE3 vs. SSc. The top 25 highest ranked, i.e. significantly differentially expressed (p-values), analytes are shown. D) Three significantly differentially expressed analytes, recognized by 3 antibodies, were identified for SLE1 vs. SSc; 36 analytes, recognized by 47 antibodies for SLE2 vs. SSc; and 49 analytes recognized by 79 antibodies for SLE3 vs. SSc.

FIG. 5—Expression profiling of phenotypic subsets of SLE reflecting increased disease severity, using a 135 recombinant antibody microarray. A) Classification of SLE1, SLE2 and SLE3 based on all 135 antibodies, using a SVM-based leave-one-out cross validation test, expressed in terms of AUC values. AUC values obtained when using only significantly differentially expressed analytes are given within brackets. B) PCA analysis of SLE1, SLE2, and SLE3 based on the top 13 significantly differentially antibodies using Qlucore. C) Significantly differentially expressed analytes are shown in a heat map. Twenty-three differentially expressed analytes, recognized by 28 antibodies, were identified for SLE1 vs. SLE2; 7 analytes, recognized by 8 antibodies for SLE2 vs. SLE3; and 32 analytes recognized by 47 antibodies for SLE1 vs. SLE3. Green—down-regulated, red—up-regulated, and black—equal levels. D) Microarray signal intensities observed for key Th1 (IL-2, IL-12, and IFN-γ) and Th2 (IL-4, and IL-10) cytokines shown as boxplots. The median values are indicated (thick line) and the hinges represent the 25th percentile and the 75th percentile, respectively.

FIG. 6—Expression profiling of subsets of SLE reflecting disease activity, using a 135 recombinant antibody microarray. A) Classification of SLE, grouped based solely on disease activity (SLEDAI values); low (3 to 6), mid (9 to 19) and high (22 to 34), based on all 135 antibodies, using a SVM-based leave-one-out cross validation test, expressed in terms of AUC values. AUC values obtained when using only significantly differentially expressed analytes are given within brackets. B) Significantly differentially expressed analytes are shown in a heat map. Twelve differentially expressed analytes, recognized by 14 antibodies, were identified for low vs. mid; 8 analytes, recognized by 12 antibodies for mid vs. high; and 10 analytes recognized by 16 antibodies for low vs. high. Green—down-regulated, red—up-regulated, and black—equal levels. C) Microarray signal intensities observed for complement proteins, including C1q, C3, C4, and C5, shown as boxplots. The median values are indicated (thick line) and the hinges represent the 25th percentile and the 75th percentile, respectively.

FIG. 7—Expression profiling of subsets of SLE3 reflecting disease activity, using a 135 recombinant antibody microarray. Classification of SLE3 subsets, grouped based on disease activity (SLEDAI values); SLE3 low (mean 13, range 10-16), SLE high (mean 24, range 17-32), based on all 135 antibodies, using a SVM-based leave-one-out cross validation test, expressed in terms of AUC values. The 20 signficantly differentially expressed analytes, recognized by 31 antibodies, are shown in a heat map. SSc. Green—down-regulated, red—up-regulated, and black—equal levels.

FIG. 8—A scanned representative microarray image of SLE sample used for spotting optimization protocol.

FIG. 9—Effect of different probe concentrations used for microarray fabrication on: (A) spot morphologies and (B) signal intensities. The signal intensities shown represent the mean value of eight replicates after substracting local background and negative control. The optimal concentration—combination between the best spot morphology and good signal intensity was chosen for each of the probes (underlined in the picture).

FIG. 10—A scanned microarray image for a SLE sample analyzed using recombinant antibody microarrays.

FIG. 11—Comparision of protein expression serum signatures from SLE patients with active (A-B) and inactive (C-D) stage of disease versus healthy subjects. (A) A receiver operator curve obtained for patients with active SLE (n=30) versus healthy controls (n=30) based on all 58 analytes, using a leave-one-out cross validation approach with a Support Vector Machine (SVM). (B) Classification of the serum samples using SVM prediction values and heat map showing hierachical clustering of 20 significantly differentialy expressed analytes. (C) ROC area obtained for patients with inactive SLE (n=30) versus healthy controls (n=30) (D) Classification of SLE serum samples from remission time using SVM and two-way hierarchical clustering of the 13 highest ranked analytes.

FIG. 12—Separation of patients from different SLE subgroups from healthy individuals. (A). A multidimensional plot based on 4 significant analytes (C1q, C4, VEGF (2), Procathepsin) representing the clear separation of SLE3 patients (green, n=10) from healthy subjects (blue, n=30). (B-C) Box plots demonstrating signal intensities observed for the most differentially expressed analytes: C1q and Procathepsin.

FIG. 13—Comparison of protein expression signatures from two cohorts of SLE patients, SLE1 subgroup vs SLE3. (A) ROC curve (B) Classification of the serum samples using SVM prediction values and two-way hierarchial cluster analysis of 6 significatly ($p<0.05$) differentaily expressed analytes.

FIG. 14—Correlation between serum levels of C1q, INF-α, TNF-α and IL-1α(2) with SLE activity.

FIG. 15—Spot morphology comparison: 1 drop.

FIG. 16—Representative scan images of serum flare sample (left) and urine flare sample (right).

FIG. 17—Classification of active versus inactive SLE nephritis using a leave-one-out cross validation with an SVM, based on all analytes and all samples. (A) Serum: ROC curve and classification based on SVM decision values. (B) Urine: ROC curve and classification based on SVM decision values.

FIG. 18—Using all samples. (A) Table 4 shows significant analytes in serum ($p<0.05$) and urine ($p<0.001$) based on a Wilcoxon test. Non-significant analytes in both serum and urine are not shown. (B) Box-plots showing signal intensities of three serum analytes displaying the lowest p-values: C1q p=0.000015, LDL(2) p=0.00026, IL-10(1) p=0.0020. (C) Box-plots showing signal intensities of three urine analytes displaying the lowest p-values: C3(1) p=0.000011, C3(2) p=0.000022, TGF-b1(1) p=0.000035, factor B p=0.000045. Interpretation of box-plots: mid line: median intensity, box: central 50 percent, whiskers: extent to a maximum of 1.5 times the interquartile, dots: any extreme values outside the whiskers.

FIG. 19—Biomarkers in individually paired samples. (A) Table 5 shows significant analytes in serum ($p<0.05$) and urine ($p<0.001$) based on paired t-tests. (B) Signal intensities of the two top ranked analytes in serum: procathepsin p=0.0011, MCP-1(2) p=0.0047. (C) Signal intensities of the two top ranked analytes in urine: VEGF(4) p=0.000023, IL-4(3) p=0.000060.

TABLES

TABLE 1

Figure 2A:
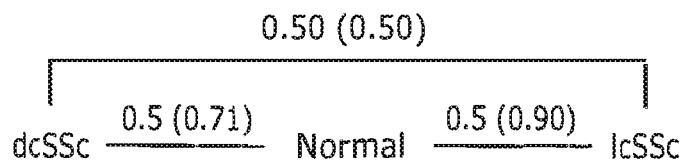
FIG. 2A depicts expression profiling of serum proteomes for classification dcSSc and lcSSc vs. healthy control patients.

Biomarkers for determining a Systemic Lupus Erythematosus-associated disease state

| | Biomarker | Diagnosis serum/plasma | Classification serum/plasma | Prognosis serum/plasma | Prognosis urine | Exemplary sequence(s) |
|---|---|---|---|---|---|---|
| A | | | | | | |
| 1 | Glucagon like peptide-1 (GLP-1) | x | x | x | x | |
| 2 | Procathepsin W | x | x | x | x | |
| B | | | | | | |
| 3 | Angiomotin | x | x | x | x | |
| 4 | C1 esterase inhibitor | x | x | x | x | P05155 |
| 5 | C1q | x | x | x | x | |
| 6 | C1s | x | x | x | x | |
| 7 | C3 | x | x | x | x | |
| 8 | C4 | x | x | x | x | |
| 9 | C5 | x | x | x | x | |
| 10 | CD40 | x | x | x | x | Q6P2H9 |

TABLE 1-continued

Biomarkers for determining a Systemic Lupus Erythematosus-associated disease state

|  | Biomarker | Diagnosis serum/plasma | Classification serum/plasma | Prognosis serum/plasma | Prognosis urine | Exemplary sequence(s) |
|---|---|---|---|---|---|---|
| 11 | Eotaxin | x | x | x | x | P51671 |
| 12 | Complement factor B (Factor B) | x | x | x | x | P00751 |
| 13 | IgM | x | x | x | x |  |
| 14 | IL-10 | x | x | x | x | P22301 |
| 15 | IL-11 | x | x | x | x |  |
| 16 | IL-12 | x | x | x | x | O60595 |
| 17 | IL-13 | x | x | x | x | P35225 |
| 18 | IL-16 | x | x | x | x | Q05BE6, Q8IUU6, B5TY35 |
| 19 | IL-18 | x | x | x | x | Q14116 |
| 20 | IL-1a | x | x | x | x | P01583 |
| 21 | IL-1-ra | x | x | x | x | P18510 |
| 22 | IL-2 | x | x | x | x |  |
| 23 | IL-3 | x | x | x | x | P08700 |
| 24 | IL-4 | x | x | x | x | P05112 |
| 25 | IL-5 | x | x | x | x | BC066282, CH471062, P05113 |
| 26 | IL-6 | x | x | x | x | P05231 |
| 27 | IFN-g | x | x | x | x |  |
| 28 | Integrin alfa-10 | x | x | x | x | Hs158237 |
| 29 | LDL | x | x | x | x |  |
| 30 | Leptin | x | x | x | x |  |
| 31 | Lewis x/CD15 | x | x | x | x | Carbohydrate structure [NA] |
| 32 | Monocyte chemotactiv protein-1 (MCP-1) | x | x | x | x | P13500 |
| 33 | Mucine 1 | x | x | x | x |  |
| 34 | RANTES | x | x | x | x | P13501 |
| 35 | Sialo Lewis x | x | x | x | x | Carbohydrate structure [NA] |
| 36 | TGF-b | x | x | x | x |  |
| 37 | Tumor necrosis factor-alfa (TNF-a) | x | x | x | x |  |
| 38 | VEGF | x | x | x | x |  |
| C |  |  |  |  |  |  |
| 39 | IFN-a | x | x | x |  |  |
| 40 | Monocyte chemotactiv protein-4 (MCP-4) | x | x | x |  | Q99616 |
| 41 | Properdin | x | x | x |  |  |
| D |  |  |  |  |  |  |
| 42 | GM-CSF | x | x |  | x |  |
| 43 | IL-7 | x | x |  | x | AK226000, AB102893, AB102885, P13232 |
| 44 | Integrin alfa-11 | x | x |  | x |  |
| 45 | TM peptide | x | x |  | x |  |
| 46 | Tumor necrosis factor beta (TNF-b) | x | x |  | x | P01374 |
| 47 | Tyrosine protein kinase JAK3 | x | x |  | x |  |
| 48 | Tyrosine protein kinase BTK | x | x |  | x |  |
| E |  |  |  |  |  |  |
| 49 | IL-8 | x |  | x | x | CR623827, CR623683, DQ893727, DQ890564, P10145 |
| F |  |  |  |  |  |  |
| 50 | IL-1b |  | x | x | x | P01584 |
| 51 | Monocyte chemotactiv protein-3 (MCP-3) |  | x | x | x |  |
| G |  |  |  |  |  |  |
| 52 | IL-9 |  |  | x | x | P15248 |
| 53 | Glucagon like peptide-1 receptor (GLP-1 R) |  |  | x | x | P43220 |
| H |  |  |  |  |  |  |
| 54 | CD40 ligand (CD40-L) |  |  |  | x | P29965 |
| 55 | Lewis y |  |  |  | x | Carbohydrate structure [NA] |

TABLE 1-continued

Biomarkers for determining a Systemic Lupus Erythematosus-associated disease state

| | Biomarker | Diagnosis serum/plasma | Classification serum/plasma | Prognosis serum/plasma | Prognosis urine | Exemplary sequence(s) |
|---|---|---|---|---|---|---|
| 56 | HLA-DR | | | | x | |
| 57 | ICAM-1 | | | | x | |
| I | | | | | | |
| 58 | Ku 70/80 | x | x | | | |

TABLE 2

Data from backward elimination performed on the samples outlined in the ms are shown below
Condensed biomarker signatures identified via backward elimination. The cut off value (lowest KL error) is shown in bold text. For samples analysed, see ms.

| A | | B | |
|---|---|---|---|
| SLE v Normal smallestErrorPerLength . . . truncated | abOrder spec (clone) | Normal v SLE1 smallestErrorPerLength . . . truncated | abOrder spec (clone) |
| 10.02424811 | MCP-3 (3) | 7.158246633 | TNF-b (3) |
| 9.611065349 | Eotaxin (2) | 6.734285499 | VEGF (2) |
| 9.862271592 | Eotaxin (1) | 6.791230755 | MCP-1 (2) |
| 9.917643299 | C3 (2) | 8.833899964 | IL-4 (3) |
| 10.47692226 | TM peptide | 8.0977167 | IL-10 (1) |
| 9.984285017 | IL-13 (3) | 8.375559321 | IL-5 (1) |
| 10.53583383 | IL-12 (2) | 12.41982019 | TNF-a (2) |
| 13.8003615 | Procathepsin | 12.12166028 | IgM |
| 12.29382406 | IgM | 12.69130417 | C5 (2) |
| 12.01685397 | IL-18 (3) | NA | C1q (1:3) |
| 14.42179444 | IL-11 (1) | | |
| 17.13775099 | IL-4 (3) | | |
| 18.11722048 | C5 (2) | | |
| 18.93778831 | IL-4 (4) | | |
| NA | IL-10 (1) | | |

| C | | D | |
|---|---|---|---|
| Normal v SLE2 smallestErrorPerLength . . . truncated | abOrder spec (clone) | Normal v SLE3 smallestErrorPerLength . . . truncated | abOrder spec (clone) |
| 7.194695939 | TNF-a (1) | 6.278502579 | Properdine |
| 6.337226476 | IL-11 (1) | 5.823372626 | IL-10 (1) |
| 6.352298315 | IL-6 (3) | 6.477102988 | IL-4 (3) |
| 6.902031286 | IL-18 (3) | 7.001150906 | IL-13 (2) |
| 7.39446424 | IL-1a (1) | 10.54209014 | C5 (2) |
| 8.051461621 | C1q (1:3) | NA | CD40 (3) |
| 8.619005387 | IL-10 (1) | | |
| 10.9815995 | Properdin | | |
| 13.71373569 | Integrin alfa-11 | | |
| NA | MCP-4 (1) | | |

| E | | F | |
|---|---|---|---|
| SLE1 v SLE2 smallestErrorPerLength . . . truncated | abOrder spec (clone) | SLE2 v SLE3 smallestErrorPerLength . . . truncated | abOrder spec (clone) |
| 5.166623518 | IL-3 (3) | 5.79541127 | IL-5 (1) |
| 4.862835743 | Procathepsin W | 5.337911609 | Eotaxin (2) |
| 5.534097155 | Sialo lewis x | 5.845696643 | C4 |
| 6.03519962 | IL-16 (2) | 6.864891626 | MCP-1 (1) |
| 7.790395204 | LDL | 8.041486394 | IL-16 (2) |
| NA | Mucine-1 | 9.309301715 | Factor B (1:3) |
| | | 10.00095556 | MCP-3 (3) |
| | | NA | IL-13 (1) |

TABLE 2-continued

Data from backward elimination performed on the samples outlined in the ms are shown below
Condensed biomarker signatures identified via backward elimination. The cut off value (lowest KL error) is shown in bold text. For samples analysed, see ms.

| G | | H | |
|---|---|---|---|
| SLE1 v SLE3 | | Low v mid activity | |
| smallestErrorPerLength ... truncated | abOrder spec (clone) | smallestErrorPerLength ... truncated | abOrder spec (clone) |
| 5.594692466 | IL-1ra (2) | 5.40743444 | MCP-3 (1) |
| 4.803235665 | Eotaxin (3) | 5.174113098 | IL-9 (3) |
| 4.910363332 | LDL (2) | 5.298135129 | Rantes (1) |
| 5.767538065 | Factor B (1:3) | 5.841458015 | Eotaxin (3) |
| 5.439800683 | IL-3 (3) | 6.325064427 | MCP-1 (3) |
| 5.376324565 | C1q (1:3) | 6.818139153 | C1 esterase inhibitor |
| 6.036996239 | IL-4 (1) | | |
| 6.809190743 | C5 (2) | 7.472013874 | IL-18 (3) |
| 8.859506159 | Rantes (2) | 11.18551421 | GLP-1 R |
| NA | IL-13 (1) | NA | C3 (1) |

| I | | J | |
|---|---|---|---|
| Mid v high activity | | Low v high activity | |
| smallestErrorPerLength ... truncated | abOrder spec (clone) | smallestErrorPerLength ... truncated | abOrder spec (clone) |
| 4.608928233 | Properdin | 6.845867564 | IgM |
| 5.009609494 | IL-18 (3) | 6.690299293 | C5 (2) |
| 6.260774866 | C1q (1:3) | 6.96176956 | C1q |
| NA | IL-1ra (2) | 6.966083677 | Factor B (1:3) |
| | | 7.353295504 | IL-9 (3) |
| | | 8.716225745 | C1q (1:3) |
| | | 9.872039537 | TNF-a (1) |
| | | 16.06695247 | Properdine |
| | | NA | C3 (2) (1:3) |

| K | |
|---|---|
| SLE3 low activity v high activity | |
| smallestErrorPerLength ... truncated | abOrder spec (clone) |
| 3.114458702 | IL-1ra (1) |
| 2.933382183 | IL-12 (1) |
| 2.958195117 | IL-11 (1) |
| 2.998665511 | IL-12 (3) |
| 3.02180794 | VEGF (2) |
| 3.037529114 | IL-2 (1) |
| 3.079988064 | IL-8 (1) |
| 3.075138002 | IL-18 (2) |
| 3.065026368 | VEGF (1) |
| 3.151364341 | C3 (1) |
| 2.952113968 | IL-4 (1) |
| 3.044413345 | Properdine |
| 3.180319889 | IL-12 (2) |
| 3.323653031 | Procathepsin W |
| 3.10267256 | IL-8 (3) |
| 3.31974441 | IL-13 (1) |
| 3.228910282 | IL-11 (3) |
| 3.229975809 | IL-3 (1) |
| 4.242148143 | IL-1a (1) |
| NA | IL-1a (2) |

TABLE 3 appendix - extra analysis showing non-redundant list only of differentially expressed analytes. P < 0.05

| A | B | C | D |
|---|---|---|---|
| SLE set2 | SLE set2 | SLE set 2 | SLE set2 |
| SLE (flare) vs N | SLE (nonflare) vs N | SLE1&NoFlare 10, N 30 | SLE1&Flare 10, N 30 |
| C1s | C3 | C1s | C1s |
| C5 | C4 | C3 | C5 |
| GLP-1 | CD40 | C5 | IL-1a |

TABLE 3-continued appendix - extra analysis showing non-redundant list only of differentially expressed analytes. P < 0.05

| | | | |
|---|---|---|---|
| IL-10 | GLP-1 | GLP-1 | IL-3 |
| IL-12 | IL-12 | IL-1a | MCP-4 |
| IL-13 | IL-13 | IL-3 | TGF-b |
| IL-18 | IL-1a | IL-5 | |
| IL-1a | IL-3 | Properdin | |
| IL-3 | Procathepsin W | TGF-b | |
| IL-5 | Properdin | | |
| IL-8 | TGF-b | | |
| INF-g | TNF-a | | |
| LDL | VEGF | | |
| Procathepsin W | | | |
| TGF-b | | | |
| TNF-a | | | |

| E | F | G | H |
|---|---|---|---|
| SLE set 2 | SLE set2 | SLE set2 | SLE set2 |
| SLE2&NoFlare 10, N 30 | SLE2&NoFlare 10, SLE3&Flare 10 | SLE3&NoFlare 10, N 30 | SLE3&Flare 10, N 30 |
| Properdin | C1q | C3 | C1q |
| C1q | | C4 | C3 |
| | | IL-11 | C4 |
| | | IL-12 | C5 |
| | | Lewis x | GLP-1 |
| | | TGF-b | IL-12 |
| | | VEGF | IL-13 |
| | | | IL-18 |
| | | | IL-1a |
| | | | INF-a |
| | | | INF-g |
| | | | LDL |
| | | | Procathepsin |
| | | | TGF-b |
| | | | TNF-a |

| I | J | K | L |
|---|---|---|---|
| SET2 | SET2 | SET2 | SLE3&Flare 10, |
| SLE1&Flare 10, SLE2&Flare 10 | SLE2&Flare 10, SLE3&Flare 10 | SLE1&Flare 10, SLE3&Flare 10 | SLE3&Inactive 5 |
| LDL | C1q | C1q | C1q |
| | | IL-3 | |
| | | LDL | |
| | | MCP-4 | |

| M | N | O | P |
|---|---|---|---|
| PSLE2&Flare 10, SLE2&Inactive 6 | SLE1&Flare 10, SLE1&Inactive 8 | Flare 30, NoFlare 30 | Flare 30, Inactive 19 |
| IL-8 | IL-10 | C1q | C1q |
| INF-g | IL-11 | IL-18 | IL-10 |
| LDL | IL-12 | INF-g | INF-g |
| Leptin | IL-18 | Integrin alfa-10 | Integrin alfa-10 |
| TGF-b | IL-2 | TGF-b | Leptin |
| | IL-5 | | TGF-b |
| | INF-alpha | | |
| | INF-g | | |
| | Integrin alfa-10 | | |
| | Lewis x | | |

| Q | R | S | |
|---|---|---|---|
| SLE3&Flare 10, SLE3&NoFlare 10 | SLE2&Flare 10, SLE2&NoFlare 10 | Correlation SLEDAI vs analyte concentration | |
| C1q | IL-8 | SET2 | |
| | TGF-b | C1q | |
| | IL-13 | INF-a | |
| | | TNF-a | |
| | | IL-1a | |

| T | U |
|---|---|
| Active vs nonactive pared samples down regulated analytes | Active vs nonactive pared samples up regulated analytes |
| C1q | C4 |
| C3 | IL-10 |
| CD40 | IL-12 |

TABLE 3-continued appendix - extra analysis showing non-redundant list only of differentially expressed analytes. P < 0.05

| | |
|---|---|
| IL-10 | IL-13 |
| IL-11 | IL-18 |
| IL-12 | IL-1α |
| IL-18 | IL-2 |
| IL-3 | IL-3 |
| IL-6 | IL-4 |
| Lewis$^x$ | IL-6 |
| MCP-3 | IL-8 |
| Properdin | INF-γ |
| RANTES | Integrin alfa-10 |
| VEGF | LDL |
| | Leptin |
| | Procathepsin W |
| | TGF-β |
| | VEGF |

TABLE 4

Differentially expressed analytes. Flare vs nonflare groups compared.

A

SERUM
All markers upregulated, but C1q and MCP-4
C1q
C1s
CD40
GLP-1
IgM
IL-10
IL-12
IL-13
IL-16
IL-1a
IL-3
IL-5
IL-6
IL-8
LDL
Lewis x
MCP-1
MCP-3
MCP-4
Procathepsin W
Sialo Lewis x
TNF-a
VEGF

B

URINE
All markers upregulated.
Angiomotin
C1 esterase inhibitor
C1q
C1s
C3
C4
C5
CD40
CD40-L
Eotaxin
Factor B
GLP-1
GLP-1R
GM-CSF
HLA-DR
ICAM-1
IFN-g
IgM
IL-10
IL-11
IL-12
IL-13
IL-16
IL-18
IL-1a
IL-1b
Il-1ra
IL-2
IL-3
IL-4
IL-5
IL-6
IL-7
IL-8
IL-9
Integrin alfa-10
Intergin alfa-11
LDL
Leptin
Lewis x
Lewis y
MCP-1
MCP-3
Mucine 1
Procathepsin W
Rantes
Sialo Lewis x
TGF-b
TM-peptid
TNF-a
TNF-b
Tyrosine protein kinase JAK3
Tyrospine protein kinase BTK
VEGF

TABLE 5

Differentially expressed analytes. Flare vs nonflare compared. Paired samples.

A

SERUM
Angiomotin
C1q
CD40
Eotaxin
Factor B
IL-1b
IL-1ra
IL-6
IL-6
Lewis x

TABLE 5-continued

Differentially expressed analytes. Flare vs nonflare compared. Paired samples.

MCP-1
MCP-3
Mucine 1
Procathepsin W
TGF-b
TNF-a
B

URINE
Angiomotin
C1 esterase inhibitor
C1q
C1s
C3
C4
C5
CD40
CD40L
Eotaxin
Factor B
GLP-1
GLP-1R
GM-CSF
HLA-DR
ICAM-1
IFN-g
IgM
IL-10
IL-11
IL-12
IL-13
IL-16

TABLE 5-continued

Differentially expressed analytes. Flare vs nonflare compared. Paired samples.

IL-18
IL-1a
IL-1b
IL-1ra
IL-2
IL-3
IL-4
IL-5
IL-6
IL-7
IL-8
IL-9
Intergin alfa-10
Intergin alfa-11
LDL
Leptin
Lewis x
Lewis y
MCP-1
MCP-3
Mucin 1
Procathepsin W
Rantes
Sialo Lewis x
TGF-b
TM peptide
TNF-a
TNF-b
Tyrosine protein kinase JAK3
Tyrospine protein kinase BTK
VEGF

TABLE 6

Revised criteria of the American College of Rheumatology (formerly American Rheumatism Association) for the classification of systemic lupus erythematosus. [2]

| | |
|---|---|
| 1. Malar Rash | Fixed erythema, flat or raised, over the malar eminences, tending to spare the nasolabial folds |
| 2. Discoid rash | Erythematous raised patches with adherent keratotic scaling and follicular plugging; atrophic scarring may occur in older lesions |
| 3. Photosensitivity | Skin rash as a result of unusual reaction to sunlight, by patient history or physician observation |
| 4. Oral ulcers | Oral or nasopharyngeal ulceration, usually painless, observed by physician |
| 5. Nonerosive Arthritis | Involving 2 or more peripheral joints, characterized by tenderness, swelling, or effusion |
| 6. Pleuritis or Pericarditis | (a) Pleuritis--convincing history of pleuritic pain or rubbing heard by a physician or evidence of pleural effusion or (b) Pericarditis--documented by electrocardiogram or rub or evidence of pericardial effusion |
| 7. Renal Disorder | (a) Persistent proteinuria >0.5 grams per day or > than 3+ if quantitation not performed or (b) Cellular casts--may be red cell, hemoglobin, granular, tubular, or mixed |
| 8. Neurologic Disorder | (a) Seizures--in the absence of offending drugs or known metabolic derangements; e.g., uremia, ketoacidosis, or electrolyte imbalance or (b) Psychosis--in the absence of offending drugs or known metabolic derangements, e.g., uremia, ketoacidosis, or electrolyte imbalance |
| 9. Hematologic Disorder | (a) Hemolytic anemia--with reticulocytosis or (b) Leukopenia--< 4,000/mm$^3$ on ≥2 occasions or (c) Lyphopenia--<1,500/mm$^3$ on ≥2 occasions or (d) Thrombocytopenia--<100,000/mm$^3$ in the absence of offending drugs |
| 10. Immunologic Disorder | (a) Anti-DNA: antibody to native DNA in abnormal titer or (b) Anti-Sm: presence of antibody to Sm nuclear antigen or (c) Positive finding of antiphospholipid antibodies on: (1) an abnormal serum level of IgG or IgM anticardiolipin antibodies, (2) a positive test result for lupus anticoagulant using a standard method, or (3) a false-positive test result for at least 6 months confirmed by *Treponema pallidum* immobilization or fluorescent treponemal antibody absorption test |

TABLE 6-continued

Revised criteria of the American College of Rheumatology (formerly American Rheumatism Association) for the classification of systemic lupus erythematosus. [2]

| | |
|---|---|
| 11. Positive Antinuclear Antibody | An abnormal titer of antinuclear antibody by immunofluorescence or an equivalent assay at any point in time and in the absence of drugs |

ECG, electrocardiogram;
IgG, immunoglobulin G;
IgM, immunoglobulin M.

TABLE 7

Patients characteristic and clinical parameters

| | SLE | | |
|---|---|---|---|
| | I cohort | II cohort | N |
| Number of samples | 10 + 10 | 30 + 30 | 30 |
| Age | | | |
| Mean | 50 | 44 | 44 |
| Range | 30-67 | 19-71 | 20-69 |
| Gender | | | |
| F | 10 | 27 | 28 |
| M | 0 | 3 | 2 |
| SLE status | | | |
| SLE1 | 6 + 6 | 10 + 10 | — |
| SLE2 | 3 + 3 | 10 + 10 | — |
| SLE3 | 1 + 1 | 10 + 10 | — |
| SLEDAI disease activity | | | |
| no activity (SLEDAI = 0) | 8 | 19 | — |
| mild (SLEDAI = 1-5) | 6 | 16 | — |
| moderate (SLEDAI = 6-10) | 6 | 14 | — |
| high (SLEDAI = 11-19) | — | 8 | — |
| very high (SLEDAI ≥ 20) | — | 3 | — |
| Cell apoptosis, % | | | |
| Mean | 35 | — | — |
| Range | 9-76 | — | — |
| Treatment | | | |
| Prednisone use, % | 90 | 93 | — |
| Immunosuppressants use, % | 50 | 63 | — |
| Antimalarias use, % | 70 | — | — |

TABLE 8

Specificity and concentration of the recombinant antibodies used in the array experiments.

| Antigen (no of clones) | Concentration [mg/ml] | Antigen (no of clones) | Concentration [mg/ml] |
|---|---|---|---|
| IL-1α (1) | 0.1 | IL-18 (2) | 0.1 |
| IL-1α (2) | 0.3 | MCP-4 (1) | 0.3 |
| IL-2 (1) | 0.1 | INF-γ (1) | 0.2 |
| IL-2 (2) | 0.3 | INF-γ (3) | 0.2 |
| IL-2 (3) | 0.1 | RANTES (1) | 0.5 |
| IL-3 (1) | 0.1 | MCP-3 (2) | 0.5 |
| IL-3 (2) | 0.5 | Leptin | 0.2 |
| IL-3 (3) | 0.3 | Alfa-10 | 0.1 |
| IL-4 (1) | 0.1 | LDL (1) | 0.5 |
| IL-4 (2) | 0.4 | Lewis$^x$ (1) | 0.5 |
| IL-5 (3) | 0.5 | Lewis$^x$ (2) | 0.5 |
| IL-6 (1) | 0.2 | Sialle x | 0.2 |
| IL-8 (1) | 0.5 | Procathepsin | 0.3 |
| IL-10 (1) | 0.3 | GLP-1 | 0.1 |
| IL-10 (2) | 0.3 | C1q | 0.1 |
| IL-10 (3) | 0.3 | C1s | 0.1 |
| IL-11 (1) | 0.1 | C3 (1) | 0.1 |
| IL-11 (2) | 0.5 | C3 (2) | 0.1 |
| IL-11 (3) | 0.2 | C4 | 0.1 |
| IL-12 (1) | 0.5 | C5 (1) | 0.1 |
| IL-12 (2) | 0.5 | C5 (2) | 0.1 |
| IL-13 (2) | 0.5 | Factor B | 0.1 |
| IL-13 (3) | 0.5 | IL-6 (3) | 0.1 |
| VEGF (1) | 0.5 | IL-8 (3) | 0.1 |
| VEGF (2) | 0.5 | Properdine | 0.1 |
| TGF-β1 (2) | 0.5 | TNF-β (3) | 0.2 |
| TNF-α (3) | 0.5 | IL-4 (4) | 0.05 |
| IL-1ra (2) | 0.2 | CD40 (3) | 0.1 |
| IL-18 (1) | 0.3 | INF-α | 0.2 |

TABLE 9

Significant up- and down-regulations of serum protein expression profiles between samples collected from the same patient during either flare or remission. Up-regulation indicated by italic text, down-regulation indicated by bold text.

| Antigen (no of clones) | n UP (max = 19) |
|---|---|
| Lewis$^x$ (1) | 3 |
| CD40 (3) | 4 |
| IL-11 (2) | 6 |
| IL-18 (1) | 6 |
| RANTES (1) | 6 |
| Lewis$^x$ (2) | 6 |
| IL-3 (2) | 7 |
| VEGF (1) | 7 |
| C1q | 7 |
| IL-6 (3) | 7 |
| IL-10 (1) | 8 |
| IL-10 (3) | 8 |
| IL-11 (3) | 8 |
| IL-12 (1) | 8 |
| MCP-3 (2) | 8 |
| C3 (1) | 8 |
| Properdine | 8 |
| IL-1α (2) | 9 |
| IL-3 (3) | 9 |
| TNF-α (3) | 9 |
| MCP-4 (1) | 9 |
| C3 (2) | 9 |
| TNF-β (3) | 9 |
| IL-4 (4) | 9 |
| IL-4 (2) | 10 |
| IL-5 (3) | 10 |
| IL-11 (1) | 10 |
| IL-13 (3) | 10 |
| IL-1ra (2) | 10 |
| Sialle x | 10 |

TABLE 9-continued

Significant up- and down-regulations of serum protein expression profiles between samples collected from the same patient during either flare or remission. Up-regulation indicated by italic text, down-regulation indicated by bold text.

| Antigen (no of clones) | n UP (max = 19) |
|---|---|
| GLP-1 | 10 |
| C1s | 10 |
| C5 (1) | 10 |
| C5 (2) | 10 |
| Factor B | 10 |
| INF-α | 10 |
| *IL-4 (1)* | *11* |
| *IL-12 (2)* | *11* |
| *IL-13 (2)* | *11* |
| *IL-2 (2)* | *12* |
| *IL-2 (3)* | *12* |
| *IL-6 (1)* | *12* |
| *IL-8 (1)* | *12* |
| *IL-10 (2)* | *12* |
| *VEGF (2)* | *12* |
| *Alfa-10* | *12* |
| *Procathepsin* | *12* |
| *IL-8 (3)* | *12* |
| *IL-2 (1)* | *13* |
| *TGF-β1 (2)* | *13* |
| *Leptin* | *13* |
| *IL-3 (1)* | *14* |
| *IL-18 (2)* | *14* |
| *INF-γ (3)* | *14* |
| *C4* | *14* |
| *IL-1α (1)* | *15* |
| *INF-γ (1)* | *15* |
| *LDL (1)* | *15* |

TABLE 10 scFvs (clone)

| | | | |
|---|---|---|---|
| IL-1a (1) | TNF-a (2) | Angiomotin (2) | IL-6 (4) |
| IL-2 (2) | GM-CSF (2) | Alfa-11 | Properdine |
| IL-3 (2) | TNF-b (2) | LDL (2) | VEGF (3) |
| IL-4 (2) | IL-1ra (3) | Lewis x (2) | IL-4 (4) |
| IL-5 (3) | IL-18 (1) | TM peptide | CD40 (2) |
| IL-7 (1) | MCP-4 (2) | JAK3 | CT-17 |
| IL-8 (2) | IFN-g (3) | GLP-1 | Sialle Ag x |
| IL-9 (3) | IL-1b (3) | IgM (1) | MCP-1 (M3) |
| IL-10 (3) | Eotaxin (3) | C3 (1) | MCP-1 (M6) |
| IL-11 (3) | Rantes (3) | C5 (1) | CystC (3) |
| IL-13 (1) | MCP-1 (3) | Factor B | Mucine (P3-13) |
| VEGF (1) | TGF-b1 (3) | CD40 ligand | IL-1a (3) |
| IL-1a (2) | TNF-a (3) | Leptin | IL-8 (3) |
| IL-2 (3) | GM-CSF (3) | B | TNF-b (3) |
| IL-3 (3) | IL-1ra (1) | PSA | VEGF (4) |
| IL-5 (1) | IL-16 (1) | Lewis y | Mucine (Smuc159) |
| IL-6 (1) | IL-18 (2) | Procathepsin | CD40 (3) |
| IL-7 (2) | IFN-g (1) | Digoxin | IgM (2) |
| IL-9 (1) | IL-1b (1) | HLA-DR | MCP-1 (M1) |
| IL-10 (1) | Eotaxin (1) | C1q | MCP-1 (M4) |
| IL-11 (1) | Rantes (1) | C3 (2) | CystC (1) |
| IL-12 (1) | MCP-1 (1) | C5 (2) | CystC (4) |
| IL-13 (2) | MCP-3 (1) | IL-12 (3) | Mucine (P3-15) |
| VEGF (2) | MCP-3 (3) | IL-16 (3) | Mucine (P3-24) |
| IL-2 (1) | TNF-a (1) | Angiomotin (1) | IL-6 (3) |
| IL-3 (1) | GM-CSF (1) | Alfa-10 | MCP-4 (3) |
| IL-4 (1) | TNF-b (1) | LDL (1) | TNF-b (4) |
| IL-5 (2) | IL-1ra (2) | Lewis x (1) | IL-4 (3) |
| IL-6 (2) | IL-16 (2) | Sialle Lewis x | CD40 (1) |
| IL-8 (1) | MCP-4 (1) | BTK | CD40 (4) |
| IL-9 (2) | IFN-g (2) | GLP-1R | IgM (3) |
| IL-10 (2) | IL-1b (2) | ICAM-1 | MCP-1 (M2) |
| IL-11 (2) | Eotaxin (2) | C1s | MCP-1 (M5) |
| IL-12 (2) | Rantes (2) | C4 | CystC (2) |
| IL-13 (3) | MCP-1 (2) | EI | Mucine (P3-06) |
| TGF-b1 (1) | MCP-3 (2) | IL-12 (4) | Mucine (P3-16) |
| TGF-b1 (2) | B-galactosidase | IL-18 (3) | |

TABLE 11

Demographic data of the SSc patients included in the study

| Parameter | lcSSc | dcSSc |
|---|---|---|
| No. | 10 | 10 |
| Gender (female:male) | 10:0 | 7:3 |
| Age at onset | 51 (44-70) [a] | 47 (34-55) [a] |
| Duration (months) | 31 (24-43) [a] | 17 (10-28) [a] |
| Skin score | 10 (9-12) [a] | 17 (10-28) [a] |
| Organ involvement | | |
| Esophagus | 10 | 9 |
| lung | 5 | 7 |
| heart | 1 | 4 |
| PAH | 1 | 0 |
| Kidney | 1 | 1 |
| Muscle | 0 | 1 |
| Joint | 1 | 1 |
| No. ANA positive | 10 | 10 |
| No. anti-Scl-70 positive | 0 | 4 |
| No. anti-centromere positive | 8 | 0 |
| No. ESR raised | 2 | 5 |
| No. CRP raised | 3 | 6 |
| N0. IgG raised | 2 | 4 |

[a] Median (25th and 75th percentile)

TABLE 12

Demographic data of the SLE patients included in the study

| Parameter | SLE1 | SLE2 | SLE3 |
|---|---|---|---|
| No. | 10 | 10 | 10 |
| Gender (female:male) | 10:0 | 8:2 | 8:2 |
| Age at onset | 45 (26-51) [a] | 38 (27-46) [a] | 28 (24-34) [a] |
| Duration (months) | 102 (42-179) [a] | 79 (15-206) [a] | 74 (10-139) [a] |
| SLEDAI-2K | 61 (4-10) [b] | 7 (2-32) [b] | 16 (10-32) [b] |
| Treatment | | | |
| Prednisolon | 4 | 8 | 0 |
| Hydrochloroquine | 5 | 4 | 2 |
| Azathoprine | 2 | 4 | 1 |
| Cyclosporine S | 1 | 0 | 3 |
| Cyclosphosphamide | 1 | 0 | 3 |
| Methotrexate | 0 | 0 | 1 |
| Intravenous Ig | 0 | 0 | 1 |
| Definition | | | |

| | |
|---|---|
| SLE1 | Skin and musculoskeletal involvement |
| SLE2 | Serositis, systemic vasculitis, but not kidney involvement |
| SLE3 | SLE glomerulonephritis |

[a] Median (25th and 75th percentile)
[b] Median ± range

TABLE 13

The different scFv specificities used for the antibody microarrays

| Antigen (number of clones) | Antigen (number of clones) |
|---|---|
| Angiomotin (2) | IL-16 (3) |
| B cell receptor µ chain (1) | IL-18 (3) |
| C1 esterase inhibitor (1) | IFN-γ (3) |
| C1q (1) | Integrin α-10 (1) |
| C1s (1) | Integrin α-11 (1) |

TABLE 13-continued

The different scFv specificities used for the antibody microarrays

| Antigen (number of clones) | Antigen (number of clones) |
|---|---|
| C3 (2) | Ku 70/80 (2) |
| C4 (1) | LDL (2) |
| C5 (2) | Leptin (1) |
| CD40 (4) | Lewis$^x$ (2) |
| CD40 ligand (1) | Lewis$^y$ (1) |
| Eotaxin (3) | MCP-1 (3) |
| Factor B (1) | MCP-3 (3) |
| GLP-1 (1) | MCP-4 (2) |
| GLP-1-R (1) | Mucine-1 (1) |
| GM-CSF (3) | Peptide motifs (10) |
| IL-1α (3) | Procathepsin (1) |
| IL-1β (3) | Properdin (1) |
| IL-1-ra (3) | PSA (1) |
| IL-2 (3) | Rantes (2) |
| IL-3 (3) | Sialyl Lewis$^x$ (1) |
| IL-4 (4) | TGF-β1 (3) |
| IL-5 (3) | Tm peptide (1) |
| IL-6 (4) | TNF-α (3) |
| IL-7 (2) | TNF-β (4) |
| IL-8 (3) | Tyrosine-protein kinase BTK (1) |
| IL-9 (3) | Tyrosine-protein kinase JAK3 (1) |
| IL-10 (3) | VEGF (4) |
| IL-11 (3) | Choleratoxin subunit B (1) (control) |
| IL-12 (4) | FITC (1) (control) |
| IL-13 (3) | |

TABLE 14

Clinical data

| patient | age | samples taken: serum | samples taken: urine | DA |
|---|---|---|---|---|
| A | 41 | 2005 Jun. 8 | 2005 Jun. 8 | 0 |
| B | 67 | 2005 Jun. 21 | 2005 Jun. 21 | 1 |
| C | 43 | 2005 Jun. 27 | 2005 Jun. 27 | 1 |
| | | 2005 Aug. 24 | 2005 Aug. 24 | 1 |
| | | 2005 Oct. 18 | 2005 Oct. 18 | 1 |
| D | 30 | 2005 Jul. 1 | 2005 Jul. 1 | 0 |
| | | 2005 Jul. 27 | 2005 Jul. 27 | 0 |
| E | 27 | 2005 Sep. 5 | 2005 Sep. 5 | 1 |
| | | 2007 May 9 | 2007 May 9 | 1 |
| | | 2007 Aug. 30 | 2007 Aug. 30 | 1 |
| | | 2009 Jan. 20 | 2009 Jan. 20 | 0 |
| F | 49 | 2005 Sep. 14 | 2005 Sep. 15 | 0 |
| | | 2005 Nov. 14 | 2005 Nov. 14 | 0 |
| | | 2006 Sep. 14 | 2006 Sep. 14 | 0 |
| | | 2006 Dec. 11 | 2006 Dec. 11 | 0 |
| G | 31 | 2005 Sep. 21 | 2005 Sep. 21 | 0 |
| | | 2005 Nov. 17 | 2005 Nov. 17 | 0 |
| | | 2006 Jan. 19 | 2006 Jan. 19 | 0 |
| | | 2009 Jun. 2 | 2009 Jun. 2 | 0 |
| H | 34 | 2005 Sep. 21 | 2005 Sep. 21 | 0 |
| | | 2005 Nov. 1 | 2005 Nov. 1 | 0 |
| | | 2005 Nov. 22 | 2005 Nov. 22 | 0 |
| | | 2006 Jan. 23 | 2006 Jan. 23 | 0 |
| I | 38 | 2006 Mar. 27 | x | 1 |
| | | 2006 Apr. 21 | 2006 Apr. 24 | 1 |
| | | 2006 Jun. 21 | 2006 Jun. 21 | 0? |
| | | 2007 Sep. 12 | 2007 Sep. 12 | 0? |
| J | 46 | 2006 Mar. 30 | 2006 Mar. 30 | 1 |
| | | 2006 Jun. 21 | 2006 Jun. 21 | 1 |
| | | 2007 Sep. 10 | 2007 Sep. 10 | 1 |
| | | 2009 Jan. 27 | 2009 Jan. 27 | 1 |
| K | 38 | 2006 Jun. 21 | 2006 Jun. 21 | 1 |
| | | 2007 Sep. 6 | 2007 Sep. 6 | 0 |
| L | 57 | 2006 Jul. 4 | 2006 Jul. 4 | 1 |
| | | 2007 Sep. 18 | 2007 Sep. 18 | 0 |
| M | 42 | 2006 Aug. 16 | 2006 Aug. 16 | 1? |
| N | 35 | 2006 Oct. 25 | 2006 Oct. 26 | 1 |
| | | 2006 Jun. 14 | 2006 Jun. 15 | 0 |
| O | 56 | 2006 Dec. 13 | 2006 Dec. 13 | 1 |
| P | 38 | 2007 Feb. 26 | 2007 Feb. 26 | 1 |
| | | 2007 Jun. 13 | 2007 Jun. 13 | 1 |
| | | 2007 Sep. 19 | 2007 Sep. 19 | 1 |
| Q | 59 | 2007 May 9 | 2007 May 9 | 1 |
| R | 43 | 2007 Oct. 5 | 2007 Oct. 11 | 1 |
| | | 2007 Oct. 25 | 2007 Oct. 25 | 1 |
| | | 2008 Feb. 5 | 2008 Feb. 5 | 1 |
| S | 47 | 2008 Jan. 3 | 2008 Jan. 3 | 1 |
| | | 2008 Dec. 11 | 2008 Dec. 11 | 1 |
| T | 27 | 2008 Jan. 8 | 2008 Jan. 8 | 1 |
| U | 23 | 2009 Jan. 20 | 2009 Jan. 29 | 1 |
| | | 2009 Feb. 21 | 2009 Feb. 10 | 1 |
| V | 31 | 2009 Feb. 24 | 2009 Mar. 5 | 1 |
| | | 2009 Mar. 19 | 2009 Mar. 19 | 1 |
| W | 29 | 2009 Mar. 11 | 2009 Mar. 11 | 1 |
| X | 42 | 2009 Apr. 17 | 2009 Apr. 22 | 1 |
| Y | 47 | 2009 Apr. 22 | 2009 Apr. 22 | 1 |
| Z | 18 | 2009 Sep. 30 | 2009 Sep. 30 | 1 |
| AA | 39 | 2005 Jun. 29 | 2005 Jun. 29 | 1 |

TABLE 15

The following parameters were obtained using the e1071 1.5-24 SVM, available from http://cran.r-project.org/web/packages/e1071/index.html.

```
# Required Functions:
svmlooB<- function(subset1,subset2, group1 ,group2){
ProteinNames<-rownames(logdata)
p <- apply(logdata , 1 , wilcoxtest , subset1 , subset2)
fc <- apply(logdata , 1 , foldchange , subset1 , subset2)
a<-order(p)
p<-p[a]
fc<-fc[a]
analyteList<-cbind(p,fc)
svmfac <- factor(rep('rest',ncol(logdata)),levels=c(group1,group2,'rest'))
svmfac[subset1] <- group1
svmfac[subset2] <- group2
dataset<-logdata[,subset1|subset2]
fac<-factor(as.character(svmfac[subset1|subset2]),levels=c(group1,group2))
n1 <- sum(fac==levels(fac)[1])
n2 <- sum(fac==levels(fac)[2])
nsamples <- n1+n2
ngenes <- nrow(dataset)
SampleInformation <- paste(levels(fac)[1]," ",n1," ",levels(fac[2]," ",n2,sep="")
```

TABLE 15-continued

The following parameters were obtained using the e1071 1.5-24 SVM, available from http://cran.r-project.org/web/packages/e1071/index.html.

```
res <- numeric(nsamples)
sign <- numeric(nsamples)
for (i in 1:nsamples){
    svmtrain <- svm(t(dataset[,-i]) , fax[-i] , kernel="linear" )
    pred <- predict(svmtrain , t(dataset[,i]) , decision.values=TRUE)
    res[i] <- as.numeric(attributes(pred)$decision.values)
    facnames <- colnames(attributes(pred)$decision.values)[1]
    if (facnames == paste(levels(fac)[1],"/",levels(fac)[2],sep="")){sign[i] <- 1}
    if (facnames == paste(levels(fac)[2],"/",levels(fac)[1],sep="")){sign[i] <- -1}
}
if (length(unique(sign)) >1){
    print("Shifted signs...")
}
res <- sign * res
names <- colnames(dataset , do.NULL=FALSE)
orden <- order(res , decreasing=TRUE)
Samples <- data.frame(names[orden],res[orden],fac[orden])
ROCdata <- myROC(res,fac)
write(paste(group1," (",sum(subset1),") versus ",group2," (",sum(subset2),")\tROC
area:\t",ROCdata[1],"\tp-value:\t",ROCdata[2] ,sep="") , file="output.txt" , append=TRUE)
    write("" , file="output.txt" , append=TRUE)
    write("Analyte\tWilcox p-value\tFoldchange" , file="output.txt" , append=TRUE)
    write.table(analyteList, file="output.txt" , append=TRUE, sep="\t" , quote=FALSE,col.names =
FALSE)
    write("" , file="output.txt" , append=TRUE)
    write("" , file="output.txt" , append=TRUE)
    roc(as.numeric(fac),res, plot=TRUE)
    return(cbind(as.numeric(fac),res))
}
foldchange <- function(prot,subset1,subset2){
    2^(mean(prot[subset1]) - mean(prot[subset2]))
}
wilcoxtest <- function(prot,subset1,subset2){
    res <- wilcox.test(prot[subset1],prot[subset2])
    res$p.value
}
myROC <- function(numbers , fac){
    n1 <- sum(fac==levels(fac)[1])
    n2 <- sum(fac==levels(fac)[2])
    wilcoxresult <- wilcox.test(numbers~fac , alternative="greater")
    ROCarea <- as.numeric(wilcoxresult$statistic)/(n1*n2)
    pval <- wilcoxresult$p.value
    return(c(ROCarea,pval))
}
```

EXAMPLE A

Systemic lupus erythematosus (SLE) and systemic sclerosis (SSc) are two severe autoimmune connective tissue diseases. The fundamental knowledge about their aetiology is limited and the conditions display complex pathogenesis, multifaceted presentations, and unpredictable courses. Despite significant efforts, the lack of fully validated biomarkers enabling diagnosis, classification, and monitoring of disease activity represents significant unmet clinical needs. In this discovery study, we have for the first time used recombinant antibody microarrays for miniaturized, multiplexed serum protein profiling of SLE and SSc, targeting mainly immunoregulatory proteins. The data showed that several candidate SLE-associated multiplexed serum biomarker signatures were delineated, reflecting disease (diagnosis), disease severity (phenotypic subsets) and disease activity. Further, biomarker signatures differentiating SLE versus SSc were demonstrated, and the observed differences increased with severity of SLE. Hence, we have shown that affinity proteomics could be used to de-convolute crude, non-fractionated serum proteomes, extracting molecular portraits of SLE and SSc, further enhancing our fundamental understanding of these complex autoimmune conditions.

Introduction

Systemic lupus erythematosus (SLE) (1-2) and systemic sclerosis (SSc), or scleroderma, (3-4) are two severe, chronic autoimmune connective tissue diseases with still unknown aetiology, complex pathogenesis, heterogeneous presentation, and unpredictable course. As a consequence, the difficulties in diagnosing, classifying, and treating both SLE (1, 5-6) and SSc (3-4, 7-8) are significant. Thus, further studies delineating SLE and SSc, and revealing the underlying disease biology at the molecular level are highly warranted.

SLE is a multifaceted disease, with a prevalence of 40 to 200 cases per 100,000 persons (2), for which the lack of specific biomarkers is critical and that impairs the clinical management of these patients (6, 9-12). First, the clinical symptoms vary so much that it often mimics or is mistaken for other conditions (1-2). Since no single diagnostic test is at hand, SLE is currently diagnosed when at least 4 of 11 complex, clinical criteria, as defined by the American College of Rheumatology (ACR) (13-14), are fulfilled. Second, the course of the disease is characterized by alternating periods of flares and remissions (1-2). There are no biomarkers at hand for predicting and/or identifying the start and end of a flare, which would be a key feature for optimizing treatment (1-2, 5). Third, the therapeutic regime could be even further optimized if validated biomarkers for stratifying the patients into clinical phenotypic subsets, reflecting disease severity (15), were available. Fourth, the absence of markers has significantly hampered the efforts to monitor and evaluate the effects of (novel) therapeutics (6, 16). Considering the complexity of SLE, it is reasonable to argue that more than one biomarker signature will be required in order to reflect all aspects of SLE (6). Hence, the need to define molecular portraits associated with SLE is significant.

Compared to SLE (inflammatory phenotype) (1-2), SSc displays a less anti-inflammatory and more fibrotic phenotype (4, 7, 17). This disorder, which has a prevalence of about 3 to 24 cases per million persons (18), is as SLE, diagnosed by evaluating an intricate pattern of clinical features. Based on the pattern of skin involvement (19), SSc is commonly classified into two subsets, limited cutaneous SSc (lcSSc) and diffuse cutaneous SSc (dcSSc). As for SLE, the need for specific biomarkers of SSc for diagnosis, classification, prognosis, and for monitoring the response to therapy is significant (8, 20).

Considering the nature of SLE (1-2) and SSc (3, 8, 17), deciphering the serum, plasma and/or urine proteomes, would shed further light on these diseases, and could provide the candidate biomarker signatures much longed for (6, 8, 10-12, 20). Despite major efforts, using a plethora of methods, including conventional proteomic technologies, such as 2D-gels and mass spectrometry, our knowledge about the serum, plasma and urine signatures reflecting SLE (6, 10-12) and SSc (3, 7-8, 20) is still very limited, and mainly restricted to single laboratory variables displaying inadequate specificity and sensitivity. Targeting crude proteomes, such as serum, has proven challenging using standard proteomic approaches due to sample complexity and methodological shortcomings (21-23).

In recent years, affinity proteomics, mainly represented by antibody-based microarrays, have been established as a technology capable of performing multiplex profiling of complex proteomes in a sensitive manner (24-26). In this context, we have developed a state-of-the-art recombinant antibody microarray technology platform (24, 27-28) and validated its use within disease proteomics (24, 29-32). Focusing on various cancers (30-33) and inflammatory conditions (31) (Wngren et al., unpublished observations), we have deciphered candidate serum/plasma and tissue biomarker signatures for e.g. disease diagnosis, prognosis, and classification, as well as for monitoring the molecular effects of therapy and for selecting patients eligible for therapy.

In this study, we have for explored the potential of our recombinant antibody microarray set-up for profiling the serum proteome of SLE and SSc, targeting high- and low-abundant immunoregulatory proteins in crude, directly biotinylated sera. The data showed that several SLE-associated candidate serum protein signatures could for the first time be identified reflecting disease, disease severity (phenotypic subsets), and disease activity. While SLE and SSc could be differentiated, the data implied that the serum profiles of SSc vs. controls were more similar. Hence, this study demonstrated that a minimally invasive blood sample harbored disease-specific information reflecting autoimmune connective tissue diseases, further enhancing our fundamental understanding of SLE and SSc.

Materials and Methods
Clinical Samples

This study was approved by the regional ethics review board in Lund, Sweden. In total, 65 serum samples were collected at Lund University Hospital (Lund, Sweden), including 20 SSc patients (Table 11), 30 SLE patients (Table 12), and 15 healthy volunteers (mean age 44 (range 20-69), gender female:male 14:1). The SLE and SSc patients were all recruited from the Dept. of Rheumatology (Lund University Hospital) (34-35). Serum samples of the SSc patients were collected at the first enrolment for inquiry of the SSc diagnosis, and the demographics are described in Table 11. The SSc patients fulfilled the inclusions criteria of a) a definitive diagnosis of SSc according to the ACR (36); b) a disease duration of less than five years from the onset of skin involvement; and c) had not been previously treated with any of the following drugs: azathioprine, chlorambucil, colchicine, cyclophosphamide, cyclosporine S, D-penicillamine, methotrexate or mycophenolate mofetil. The SSc patients were grouped according to whether they had limited cutaneous SSc (lcSSc, n=10) or diffuse cutaneous SSc (dcSSc, n=10) (19), and the clinical data were obtained as previously described (37). The SLE patients had clinical SLE diagnosis and displayed four or more ACR classification criteria (13-14). The serum samples were collected during follow-up when the patients were presented with a flare. The demographics are described in Table 12. The SLE patients were grouped according to disease severity as previously described (15): 1) skin and musculoskeletal involvement (SLE1, n=10); 2) serositis, systemic vasculitis but not kidney involvement (SLE2, n=10); and 3) presence of SLE glomerulonephritis (SLE3). The clinical disease activity was defined as SLEDAI-2K score (38). All samples were aliquoted and stored at −80° C. until further use.

Labeling of Serum Samples

The serum samples were labeled using previously optimized labeling protocols for serum proteomes (27-28, 39). Briefly, the serum samples were diluted 1:45 in PBS, resulting in a concentration of about 2 mg/ml, and biotinylated at a molar ratio of biotin:protein of 15:1 using EZ-Link Sulfo-NHS-LC-Biotin (Pierce, Rockford, Ill., USA). Unreacted biotin was removed by dialysis against PBS for 72 hours, using a 3.5 kDa MW dialysis membrane (Spectrum Laboratories, Rancho Dominguez, Calif., USA). The samples were aliquoted and stored at −20° C.

Production and Purification of scFv 135 human recombinant scFv antibody fragments directed against 60 different analytes mainly involved in immunoregulation, anticipated to reflect the events taking place in SLE and SSc (Table 13), were selected from the n-CoDeR library (40) and kindly provided by BioInvent International AB (Lund, Sweden). Thus, each antigen was recognized by up to four different scFv fragments, which was part of the quality control of the arrays. All scFv antibodies were produced in 100 ml *E. coli* cultures and purified from expression supernatants, using affinity chromatography on Ni-NTA agarose (Qiagen, Hilden, Germany). Bound molecules were eluted with 250 mM imidazole, extensively dialyzed against PBS, and stored at 4° C., until further use. The protein concentration was determined by measuring the absorbance at 280 nm (average concentration 480 µg/ml, range 100 to 800 µg/ml). The degree of purity and integrity of the scFv antibodies were evaluated by 10% SDS-PAGE (Invitrogen, Carlsbad, Calif., USA).

Fabrication and Processing of Antibody Microarrays

For production of the antibody microarrays, we used a set-up previously optimized and validated (27-28, 30, 32). Briefly, the scFv microarrays were fabricated, using a non-contact printer (Biochip Arrayer, Perkin Elmer Life & Analytical Sciences). The antibodies were spotted onto black polymer MaxiSorb microarray slides (NUNC A/S, Roskilde, Denmark), resulting in an average of 11 fmol scFv per spot (range 2-19 fmol). Eight replicates of each scFv clone were arrayed to ensure adequate statistics. The on-chip performances of the antibodies have been previously validated (27, 30-32, 41), for review see (41-44). In total, 160 antibodies and controls were printed per slide orientated in two columns with 8×80 spots per column.

For handling of the arrays, we used a protocol recently optimized (33). Briefly, the slides were manually blocked in 5% (w/v) fat-free milk powder (Semper A B, Sundbyberg, Sweden) in PBS, and then placed in a Protein Array Workstation (PAW) (Perkin Ellmer Life & Analytical Sciences) for automated handling. The slides were washed with 0.05% (v/v) Tween-20 in PBS (PBS-T). The biotinylated serum sample was diluted 1:2 (resulting in a total serum dilution of 1:90) in 1% (w/v) fat-free milk powder and 1% (v/v) Tween in PBS (PBS-MT) prior to incubation on the array. The arrays were visualized with 1 μg/ml Alexa-647 conjugated streptavidin diluted in PBS-MT. Finally, the arrays were dried under a stream of nitrogen gas and scanned with a confocal microarray scanner (ScanArray Express, Perkin Elmer Life & Analytical Sciences) at 5 μm resolution, using three different scanner settings. The ScanArray Express software V3.0 (Perkin Elmer Life & Analytical Sciences) was used to quantify the intensity of each spot, using the fixed circle method. The local background was subtracted and to compensate for possible local defects, the two highest and the two lowest replicates were automatically excluded and each data point represents the mean value of the remaining four replicates. The coefficient of correlation for intra-assays was >0.99 and for inter-assays>0.96, respectively.

Data Normalization

Only non-saturated spots were used for further analysis of the data. Chip-to-chip normalization of the data sets was performed, using a semi-global normalization approach (24, 30, 32), conceptually similar to the normalization developed for DNA microarrays. Thus, the coefficient of variation (CV) was first calculated for each analyte and ranked. Fifteen percent of the analytes that displayed the lowest CV-values over all samples were identified, corresponding to 21 analytes, and used to calculate a chip-to-chip normalization factor. The normalization factor $N_i$ was calculated by the formula $N_i=S_i/\mu$, where $S_i$ is the sum of the signal intensities for the 21 analytes for each sample and $\mu$ is the sum of the signal intensities for the 21 analytes averaged over all samples. Each data-set generated from one sample was divided with the normalization factor $N_i$. For the intensities, log 2 values were used in the analysis.

Data Analysis

The support vector machine (SVM) is a supervised learning method in R (45-47) that we used to classify the samples. The supervised classification was performed using a linear kernel, and the cost of constraints was set to 1, which is the default value in the R function SVM, and no attempt was performed to tune it. This absence of parameter tuning was chosen to avoid overfitting. The SVM was trained using a leave-one-out cross-validation procedure. Briefly, the training sets were generated in an iterative process in which the samples were excluded one by one. The SVM was then asked to blindly classify the left out samples as either disease or healthy, and to assign a SVM decision value, which is the signed distance to the hyperplane. No filtration on the data was done before training the SVM, i.e. all antibodies used on the microarray were included in the analysis. Further, a receiver operating characteristics (ROC) curve, as constructed using the SVM decision values and the area under the curve (AUC), was calculated.

Significantly up- or down-regulated plasma proteins (p<0.05) were defined based on the relative protein levels and identified using Wilcoxon signed-rank test, log transformed and mean centered. It should be noted that the approach did not differentiate whether the observed up- or down-regulated levels of an analyte was due to an in—/decreased production or an in-/decreased consumption. The samples were visualized using Qlucore (Lund, Sweden) or R (heat maps).

Results

Profiling of SLE and SSc Serum Proteomes

First, we determined the serum proteome profiles of SLE and SSc, and compared them to that of the healthy controls. The top≤25 significantly (p<0.05) expressed non-redundant analytes are shown as heat maps in FIG. 1. While only 4 analytes (e.g. IFN-γ, and IL-4) were found to be differentially expressed in SSc (FIG. 1A), the data showed that the expression patterns of 40 analytes differed between SLE vs. controls, including both down-regulated (e.g. C1q, C3, and C5) and up-regulated analytes (e.g. IL-6, IL-10, IFN-γ and TNF-α) (FIG. 1B). It should be noted that we could not differentiate whether the observed up- and down-regulated levels of an analyte was due to an in-/decreased production or in-/decreased consumption.

In order to evaluate the ability of the set-up to differentiate SSc and SLE vs. controls based on the observed protein expression profiles, we ran a leave-one out cross-validation based on all antibodies with a SVM, and collected the decision values for all samples. These prediction values were then used to construct a ROC curve, and the AUC value was calculated (FIG. 1). The results showed that SLE vs. controls could be reasonably differentiated (AUC=0.76) (FIG. 1B), whereas SSc vs. controls could not be distinguished (AUC=0.47) (FIG. 1A).

Figure 10:
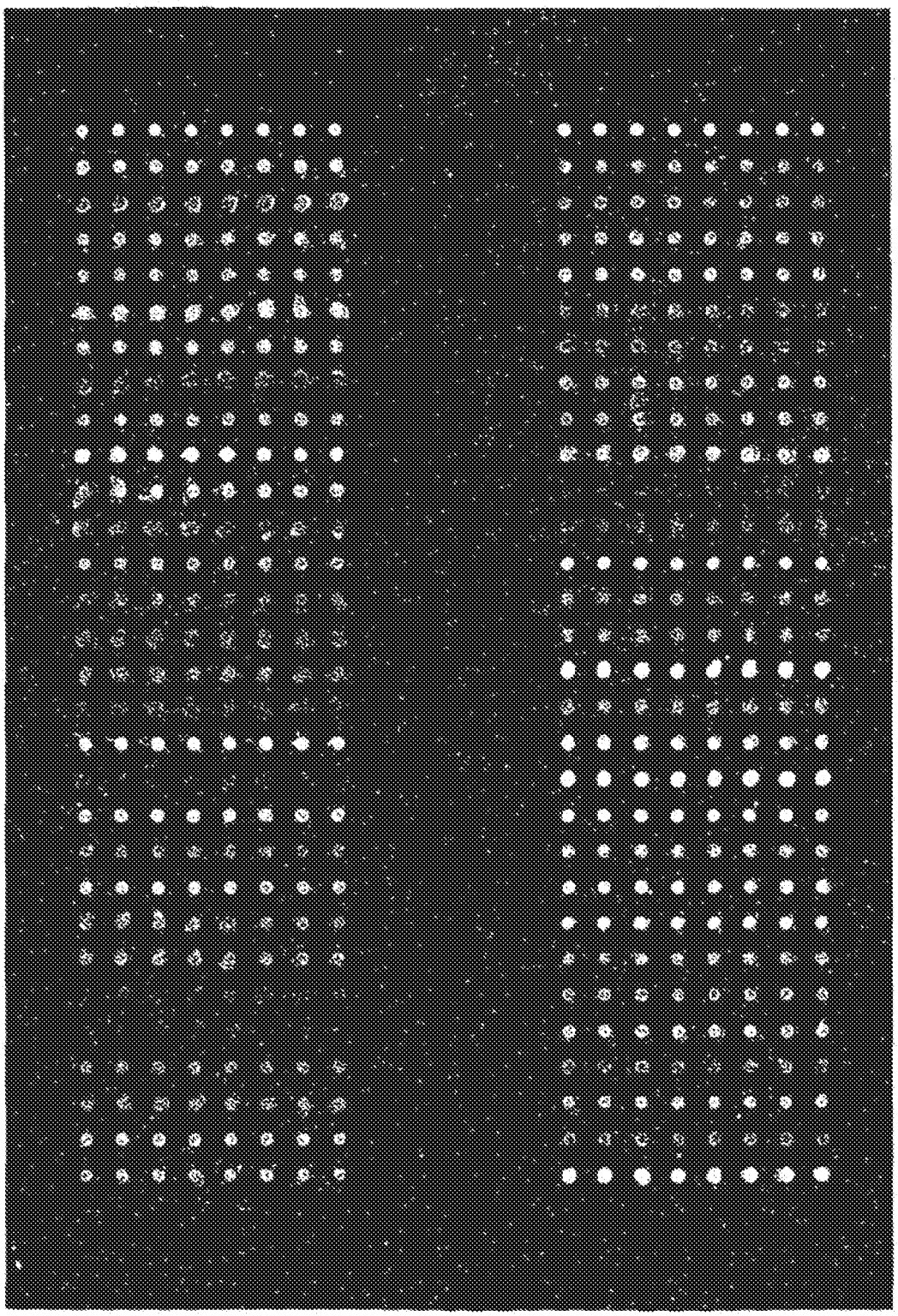
FIG. 10 depicts a scanned microarray image for a SLE sample analyzed using recombinant antibody microarrays.

Next, we examined whether a multiplexed serum profile differentiating SLE vs. SSc could be determined (FIG. 10). The data showed that 42 analytes were significantly differentially expressed of which all, but 3 (C1q, C3, and mucin-1), were up-regulated in SLE (e.g. IL-6, IL-12, IFN-γ, and TNF-α). While the discriminatory power was poor (AUC=0.59) using unfiltered data, i.e. all antibodies, the AUC value was found to be 0.69 when only the differentially expressed analytes were used.

Serum Protein Profiles of SSc Phenotypic Subsets

Figure 2B:
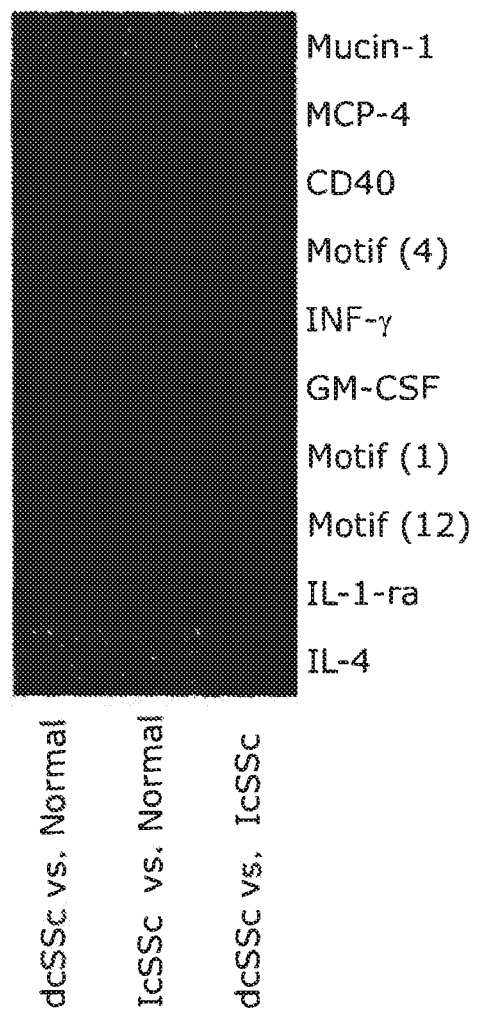
FIG. 2B depicts heat maps of significantly differentially expressed analytes.

In an attempt to further refine the serological portrait of SSc, we determined the expression profiles of the two commonly recognized phenotypic subsets, dcSSc and IcSSc (FIG. 2). The data showed that 7 significantly differentially expressed analytes were observed for dcSSc vs. controls (the most prominent being IFN-γ and IL-4), 5 for IcSSc vs. controls (e.g. IL-4, MCP-4, and CD-40), while none could be observed for dcSSc vs. IcSSc. Using unfiltered data, the phenotypic subsets could neither be differentiated from the controls nor from each other (AUC=0.50). In contrast, based on the differentially expressed analytes only, both dcSSc (AUC=0.71) and IcSSc (AUC=0.90) could be distinguished from the controls.

Classification of SLE

We then determined the serum protein profile of three phenotypic subsets of SLE grouped according to increased disease severity, SLE1<SLE2<SLE3, and compared them with that of the controls (FIG. 3). The results showed that the number of differentially expressed analytes (15<28<44) and AUC values (0.55<0.67<0.99) increased with the severity of the symptoms.

In more detail, in the case of SLE1, complement proteins were found to be down-regulated (i.e. found at lower levels)

Figure 3D:
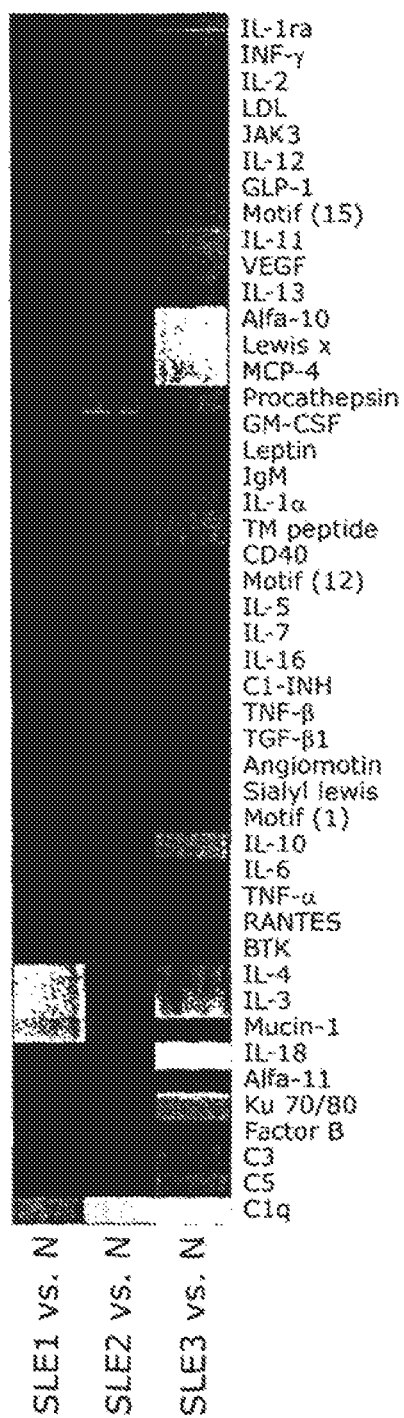
FIG. 3D depicts heat maps of significantly differentially expressed analytes.

(e.g. C1q, C3, C5, and Factor B), while several cytokines were found to be up-regulated (e.g. IL-4, IL-6, IL-10, TNF-α) (FIGS. 3A and 3D). Despite the observed differences in serum protein expression patterns, SLE1 vs. controls could not be discriminated (AUC=0.55). While complement proteins were down-regulated in SLE2 as well (e.g. C1q), the pattern of up-regulated cytokines contained a mixture of both Th1 cytokines (e.g. IL-2, IL-12, IFN-γ, and TNF-α) and Th2 cytokines (e.g. IL-6, IL-10) (FIGS. 3B and 3D). The discriminatory power of this serum biomarker profile was moderate (AUC=0.67). In contrast, SLE3 vs. controls could readily be discriminated (p=6.10$^{-7}$; AUC=0.99) with a sensitivity and specificity of 90% and 93%, respectively (FIG. 3C). Of note, in the training of the SVM, no filtration of data was made, i.e. all the measurements were included. Apart from the complement proteins (e.g. C1q, C3, and C5) and IL-18 (down-regulated), the pattern of 44 differentially expressed analytes contained mainly up-regulated cytokines, including both Th1 and Th2 cytokines (FIGS. 3C and 3D). Hence, the data showed that first candidate SLE serological biomarker signatures reflecting disease severity had been delineated using recombinant antibody microarrays.

Refined Classification of SLE Versus SSc

Considering the fact that the phenotypes of SLE were reflected in the serum profiles, we compared the molecular pattern of the phenotypic subsets of SLE with that of SSc to refine the observed serological differences between these conditions (FIG. 4). As the subsets of SSc could not be differentiated (FIG. 2), SSc was kept as one cohort. The data showed that the number of significantly differentially expressed analytes (3<36<49) and AUC values (0.40<0.69<0.98) for SLE phenotypic subsets vs. SSc increased with the severity of SLE (FIG. 4).

Figure 4D:
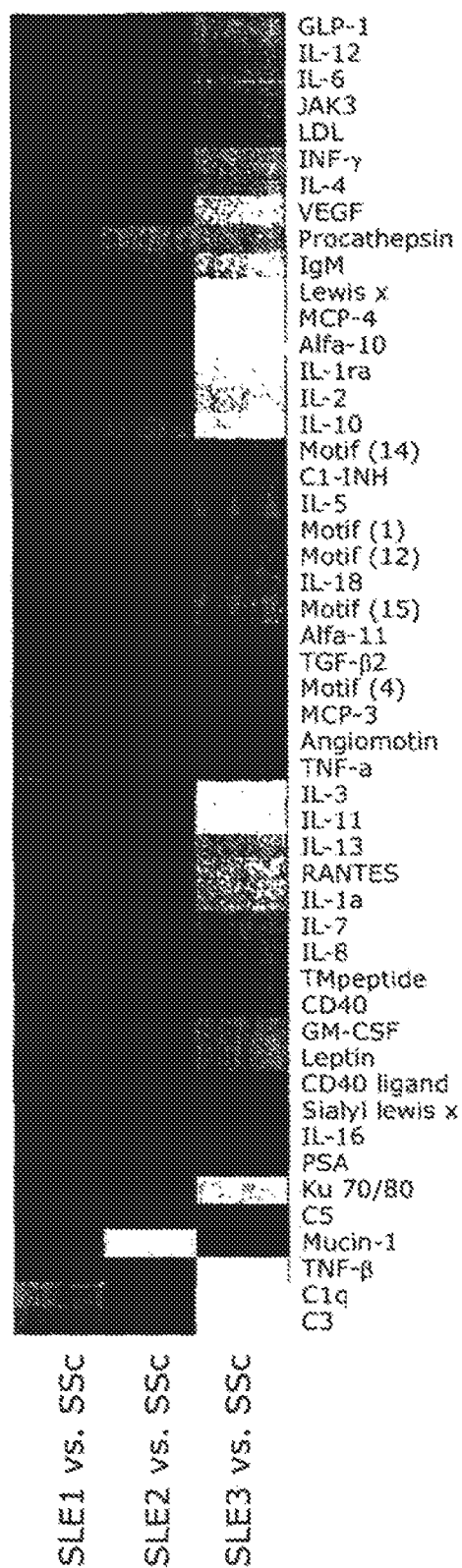
FIG. 4D depicts heat maps of significantly differentially expressed analytes.

In the case of SLE1 vs. SSc, only 3 differentially expressed analytes (C1q, C3 and TNF-α) were detected, and the cohorts could not be differentiated (AUC=0.40) (FIGS. 4A and 4D). In contrast, SLE2 vs. SSc could be differentiated (AUC=0.69), and 36 differentially expressed analytes were observed (FIGS. 4B and 4D). Except for mucin-1 and Ku 70/80 (down-regulated), a pattern of mainly up-regulated analytes was observed for SLE2, including both Th1 and Th2 cytokines. Further, SLE3 vs. SSc was readily classified (AUC=0.98; p=6.10$^{-7}$), displaying a sensitivity and specificity of 90%, respectively (FIG. 4C). While complement proteins (e.g. C1q, C3 and C5) and TNF-β were found to be down-regulated (i.e. found at lower levels), a majority of the 49 significantly differentially expressed analytes were found to be up-regulated in SLE3 and composed of a panel of both Th1 and Th2 cytokines (FIGS. 4C and 4D). Hence, the serological portraits differentiating SLE and SSc had been further deciphered and refined (cfs. FIGS. 1 and 4).

Refined Classification of SLE Reflecting Disease Severity

Figure 5A:
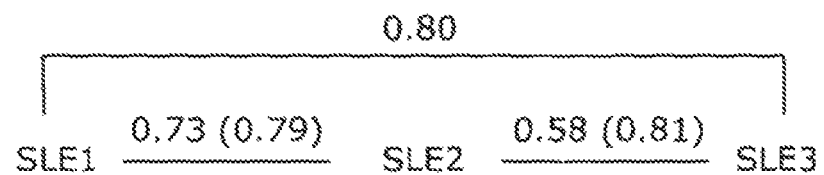
FIG. 5A depicts AUC values for classification of SLE1, SLE2, and SLE3 populations.
Figure 5B:
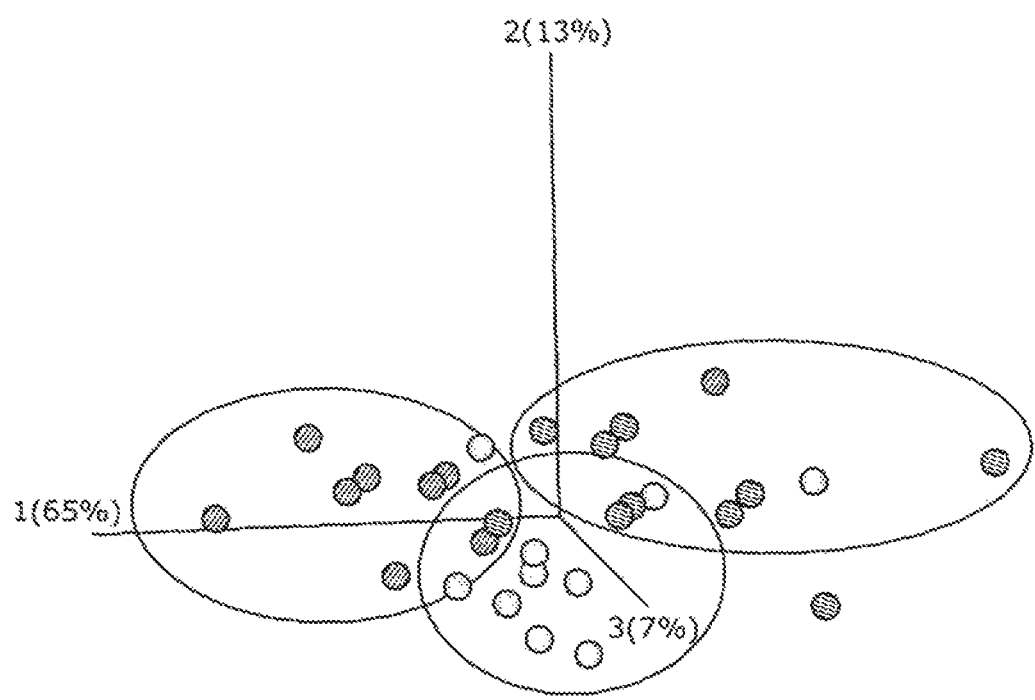
FIG. 5B depicts PCA analysis of SLE1, SLE2, and SLE3 populations.

Next, we further investigated whether the SLE samples could be classified according to disease severity, determined á priori based on an intricate pattern of clinical parameters (FIG. 5). To this end, we compared the serum protein profiles of the three SLE phenotypic subsets with each other. The results showed that SLE1 (least symptoms) vs. SLE3 (most symptoms) could be distinguished (AUC=0.80) (FIG. 5A). Moreover, SLE1 vs. SLE2 could also be separated (AUC=0.73), while SLE2 vs. SLE3 (AUC=0.58) appeared to be more similar. Notably, these comparisons were all based on unfiltered data. When only the differentially expressed analytes were used, SLE1 vs. SLE2 and SLE2 vs. SLE3 could also be classified, displaying AUC values of 0.79 and 0.81, respectively. The relationship between the 3 clinical phenotypes is further highlighted in FIG. 5B, where a principle component analysis (PCA), based on the 13 most significantly differentially expressed analytes is shown. Again, the data outlined that the three cohorts could be classified according to disease severity (phenotype), indicating that serological profiles had been delineated that could be used for phenotype classification.

Figure 5C:
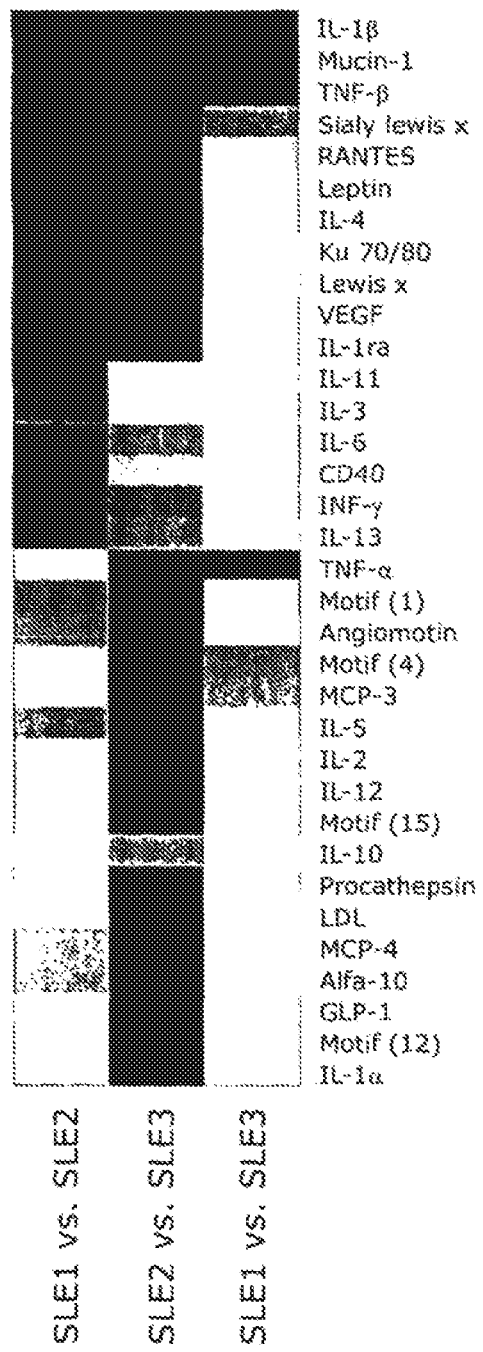
FIG. 5C depicts heat maps of significantly differentially expressed analytes.

In more detail, 23 significantly differentially expressed analytes were observed for SLE1 vs. SLE2 (FIG. 5C). Apart from 5 up-regulated analytes (e.g. IL-4 and TNF-β), the markers were down-regulated (e.g. IL-10 and IL-12) in SLE1. While only 7 differentially expressed (down-regulated) analytes (e.g. IFN-γ, IL-6, IL-10, and IL-13) were detected for SLE2 vs. SLE3, a total of 32 analytes were detected for SLE1 vs. SLE3. In the latter case, all but two analytes (IL-3 and IL-1(3), were found to be down-regulated in SLE1. Notably, the Th1 cytokines IL-12, IFN-γ and IL-2 increased as the disease progressed from SLE1 through SLE2 to SLE3, while central Th2 cytokines either decreased (IL-4) or showed moderate increase (IL-5 and IL-10) (FIG. 5D), indicating a potentially Th1 skewed immune response as the severity of SLE progressed.

Patients can be Classified According to Disease Activity

Finally, we investigated whether serological biomarker signatures reflecting SLE disease activity could de-convoluted. To this end, the SLE samples were grouped into three groups based solely on their disease activity, as reflected by their SLEDAI-2K values; low (3-6), mid (9-19) and high (22-34).

Figure 6A:
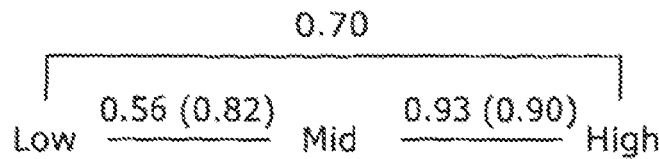
FIG. 6A depicts AUC values for classification of SLE patient populations.
Figure 6B:
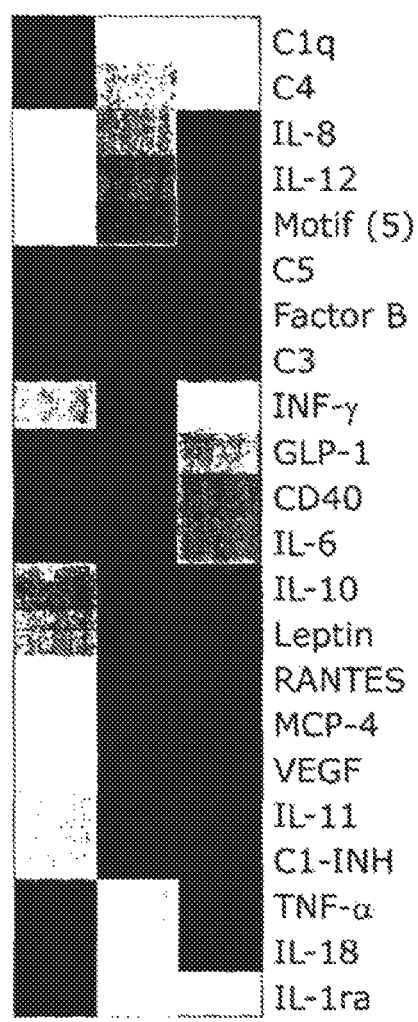
FIG. 6B depicts heat maps of significantly differentially expressed analytes.
Figure 6C:
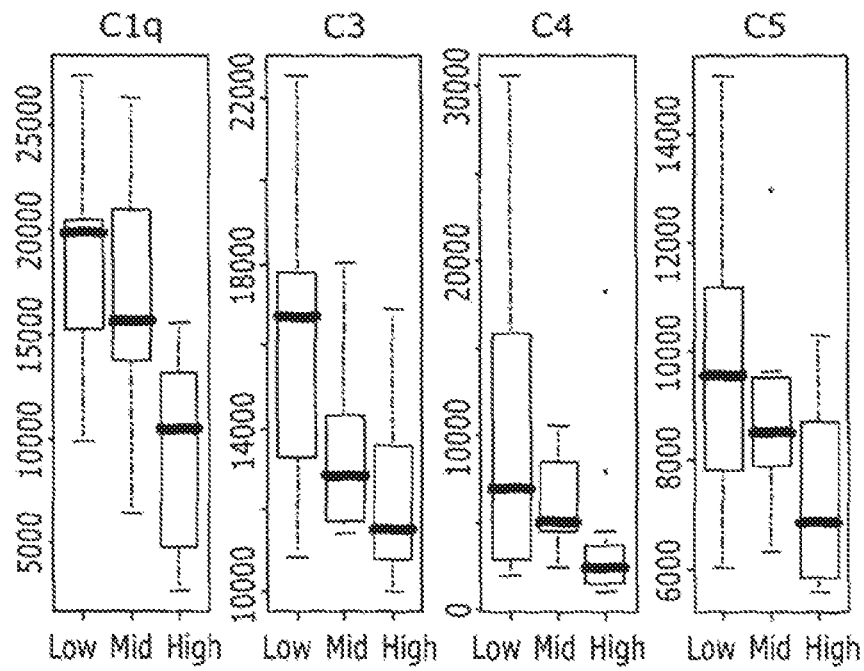
FIG. 6C depicts boxplots of microarray signal intensities for complement proteins.
Figure 6D:
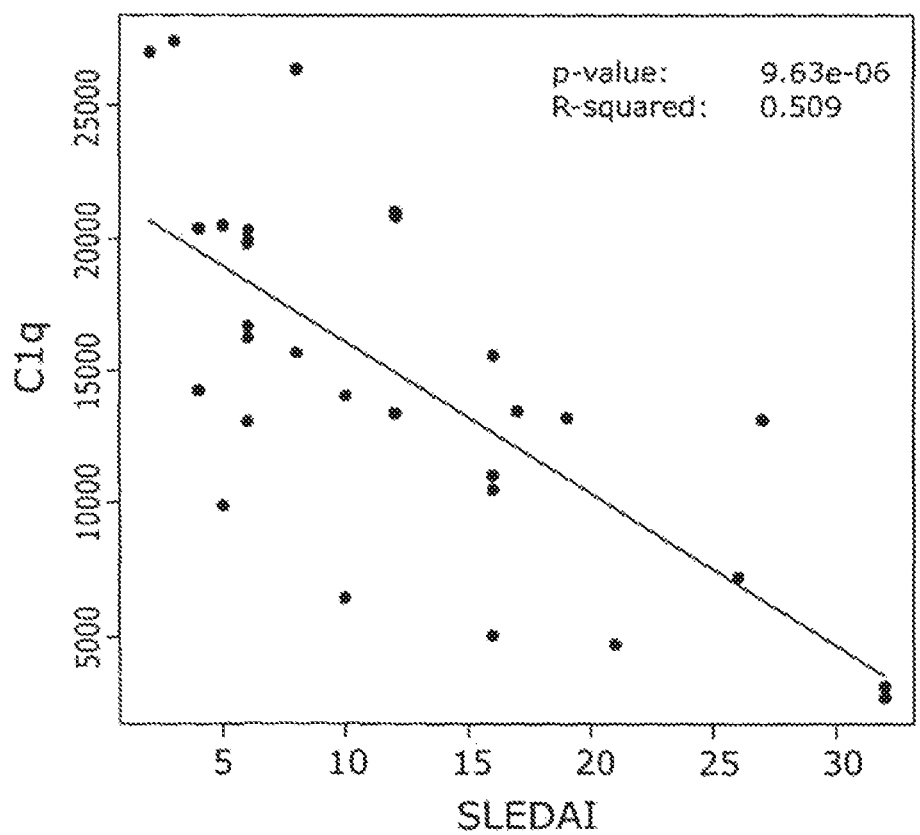
FIG. 6D depicts correlation between C1q and SLEDAI.

The antibody microarray data showed that low vs. mid SLE activity samples could not be distinguish using unfiltered data (AUC=0.53), while the AUC value was found to reach 0.82 when only the 12 differentially expressed analytes were used (FIG. 6A). Except for IL-18, only down-regulated analytes (e.g. IL-8, IL-10, IL-12, and IFN-γ) were observed in low vs. mid SLE activity (FIG. 6B). In contrast, mid vs. high SLE activity could be differentiated with very high confidence based on non-filtered data, as reflected by an AUC of 0.93 (FIG. 6A). Among the 8 differentially expressed analytes, 5 were up-regulated (e.g. C1q, C4, IL-8, and IL-12) and 3 down-regulated (IL-1-ra, IL-18, and TNF-α) in mid vs. high SLE activity (FIG. 6B). Moreover, low vs. high SLE activity could be moderately differentiated (AUC=0.70), showing a panel of 10 differentially expressed analytes, including 5 up-regulated complement proteins (C1q, C3, C4, C5 and Factor B) and 5 down-regulated analytes (e.g. CD40, IL-6, and IFN-γ) (FIGS. 6A and 6B). Focusing on the complement proteins, the trends showed that the levels of complement proteins decreased as the activity of the disease increased, as reflected by C1q, C3, C4 and C5 (FIGS. 6C and 6D). Hence, the data indicated that the first generation of multiplexed serum profiles reflecting SLE disease activity could be identified In order to eliminate any influence of the disease severity on the observed serum profiles (FIG. 5), we re-ran the analysis above focusing on the SLE3 samples only (FIG. 7). The SLE3 samples were then divided into two groups, based on their SLEDAI-2K values; low (mean 13, range 10-16) and high (mean 24, range 17-32). The data showed that the SLE3 samples could be correctly classified according to disease activity, as reflected by an AUC value of 1.00 (FIG. 7). The 20 significantly differentially expressed analytes are shown as a heatmap. Except for IL-4 and IL-1β, a pattern of mainly up-regulated analytes (e.g. CD40, IL-2, and IL-10) was observed as the disease activity increased.

In conclusion, we have shown that protein expression profiling of serum samples could be performed using recombinant antibody microarrays, enabling us to extract several unique biomarker signatures reflecting SLE and SSc and clinical subsets thereof.

Backward Variable Elimination

In order to reduce the number of antibodies used for the classification, we combined the above leave-one-out procedure with a backward elimination process for the antibodies. This process will also produce a ranking of the antibodies with the purpose of assigning low ranks to randomly correlated antibodies.

Starting with M antibodies, M datasets are created where each dataset has one antibody replaced with a constant value, which is the average value of that antibody across all samples (step 1). To evaluate each antibody's importance for classification in the current dataset, a SVM leave-one-out procedure (as described elsewhere in the Examples section) is made for each of the M datasets. Subsequently, M Kullback-Leibler divergences values are created from the SVM output, and the dataset which displayed the lowest (minimal) divergence is identified. The antibody set to a constant value in that dataset is then identified and eliminated (step 2). The datasets now contain M−1 antibodies and, M−1 new datasets are therefore created, all having one of the remaining antibodies replaced with the average. The leave-one-out testing procedure together with the SVM evaluation using constant antibodies is repeated, eliminating, in effect, the next antibody carrying the least information. The procedure is continued until only one antibody remains, resulting in a rank order for each antibody's importance in the classification of the samples currently in the dataset (step 3). This information can then be used to build antibody sub-panels of any desired length (step 4). The signature giving the lowest error is then identified and selected.

DATA from backward elimination, performed on the samples outlined in the ms are shown in Table 2 above.

Discussion

In this study, we have shown that affinity proteomics could be used to extract disease-associated serum portraits for SSc and in particular SLE reflecting disease, disease severity, disease activity, and phenotypic subsets. Although the data needs to be validated in follow-up studies, targeting larger, independent cohorts of patient samples before it could be transferred into clinical practice (29), the results clearly outlined the biomarker signatures.

SSc is a multisystem fibrotic disorder often described with a Th2 skewed, anti-inflammatory immune response, although the Th1/Th2 balance in SSc is still a matter of controversy (4, 48). Considering the fibrotic pathology of SSc, it would be natural to expect increased levels of IL-4 (Th2 cytokine) and decreased expression of IFN-γ (48). In accordance, we found IL-4 to be up-regulated and IFN-γ to be down regulated in SSc vs. controls. While this feature was prominent also for the clinical subset dcSSc, only IL-4 was up-regulated in lcSSc. To some extent this might reflect the fact that dcSSc is considered to be dominated by rapidly progressive fibrosis of the skin, lungs, and other internal organs, whereas lcSSc is dominated by vascular manifestations, and skin and organ fibrosis is generally limited and slow to progress (4).

We found very few serological markers to be differentially expressed in SSc vs. healthy controls, indicating on small differences in this particular data set. As far as we know, the association of mucin-1 and MCP-4 with SSc is a novel finding. In previous studies, serological biomarkers, exemplified by auto-antibodies, not targeted here, have been found to be an important marker of SSc (8). Other circulating serum biomarkers that have recently been indicated to be central and/or potentially differentially expressed in SSc include e.g. TGF-β, IL-1α, IL-4, IL-6, IL-10, and IL-13 (7-8, 49-51). Apart from IL-4, we were unable to replicate these previous reports. The reason for these discrepancy could include significant biological heterogeneity of SSc (3, 20, 49), the size of the patient cohorts, and/or inherent difficulties in reproducing exploratory findings generated at different sites using different proteomic approaches (29, 52-54). This clearly implicated the importance of launching large, multi-center studies using parallel complementary technologies for deciphering complex, heterogeneous diseases (8, 29, 52-54).

Diagnosing SLE and SSc is challenging, which could result in patients suffering unexplained symptoms and untreated disease (1-3, 6, 8, 20). The situation is further complicated by patients suffering from overlap syndromes in which the autoimmune disease could start out as SLE and then transforms into SSc, and vice versa (55-56). In this proof-of-concept study, distinct features and candidate serum signatures differentiating SLE and SSc were delineated. Notably, we showed that the magnitude of the observed differences coincided with the severity of SLE. Although only three analytes were found to be differentially expressed in SLE1 (least symptoms) vs. SSc, the up-regulation of TNF-α and to some extent, the decreased levels of complement proteins in SLE1 agreed well with previous reports (4, 6, 8, 12, 15, 20). As the severity of SLE increased, several other analytes that were anticipated to be over expressed in SLE (6, 12) were also detected, e.g. IL-2, IL-12 and IFN-γ. However, some analytes anticipated to be more associated with SSc than SLE (3-4, 6, 12, 20), were also found to be up-regulated in SLE vs. SSc, e.g. IL-4, IL-5, IL-10, and TGF-β, indicating that the view of describing SLE vs. SSc simply as an inflammatory phenotype vs. a fibrotic phenotype needs to be refined. In general, our data indicated a much more vigorous and broader (systemic) immune response in SLE than in SSc.

Focusing on SLE, the absence of serological biomarkers for diagnosis is significant (6). Panel(s) of auto-antibodies, erythrocyte-bound complement protein product C4d, complement receptor 1, and platelet-bound-C4d have been proposed, but their potential remains to be validated (6). Notably, we found 40 differentially expressed, non-redundant, circulating serum biomarkers, reflecting the disease, again indicating the potential of our approach. This list of variables was composed of novel markers, as well as some markers that had previously been reported to be associated with SLE, such as IL-4, IL-6, IL-10, IL-12, IFN-γ, C3 and C4 (6, 12, 57-58), further supporting our observations. It should, however, be noted that these known variables had not previously been reported in the context of a candidate signature for SLE diagnosis, but mainly as single or a few combined markers potentially reflecting disease activity (6, 12, 57-58). Further studies will be required to validate our candidate signature(s) and to extract and interpret the disease biology reflected by these serological predictors.

Subsequently, these findings were extended, and we report here a candidate serum-based signature for classifying SLE according to disease severity (15). When we compared the serum portraits of the phenotypic subsets with those of the controls, the data showed, as could be expected, that the number of differentially expressed analytes and the discriminatory power of the candidate signature increased with the severity of SLE. As for example, our results implied that SLE3, lupus nephritis, vs. controls could be differentiated with a sensitivity and specificity of 90% and 93%, respectively. Previous attempts to pin-point lupus nephritis has mainly relied on single or a few markers, although attempts have been made to identify multiplex signatures using e.g. mass spectrometry based approaches, but so far with limited success (6, 10-11, 59). Further, our data implied a somewhat skewed Th2 response in SLE1, as IL-4, IL-6, and IL-10 were found to be up-regulated, while a mixture of Th1 and Th2 cytokines were up-regulated in SLE2 and SLE3, indicating a complex pattern of cytokine expression. This could, at least to some extent, reflect the complex and intricate disease processes known to take place as the disease progresses, as mirrored by its unpredictable course and heterogeneous presentation (1-3, 7).

A refined view emerged when the molecular fingerprints of the SLE phenotypic subsets were compared with each other. Then, the data implied a potentially Th1 skewed immune response as the severity of SLE progressed, which is more in line with the common view of a strong inflammatory component in SLE (1-3, 7). The impact of being able to classify SLE into phenotypes reflecting disease severity based on a minimally invasive predictor will be central, since this is vital for therapy selection (1, 5, 11). Currently, no blood-based tests exist for such classification, further indicating the potential of using affinity proteomics for extracting key biological information from complex proteomes.

Alternating periods of flare and remission is a typical feature of SLE (1-3). The active phase of the disease often has serious consequences, like tissue and organ damages, and means to predict and monitor a flare would be instrumental for improving patient management (1-3, 11). From a clinical perspective, monitoring the activity of renal involvement in SLE is today mainly dependent on microscopic evaluation of urine, which has been shown to be associated with large methodological shortcomings (10). Other clinical laboratory variables that have been evaluated are e.g. autoantibodies, C1q, C3 and C4, although the performance of these single predictors for monitoring disease activity has varied (60-62). Despite the fact that major efforts have been made to reveal SLE-activity associated markers, ranging from traditional efforts, targeting single analytes, e.g. CD40L, to proteomic approaches (57-58, 60, 63-65), the need for additional information and a refined scenario is significant (6). Here, we have outlined candidate serological biomarker signatures for staging SLE patients based on disease activity. This list of variables was composed of novel markers and some markers that had previously been reported to be indirectly (gene-level) or directly (protein-level) associated with disease activity, such as C3, C4, IL-6, IL-8, IL-10, IL-12, and RANTES (6, 57-58, 66). In particular interferon-inducible chemokines, of which some were detected here, such as RANTES, IL-6 and IL-8, have frequently been indicated as central players to be associated with disease activity (57-58, 66-67). Notably, the first prevalidated 3-plexed signature, based on the serum levels of IFN-γ-inducible 10-kDa protein, monocyte chemotactic protein 1, and macrophage inflammatory protein 3β, was recently published (58), outlining the potential of delineating multiplexed serum predictors for staging SLE disease activity.

In order to eliminate the influence of disease severity on our ability to reflect disease activity, we focused on lupus nephritis, the most severe form of SLE, and split this group into 2 cohorts based on disease activity; SLE3-high vs. SLE3-low.

The data showed that we could differentiate the SLE3 samples based on disease activity with high confidence. Again, a mixture of novel and previously reported candidate markers (6, 57-58, 66) were delineated, further outlining our capability of reflecting disease severity. As compared to when all SLE samples were used, including patients with a broad range of disease severity, the candidate serological biomarker signatures were refined, although several variables were retained, including interferon-inducible chemokines, such as IL-8 and RANTES.

In this study, we have shown that a simple blood sample harbored significant disease-specific information reflecting complex autoimmune connective tissue diseases that could be extracted and interpreted using affinity proteomics. The results could provide new perspective on the nature of SLE, and have outlined several serological biomarker signatures reflecting disease, disease severity and disease activity. These disease predictors provide a novel means for improved clinical management of patients.

REFERENCES

1. D'Cruz, D. P., Khamashta, M. A., and Hughes, G. R. (2007) Systemic lupus erythematosus, *Lancet* 369, 587-596.
2. Rahman, A., and Isenberg, D. A. (2008) Systemic lupus erythematosus, *N. Engl. J. Med.* 358, 929-939.
3. Varga, J. (2008) Systemic sclerosis: an update, *Bull. NYU Hosp. Jt. Dis.* 66, 198-202.
4. Varga, J., and Abraham, D. (2007) Systemic sclerosis: a prototypic multisystem fibrotic disorder, *J. Clin. Invest.* 117, 557-567.
5. Eisenberg, R. (2009) Why can't we find a new treatment for SLE?, *J. Autoimm.* 32, 223-230.
6. Liu, C. C., and Ahearn, J. M. (2009) The search for lupus biomarkers, *Best Practice Res.* 23, 507-523.
Abraham, D. J., Krieg, T., Distler, J., and Distler, 0. (2009) Overview of pathogenesis of systemic sclerosis, *Rheumatology (Oxf.)* 48 *Suppl* 3, iii3-7.
8. Matucci-Cerinic, M., Steen, V., Nash, P., and Hachulla, E. (2009) The complexity of managing systemic sclerosis: screening and diagnosis, *Rheumatology (Oxf.)* 48 *Suppl* 3, iii8-13.
9. Liu, C. C., Manzi, S., and Ahearn, J. M. (2005) Biomarkers for systemic lupus erythematosus: a review and perspective, *Curr. Opin. Rheumatol.* 17, 543-549.
10. Rovin, B. H., Birmingham, D. J., Nagaraja, H. N., Yu, C. Y., and Hebert, L. A. (2007) Biomarker discovery in human SLE nephritis, *Bull. NYU Hosp. Jt. Dis.* 65, 187-193.
11. Rovin, B. H., and Zhang, X. (2009) Biomarkers for lupus nephritis: the quest continues, *Clin. J. A.m Soc. Nephrol.* 4, 1858-1865.
12. Suh, C. H., and Kim, H. A. (2008) Cytokines and their receptors as biomarkers of systemic lupus erythematosus, *Exp. Rev. Mol. Diagnos.* 8, 189-198.
13. Hochberg, M. C. (1997) Updating the American College of Rheumatology revised criteria for the classification of systemic lupus erythematosus, *Arthritis Rheum.* 40, 1725.
14. Tan, E. M., Cohen, A. S., Fries, J. F., Masi, A. T., McShane, D. J., Rothfield, N. F., Schaller, J. G., Talal, N., and Winchester, R. J. (1982) The 1982 revised criteria for the classification of systemic lupus erythematosus, *Arthritis Rheum.* 25, 1271-1277.
15. Sturfelt, G., and Sjoholm, A. G. (1984) Complement components, complement activation, and acute phase response in systemic lupus erythematosus, *Int. Arch. Allergy Appl. Immunol.* 75, 75-83.

16. Eisen, M. B., Spellman, P. T., Brown, P. O., and Botstein, D. (1998) Cluster analysis and display of genome-wide expression patterns, *Proc. Natl. Acad. Sci. U.S.A.* 95, 14863-14868.
17. Yamamoto, T. (2009) Scleroderma—pathophysiology, *Eur. J. Dermatol.* 19, 14-24.
18. Mayes, M. D., Lacey, J. V., Jr., Beebe-Dimmer, J., Gillespie, B. W., Cooper, B., Laing, T. J., and Schottenfeld, D. (2003) Prevalence, incidence, survival, and disease characteristics of systemic sclerosis in a large US population, *Arthritis Rheum.* 48, 2246-2255.
19. LeRoy, E. C., Black, C., Fleischmajer, R., Jablonska, S., Krieg, T., Medsger, T. A., Jr., Rowell, N., and Wollheim, F. (1988) Scleroderma (systemic sclerosis): classification, subsets and pathogenesis, *J. Rheumatol.* 15, 202-205.
20. Doran, J. P., and Veale, D. J. (2008) Biomarkers in systemic sclerosis, *Rheumatology (Oxf.)* 47 *Suppl* 5, v36-38.
21. Chen, C. H. (2008) Review of a current role of mass spectrometry for proteome research, *Anal. Chim. Acta* 624, 16-36.
22. Cravatt, B. F., Simon, G. M., and Yates, J. R., 3rd. (2007) The biological impact of mass-spectrometry-based proteomics, *Nature* 450, 991-1000.
23. Hanash, S. M., Pitteri, S. J., and Faca, V. M. (2008) Mining the plasma proteome for cancer biomarkers, *Nature* 452, 571-579.
24. Borrebaeck, C. A. K., and Wngren, C. (2009) Design of high-density antibody microarrays for disease proteomics: Key technological issues, *J. Proteomics* 72, 928-935.
25. Haab, B. B. (2006) Applications of antibody array platforms, *Curr. Opin. Biotechnol.* 17, 415-421.
26. Kingsmore, S. F. (2006) Multiplexed protein measurement: technologies and applications of protein and antibody arrays, *Nat. Rev. Drug Discov.* 5, 310-320.
27. Ingvarsson, J., Larsson, A., Sjoholm, A. G., Truedsson, L., Jansson, B., Borrebaeck, C. A. K., and Wingren, C. (2007) Design of recombinant antibody microarrays for serum protein profiling: targeting of complement proteins, *J. Proteome Res.* 6, 3527-3536.
28. Wingren, C., Ingvarsson, J., Dexlin, L., Szul, D., and Borrebaeck, C. A. K. (2007) Design of recombinant antibody microarrays for complex proteome analysis: choice of sample labeling-tag and solid support, *Proteomics* 7, 3055-3065.
29. Borrebaeck, C. A. K., and Wingren, C. (2009) Transferring proteomic discoveries into clinical practice, *Exp. Rev. Proteomics* 6, 11-13.
30. Carlsson, A., Wingren, C., Ingvarsson, J., Ellmark, P., Baldertorp, B., Ferno, M., Olsson, H., and Borrebaeck, C. A. K. (2008) Serum proteome profiling of metastatic breast cancer using recombinant antibody microarrays, *Eur. J. Cancer* 44, 472-480.
31. Ellmark, P., Ingvarsson, J., Carlsson, A., Lundin, B. S., Wingren, C., and Borrebaeck, C. A. K. (2006) Identification of protein expression signatures associated with *Helicobacter pylori* infection and gastric adenocarcinoma using recombinant antibody microarrays, *Mol. Cell. Proteomics* 5, 1638-1646.
32. Ingvarsson, J., Wngren, C., Carlsson, A., Ellmark, P., Wahren, B., Engstrom, G., Harmenberg, U., Krogh, M., Peterson, C., and Borrebaeck, C. A. K. (2008) Detection of pancreatic cancer using antibody microarray-based serum protein profiling, *Proteomics* 8, 2211-2219.
33. Carlsson, A., Persson, O., Ingvarsson, J., Widegren, B., Salford, L., Borrebaeck, C. A. K., and Wingren, C. (2010) Plasma protein profiling reveals biomarker patterns associated with prognosis and therapy selection in glioblastoma multiforme pateints, *Proteomics—Clin. Appl.* 4, 591-602.
34. Hesselstrand, R., Scheja, A., and Akesson, A. (1998) Mortality and causes of death in a Swedish series of systemic sclerosis patients, *Ann. Rheumatic Dis.* 57, 682-686.
35. Stahl-Hallengren, C., Jonsen, A., Nived, O., and Sturfelt, G. (2000) Incidence studies of systemic lupus erythematosus in Southern Sweden: increasing age, decreasing frequency of renal manifestations and good prognosis, *J. Rheumatol.* 27, 685-691.
36. Masi, A. T. (1988) Classification of systemic sclerosis (scleroderma): relationship of cutaneous subgroups in early disease to outcome and serologic reactivity, *J. Rheumatol.* 15, 894-898.
37. Wuttge, D. M., Wildt, M., Geborek, P., Wollheim, F. A., Scheja, A., and Akesson, A. (2007) Serum IL-15 in patients with early systemic sclerosis: a potential novel marker of lung disease, *Arthritis Res. Ther.* 9, R85.
38. Gladman, D. D., Ibanez, D., and Urowitz, M. B. (2002) Systemic lupus erythematosus disease activity index 2000, *J. Rheumatol.* 29, 288-291.
39. Wingren, C., and Borrebaeck, C. A. K. (2008) Antibody microarray analysis of directly labelled complex proteomes, *Curr. Opin. Biotechnol.* 19, 55-61.
40. Soderlind, E., Strandberg, L., Jirholt, P., Kobayashi, N., Alexeiva, V., Aberg, A. M., Nilsson, A., Jansson, B., Ohlin, M., Wingren, C., Danielsson, L., Carlsson, R., and Borrebaeck, C. A. K. (2000) Recombining germline-derived CDR sequences for creating diverse single-framework antibody libraries, *Nat. Biotechnol.* 18, 852-856.
41. Borrebaeck, C. A. K., and Wingren, C. (2007) High-throughput proteomics using antibody microarrays: an update, *Exp. Rev. Mol. Diagnos.* 7, 673-686.
42. Wingren, C., and Borrebaeck, C. A. K. (2006) Antibody microarrays: current status and key technological advances, *Omics* 10, 411-427.
43. Wingren, C., and Borrebaeck, C. A. K. (2007) Progress in miniaturization of protein arrays—a step closer to high-density nanoarrays, *Drug Discov. Today* 12, 813-819.
44. Wingren, C., Ingvarsson, J., Lindstedt, M., and Borrebaeck, C. A. K. (2003) Recombinant antibody microarrays—a viable option?, *Nat. Biotechnol.* 21, 223.
45. Chih-chung, C., and Chih-Jen, L. (2007) LIBSVM: a library for support vector machines., http/:www.csie.ntu.edu.tw/cjlin/libsvm.
46. Cristianini, N., and Shawe-Taylor, J. (2000) An introduction to support vector machines and other kernel-based learning methods, Cambridge Univeristy Press.
47. Ihaka, R., and Gentleman, R. (1996) A language for data analysis and graphics, *J. Comp. Graph. Stat.* 5, 299-314.
48. Atamas, S. P., and White, B. (2003) Cytokine regulation of pulmonary fibrosis in scleroderma, *Cytokine Growth Factor Rev.* 14, 537-550.
49. Beirne, P., Pantelidis, P., Charles, P., Wells, A. U., Abraham, D. J., Denton, C. P., Welsh, K. I., Shah, P. L., du Bois, R. M., and Kelleher, P. (2009) Multiplex immune serum biomarker profiling in sarcoidosis and systemic sclerosis, *Eur. Respir. J.* 34, 1376-1382.
50. Duan, H., Fleming, J., Pritchard, D. K., Amon, L. M., Xue, J., Arnett, H. A., Chen, G., Breen, P., Buckner, J. H., Molitor, J. A., Elkon, K. B., and Schwartz, S. M. (2008) Combined analysis of monocyte and lymphocyte messen- 51. Radstake, T. R., van Bon, L., Broen, J., Hussiani, A., Hesselstrand, R., Wuttge, D. M., Deng, Y., Simms, R., Lubberts, E., and Lafyatis, R. (2009) The pronounced Th17 profile in systemic sclerosis (SSc) together with intracellular expression of TGFbeta and IFNgamma distinguishes SSc phenotypes, *PloS one* 4, e5903.
52. Gerszten, R. E., Accurso, F., Bernard, G. R., Caprioli, R. M., Klee, E. W., Klee, G. G., Kullo, I., Laguna, T. A., Roth, F. P., Sabatine, M., Srinivas, P., Wang, T. J., and Ware, L. B. (2008) Challenges in translating plasma proteomics from bench to bedside: update from the NHLBI Clinical Proteomics Programs, *Am. J. Physiol.* 295, L16-22.
53. Hanash, S. (2003) Disease proteomics, *Nature* 422, 226-232.
54. Omenn, G. S., States, D. J., Adamski, M., Blackwell, T. W., Menon, R., Hermjakob, H., Apweiler, R., Haab, B. B., Simpson, R. J., Eddes, J. S., Kapp, E. A., Moritz, R. L., Chan, D. W., Rai, A. J., Admon, A., Aebersold, R., Eng, J., Hancock, W. S., Hefta, S. A., Meyer, H., Paik, Y. K., Yoo, J. S., Ping, P., Pounds, J., Adkins, J., Qian, X., Wang, R., Wasinger, V., Wu, C. Y., Zhao, X., Zeng, R., Archakov, A., Tsugita, A., Beer, I., Pandey, A., Pisano, M., Andrews, P., Tammen, H., Speicher, D. W., and Hanash, S. M. (2005) Overview of the HUPO Plasma Proteome Project: results from the pilot phase with 35 collaborating laboratories and multiple analytical groups, generating a core dataset of 3020 proteins and a publicly-available database, *Proteomics* 5, 3226-3245.
55. Lorber, M., Gershwin, M. E., and Shoenfeld, Y. (1994) The coexistence of systemic lupus erythematosus with other autoimmune diseases: the kaleidoscope of autoimmunity, *Sem. Arthritis and Rheum.* 24, 105-113.
56. Pope, J. E. (2002) Scleroderma overlap syndromes, *Curr. Opin. Rheumatol.* 14, 704-710.
57. Bauer, J. W., Baechler, E. C., Petri, M., Batliwalla, F. M., Crawford, D., Ortmann, W. A., Espe, K. J., Li, W., Patel, D. D., Gregersen, P. K., and Behrens, T. W. (2006) Elevated serum levels of interferon-regulated chemokines are biomarkers for active human systemic lupus erythematosus, *PLoS Med.* 3, e491.
58. Bauer, J. W., Petri, M., Batliwalla, F. M., Koeuth, T., Wilson, J., Slattery, C., Panoskaltsis-Mortari, A., Gregersen, P. K., Behrens, T. W., and Baechler, E. C. (2009) Interferon-regulated chemokines as biomarkers of systemic lupus erythematosus disease activity: a validation study, *Arthritis Rheum.* 60, 3098-3107.
59. Suzuki, M., Ross, G. F., Wers, K., Nelson, S., Bennett, M., Passo, M. H., Devarajan, P., and Brunner, H. I. (2007) Identification of a urinary proteomic signature for lupus nephritis in children, *Ped. Nephol.* 22, 2047-2057.
60. Villegas-Zambrano, N., Martinez-Taboada, V. M., Bolivar, A., San Martin, M., Alvarez, L., Marin, M. J., and Lopez-Hoyos, M. (2009) Correlation between clinical activity and serological markers in a wide cohort of patients with systemic lupus erythematosus: an eight-year prospective study, *Ann. N.Y. Acad. Sci.* 1173, 60-66.
61. Sjoholm, A. G., Martensson, U., and Sturfelt, G. (1997) Serial analysis of autoantibody responses to the collagen-like region of C1q, collagen type II, and double stranded DNA in patients with systemic lupus erythematosus, *J. Rheumatol.* 24, 871-878.
62. Sturfelt, G., Sjoholm, A. G., and Svensson, B. (1983) Complement components, C1 activation and disease activity in SLE, *Int. Arch. Allergy Appl. Immunol.* 70, 12-18.
63. Mosley, K., Tam, F. W., Edwards, R. J., Crozier, J., Pusey, C. D., and Lightstone, L. (2006) Urinary proteomic profiles distinguish between active and inactive lupus nephritis, *Rheumatology (Oxf.)* 45, 1497-1504.
64. Pitashny, M., Schwartz, N., Qing, X., Hojaili, B., Aranow, C., Mackay, M., and Putterman, C. (2007) Urinary lipocalin-2 is associated with renal disease activity in human lupus nephritis, *Arthritis Rheum.* 56, 1894-1903.
65. Urquizu-Padilla, M., Balada, E., Cortes, F., Perez, E. H., Vilardell-Tarres, M., and Ordi-Ros, J. (2009) Serum levels of soluble CD40 ligand at flare and at remission in patients with systemic lupus erythematosus, *J. Rheumatol.* 36, 953-960.
66. Fu, Q., Chen, X., Cui, H., Guo, Y., Chen, J., Shen, N., and Bao, C. (2008) Association of elevated transcript levels of interferon-inducible chemokines with disease activity and organ damage in systemic lupus erythematosus patients, *Arthritis Res. Ther.* 10, R112.
67. Pascual, V., Farkas, L., and Banchereau, J. (2006) Systemic lupus erythematosus: all roads lead to type I interferons, *Curr. Opin. Immunol.* 18, 676-682.

Abbreviations

ACR—American college of rheumatology
AUC—area under the curve
CV—coefficient of variance
dcSSc—diffuse cutaneous SSc
lcSSc—limited cutaneous SSc
NHS—N-hydroxylsulfosuccinimide ester group
PCA—principle component analysis
ROC—receiver operating characteristics
scFv—single-chain fragment variable
SLE—systemic lupus erythematosus
SLEDAI-2K—SLE disease activity index
SSc—systemic sclerosis
SVM—support vector machine

EXAMPLE B

Introduction

Serum profiling using antibody microarrays can facilitate our understanding of disease by identifying panels of disease-specific biomarkers, thereby enhancing our ability to diagnose and treat such diseases. Here, we performed a comprehensive survey of serologic proteome in human SLE using our in-house developed human recombinant single-chain fragment variable (scFv) microarray technology. We have indentified 20 serum biomarker signatures, that discriminates between SLE patients and healthy controls with a high specificity and sensitivity. When targeting the individual clinical subgroups of SLE we observed that differences in protein expression patterns depend on the activity and severity of the SLE symptoms. Serum proteome of patients with SLE glomerulonephritis (SLE3) showed the most significant difference compared to healthy one. Furthermore, the levels of some serum proteins, were highly correlated with clinical measure of disease activity (SLEDAI), as well as with data reported in other studies. Taken together, these data suggest that antibody microarray analysis of complex proteomes can provide a better understanding of autoimmune disease pathogenesis, improved patients classification, more effective treatment, enabling personalized medicine.

Systematic lupus erythematosus is a chronic, multisystem autoimmune disease with a broad range of possible clinical and serological presentations. It is characterized by a loss of tolerance to host antigens and development of pathogenic autoantibodies that damage target organs, such as skin, lungs, heart, joints, brain and kidney. SLE is estimated to worldwide affect 0.1% of the population, predominantly women between their 20s and early 40s [1]. The pathogenesis of SLE is still largely unknown, although both genetic and environmental factors are probably involved in disease development. Establishing a diagnosis of lupus is difficult and relies on a list of 11 classification criteria, that were developed over 20 years ago by the American College of Rheumatology (ACR) (Table 6) [2]. These classification criteria can guide the initial asssesment of the patient with SLE but are not sufficient to adequately diagnose SLE, pin-point the phenotypic subclasses of SLE with high confidence, or to predict disease flares and remissions. The latter features are key criteria for optimizing the treatment of the diseases. In fact, there are no multiplexed serum biomarker signatures yet at hand to resolve these key unmet clinical issues. Hence, there is an urgent need to identify biomarkers that will improve diagnosis, classification and prognosis of SLE.

Recent studies have outlined the potential of proteomic applications based on recombinant scFv antibody microarray within the field of biomarkers discovery [3-5]. This novel technology enable us to directly profile non-fractionated complex serum and plasma proteomes in a highly multiplexed, rapid and sensitive manner, while consuming only microliter amounts of samples [6-8]. By probing the antibody-based microarrays with serum from diseased individuals and comparing obtained profiles to those of healthy individuals we could indentify a wide spectrum of reactive proteins that are putative biomarkers. These disease-associated protein signatures, when validated, can be used for disease diagnosing and classifying, determining drug efficacy and toxicity, monitoring disease progression or response to therapy.

In a recent proof-of-concept study we have analyzed a cohort of well defined serum samples from SLE patients and healthy controls using our in-house recombinant antibody microarray technology platform (Carlsson et al., ms in prep.). The results demonstrated that we have identified the first candidate serum biomarker signatures for SLE diagnosing and clinical subgroup classification, which reflect disease activity and flare status, thereof based on a simple blood test.

In this study, we have based on a our previous work (Carlsson et al ms in prep), constructed a focussed array using a limited set of 58 scFv probes against selected analytes, including key cytokines, chemokines and complement factors. Serum sample from SLE patients and phenotypic subgroups thereof and healthy controls were analyzed and compared. The overal aim of the current study was to validate and further extend our initial findings for improved diagnosis, prognosis, and SLE phenotype classification. The specific aims included: (i) evaluation of the diagnostic and prognostic utility of our candidate biomarker signatures as well as its potential for identification of phenotypic subtypes of SLE; (ii) delineation of molecular serum profiles of SLE in relation to disease activity. The results showed that an array of antibody fragments, specific for immunoregulatory proteins, could discriminate between human serum proteomes derived from either SLE patients or healthy individuals with high specificity and sensitivity, based on a simple blood test.

Materials and Methods
Serum Samples

In total, 110 serum samples from 70 patients, supplied by Assoc. Prof. G. Sturfelt (the Department of Rheumatology, Lund University Hospital, Lund, Sweden), were included in this study (Table 7). The samples were collected from 40 patients suffering from systematic lupus erythematosus who met four or more of the American College of Rheumatology (ACR) classification criteria and 30 healthy control subjects.

SLE samples were divided into two cohorts. The first study cohort consisted of 20 well-defined serum samples collected from 10 different SLE patients. The matched samples drawn from the same patient differed with respect to apoptis inducing capacity—representing a high vs. low apoptosis inducing. This SLE cohort was used for evaluating whether serum protein signature associated with apoptosis could be delineated.

The second SLE cohort, consisting 30 patients was used for pin-pointing candidate predictor biomarker signatures for SLE and its clinical subgroups. Two matched samples were provided per patient, drawn at different occasions. One sample was collected at a time of flare (high SLEDAI score) and the other at a time of no flare (low SLEDAI score).

The SLEDAI consist of 24 well defined, weighted clinical and laboratory variables grouped into nine organ systems. Each of the items is scored from 0 to 8 on the basis of severity. The index is calculated by summing all variables that were present within the previous ten days. On the basis of SLEDAI scores following disease activity categories have been defined: no activity (SLEDAI=0), mild activity (SLEDAI=1-5), moderate activity (SLEDAI=6-10), high activity (SLEDAI=11-19), and very high activity (SLEDAI 20) [9].

Labeling of Serum Samples Serum samples were biotinylated using EZ-Link Sulfo-NHC-LC-Biotin (Pierce, Rockford, Ill., USA) according to previously optimised labeling protocol for serum proteomes [8].

Briefly, serum aliquots were centifuged at 16,000 xg for 20 min at 4° C. and diluted 1:45 in phosphate-buffered saline (PBS), resulting in a protein concentration of about 2 mg/ml. Next the sulfo-NHS-biotin was added to a final concentration of 10 mM and the samples were kept on ice for 2 h, with gentle vortexing every 20 min. Unconjugated biotin was removed by extensive dialysys against PBS for 72 h at 4° C. using Slide-A-Lyzer Mini Dialysis Units MCWO of 3.5 kDa (Pierce, Rockford, Ill., USA). Finally, the samples were aliquoted and stored at −20° C. util further use.

Antibodies

Based on previous work (Carlsson et al. ms in prep.) a limited set of 57 human recombinant scFv antibody fragments specific for differentially expressed serum proteins were selected from the n-CoDeR library, and kindly provided by BioInvent Internatinal AB (Lund, Sweden). Furthermore, a mouse monoclonal antibody to INF-α was purchased from AbCam (Cambridge, United Kingdom) and used in this study. The specificities and final concentration of the recombinant antibodies used in this study are listed in Table 8.

Production and Purification of scFv

All scFv probes were produced in *Escherichia coli*. Briefly, cell cultures were grown over night in 5 ml 2×yeast extract tryptone (YT)-medium (Sigma-Aldrich, St Louis, Mo.) containing 100 µg/ml ampicillin (Amp) at 37° C., 200 rpm and then diluted 1:100 in 2×YT medium with Amp. Cultures were incubated at 37° C. until $OD_{600}$ reached 0.9-1.0. The expression of scFv was induced by addition of 1 mM isopropyl β-D-thiogalactopyranoside (IPTG) (Saveen Werner A B, Malmo, Sweden) and followed by over night incubation at 37° C., 200 rpm.

The scFv antibodies were purified from supernatant using nickel-nitrilotriacetic acid (Ni-NTA) agarose affinity chromatography (Qiagen, Hilden, Germany). In more detail, the cells cultures were centifuged at 15,000 xg for 20 min at 4° C. and supernatants were concentrated to 20 ml using Amicon Ultra Centifugal filter device, molecular weight cut off (MCWO) of 10 kDa (Millipore Corporation Billerica, Mass., USA). Next the supernatants were dialyzed over night at 4° C. against lysis buffer (50 mM $NaH_2PO_4 \times H_2O$, 300 mM NaCl, 10 mM imidazole, pH 8.0) using a MWCO of 12-14 kDa (Spectra/Por, Spectrum Laboratories Inc., Ranch Dominguez, Calif., USA). Dialyzed scFv preparations were incubated with 1 ml of Ni-NTA agarose gel (Qiagen, Hilden, Germany), previously equilibrated with 20 ml of lysis buffer, on rocking table overnight at 4° C. The Ni-NTA matrix with bound scFv was paked into 10 ml columns (BioRad, Hercules, Calif., USA) and subsequently washed 3 times with washing buffer (50 mM sodium phosphate, 300 mM NaCl, 20 mM imidazol, pH 8.0). Bound molecules were eluted with 1 ml elution buffer (50 mM $NaH_2PO_4 \times H_2O$, 300 mM NaCl, 20 mM imidazole, pH 8.0) and extensively dialyzed against PBS overnight at 4° C. Produced scFvs were stored at 4° C. prior to use. In order to prevent bacterial growth 0.05% (v/v) azide was added (BDH Laboratory, Poole, England).

The concentration of purified proteins was determined by measuring the absorbance at 280 nm using NanoDrop ND-1000 (Saveen Werner A B, Malmö, Sweden). The integrity and purity of the scFvs antiobodies was evaluated by means of 10% SDS-PAGE (Invitrogen, Carlsbad, USA).

SDS-PAGE

Proteins were separated on 10% NuPAGE Novex Bis-Tris gels (Invitrogen, Carlsbad, USA). The samples were mixed with sample buffer and reducing agent according to instructions from the supplier, and then heated to 95° C. for 5 min and loaded on a gel. The separation was performed at 120 V for about 1 hour and followed by gel staining with Simply Blue SafeStain (Invitrogen, Carlsbad, USA) for 1 hour. Next, the gel was destained with $H_2O$ over night and photographed using GelDoc XR (Bio Rad).

Fabrication and Handling of scFv Microarrays

The scFv microarrays were produced using a non-contact printer (sciFLEXARRAYER S11, Scienion AG, Berlin, Germany). The purified scFv antibodies were arrayed by dispensing 1 drop (330 pL/drop) at each position onto black polymer MaxiSorb slides (NUNC, Roskilde, Denmark). In order to ensure adequate statistics eight replicates of each scFv-clone were arrayed. In total 58 antibodies were prined per microarray oriented in two columns with 8×29 spots per each.

A hydrophobic barrier was created around the individual microarray using a Dakocytomation pen (Dakocytomation, Glostrup, Denmark). The arrays were blocked with 250 μl 5% (w/v) fat-free milk powder (Semper A B, Sundbyberg, Sweden) in PBS over night in a humidity chamber at room temperature (RT). Next, the arrays were washed four times with 200 μl 0.05% Tween-20 in PBS (PBS-T) and then icubated with 250 μl of the bitinylated sample previously diluted 1:10 (resulting in a final serum dilution of 1:450) in 1% (w/v) fat-free milk powder and 1% Tween in PBS (PBS-MT) for 1 h. Subsequently the arrays were washed four times with PBS-T and incubated with 250 μl of 1 μg/ml Alexa-647 (Invitrogen, Carlsbad, USA) conjugated streptavidin diluted in PBS-MT for 1 h. Finally, the arrays were washed four times as previously and immediately dried with nitrogen gas stream.

Spotting Optimization of scFv Microarrays

Serial dilutions of 57 scFv antibodies were performed resulting in 3 different concentrations of each probe (0.5 mg/ml, 0.3 mg/ml and 0.1 mg/ml) and spotted onto 6 black polymer MaxiSorb slides. In total 136 probes were printed per microarray oriented in two columns with 8×68 spots per each. The handling of arrays was performed using two different set-ups: previously described manual handling (3 slides) and automatic handling (3 slides) using the Protein-Array Workstation (Perkin Elmer, USA). As a test samples we used 2 serum samples obtained from SLE patients and 1 serum sample from a healthy object. Optimal probes spotting concentrations were determined by comparing the spot morphology (e.g. quality, intensity etc).

Analysis and Normalization of scFv Microarrays

The arrays were scanned at 5 μm resolution with a confocal microarray scanner (ScanArray Express, Perkin Elmer Life & Analytical Sciences) using five different scanner settings. The intensity of each spot was quantified by the fixed circle method with ScanArray Express software V 4.0 (Perkin Elmer Life & Analytical Sciences). The local background was subtracted and the two lowest and highest replicates were automatically excluded to avoid any possible local defects. For further data analysis the mean value of the remaining four replicates was used.

Before chip-to-chip normalization data from different scanning settings for each sample were scaled to one particural setting (PMT gain—90%, laser power—100%) and only nonsaturated spots were used for further analysis. Normalization of the datasets was performed by using a semi-global normalization approach [4], conseptually similar to the normalization developed for DNA microarrays. The coefficient of variation (CV) for each scFv was calculated calculated and then ranked. Fifteen percentage of the scFv antiobodies displaying the lowest CV-values over all samples (corresponding to 9 analytes: C5 (2), Factor B, TGF-β1(2), MCP-3 (2), Lewisx (2), Leptin, IL-6 (1), INF-γ (1), IL-2 (1)) were used to calculated a chip-to-chip normalization factor by the formula $Ni=Si/\mu$, where the Si is the sum of the signal intensities for 9 scFvs for each sample and μ is the average of Si from all samples. Each dataset generated from one sample was divided with the Ni factor.

Data classification was carried out with a support vector machine tool (SVM) using a linear kernel. Briefly, a SVM is a supervised learning method able to find a hyperplane which optimally separates positive and negative members of a given training set. A test sample is classified depending on which side of separating plane is located. The cost of constraints was set to one, which is the default value in the R function SVM, and no attempt was made to tune it. The lack of parameter tuning was chosen to avoid overfitting and to make the classification procedure more evident. Significantly up- or down-regulated plasma proteins (p<0.05) were identified using Wilcoxon test, log transformed and mean centered. The samples were then visualized using Qlucore (Lund, Sweden) or hierarchically clustered and visualized as a heat map, using Cluster and TreeView [10].

Results

In this study, we report the second use of large-scale recombinant antibody microarrays for serum proteome profiling of systematic lupus erythematosus. The arrays were composed of 57 human recombinant scFv antibody fragments and one mouse monoclonal full-length antibody directed against 40 different analytes such as cytokines, chemokines, complement and growth factors. In total, 80 SLE serum samples and 30 healthy control samples were analyzed.

Microarray Spotting Optimization

Figure 8:
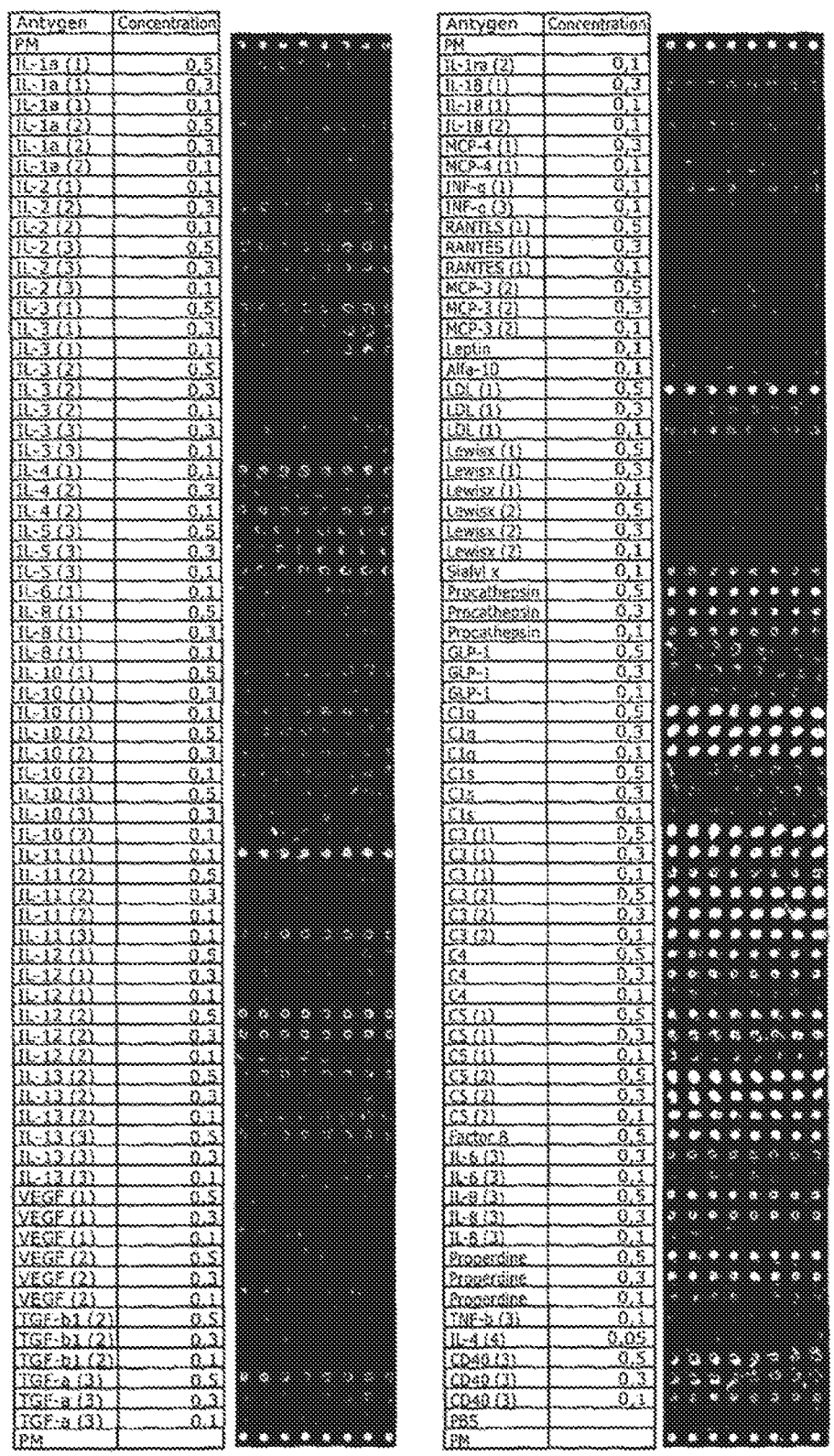
FIG. 8 depicts a scanned representative microarray image of SLE sample used for spotting optimization protocol.
Figure 9A:
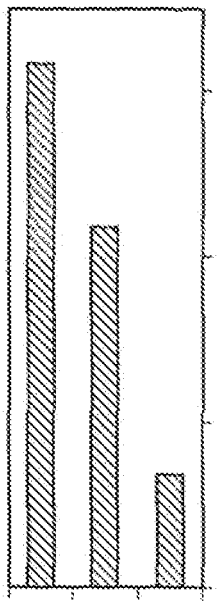
FIGS. 9A-9D depict effect of different probe concentrations on spot morphologies and signal intensities.
Figure 9B:
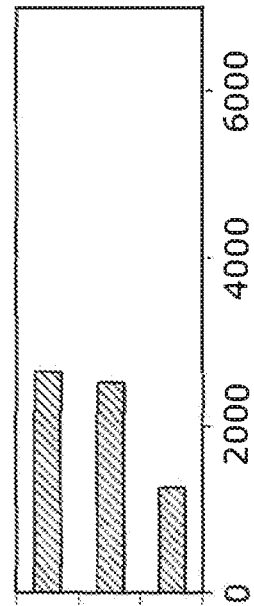
Figure 9C:
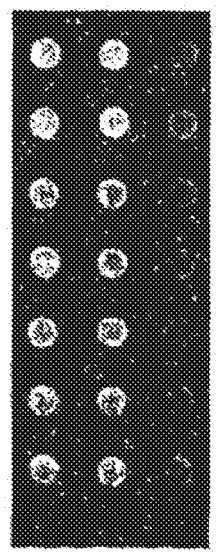
Figure 9D:
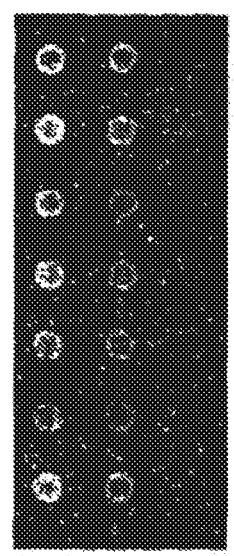

In order to improve spot morphology and uniformity, as well as the overall array quality (e.g. signal intensity and variability), the optimal concentration of the array antibodies was determined. It was performed by testing serial dilutions (equivalent to protein concentrations from 0.1 to 0.5 mg/ml) of all probes for printing and then analyzing 3 randomly selected samples (2 from SLE patients and 1 healthy individual). A representative microarray image of obtained is shown in FIG. 8. The results showed that a variation in spot morphology and signal intensity could be observed that was dependent on the concentration of the spotted antibody.

In FIG. 9, a close-up is shown for two representative clones (against C4 and IL-8). Further, the results also indicated that too high probe concentration resulted in widespread smearing effects. The optimal antibody concentration for spotting thus had to be determined for each antibody used (Table 8).

Link Between Serum Protein Levels and Apoptosis in Systematic Lupus Erythematosus To identify candidate serum protein(s) directly or indirectly associated with the know SLE serum apoptosis inducing capacity, the correlation between the serum levels of 40 different analytes and the a priori known apoptosis inducing capacity was investigated using our in-house antibody microarray technology platform. The analysis were performed on the I cohort of SLE samples, in which 20 serum samples were drawn from 10 SLE patients in well defined manner. Of the two matched samples, one exhibited high and and one low apoptosis inducing capacity. The results showed that no correlation could be found between serum protein expression and degree of apoptosis (data not shown). Hence, the 40 targeted serum analytes could be eliminated from the list of tentative candidates, suggesting that other factor(s) must be involved in the observed apoptosis in SLE patients.

Classification of Systematic Lupus Erythematosus Patients by Serum Protein Profiling To test ability of the microarray set-up to discriminate between SLE patients vs. healthy individuals based on a simple blood test, we compared their serum protein expression profiles determined using our recombinant antibody microarrays. A representative microarray image of SLE sera is shown in FIG. 10, demonstrating improved uniformity and homogeneity of spot morphologies and dynamic signal intensities.

The microarray expression data obtained from SLE samples collected from the time-point of flare (high SLE-DAI score) and all healthy control samples were analyzed in leave-one-out cross validation with a Support Vector Machine (SVM). The decision values for each sample were generated and displayed in terms of a receiver operator curve (ROC). The results showed that the SLE patients vs. healthy controls could be classified with an area under the curve (AUC) of 0.92 (FIG. 11A). This indicated the existence of a clear difference between the SLE and the normal serum proteome in the protein signatures analyzed by the microarray platform. The decision value is the output of predictor, and samples with a prediction value below a threshold are classified as SLE. The threshold parameterizes the trade-off between sensitivity and specificity and is often set to zero. The 30 systematic lupus erythematosus samples obtained decision values in the range from −1.3 to 4.2, and the healthy controls in the interval from −3.9 to 1.3. Thus, with a threshold value of zero, the sensitivity and specificity in our dataset was 83% and 86% respectively. The top 20 ranked analytes are shown as a heat map, further illustrating the diagnostic potential of the candidate signature observed (FIG. 11B).

In an attempt to further evaluate the observed differences between SLE patients and healthy controls, the analysis was re-run using the second sample from the same SLE patients collected when the disease was inactive (low SLEDAI value). In FIG. 11C a ROC curve was constructed, using the decision values produced by SVM. The results indicated that also samples collected from SLE patients during remission time could be discriminated from healthy controls with an ROC area of 0.88. The differentially expressed serum protein analytes are shown in FIG. 11D. Taken together, the results further supported the diagnostic potential of our approach.

In order to examine classification in more detail, the serum protein expression profiles of the different SLE subgroups (SLE1, SLE2, SLE3) vs. healthy subjects were compared. The results demonstrated that the different subsets of SLE: SLE1, SLE2 and SLE3 could be separated from healthy controls with an AUC of 0.76, 0.66 and 0.96 respectively (data not shown). Notably, the SLE1 subgroup (less clinical symptoms) could be classified from healthy controls with higher degree of confidence than the SLE2 cohort (more clinical symptoms). This observation could, however, most likely be explained by the fact that the SLE1 patients displayed higher SLEDAI scores than the SLE2 patients, i.e. in line with the previous observation that SLE patients with active disease were more readily separated from healthy controls than SLE patients in remission.

Figure 12A:
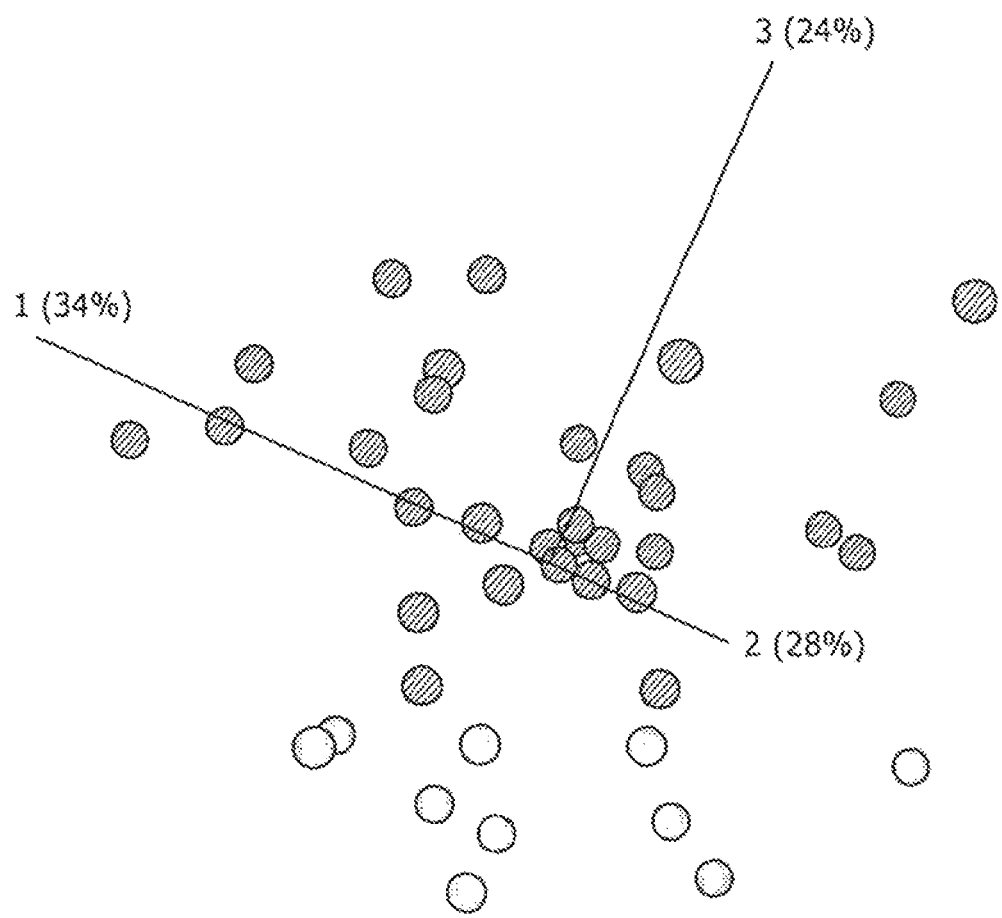
FIG. 12A depicts a multidimensional plot based on 4 significant analytes.
Figure 12B:
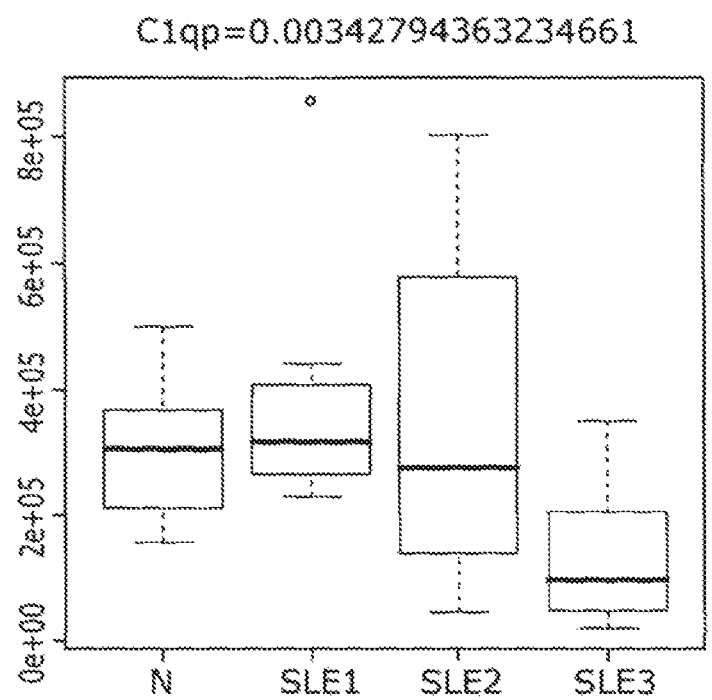
FIG. 12B depicts a box plot demonstrating signal intensities for C1q.
Figure 12C:
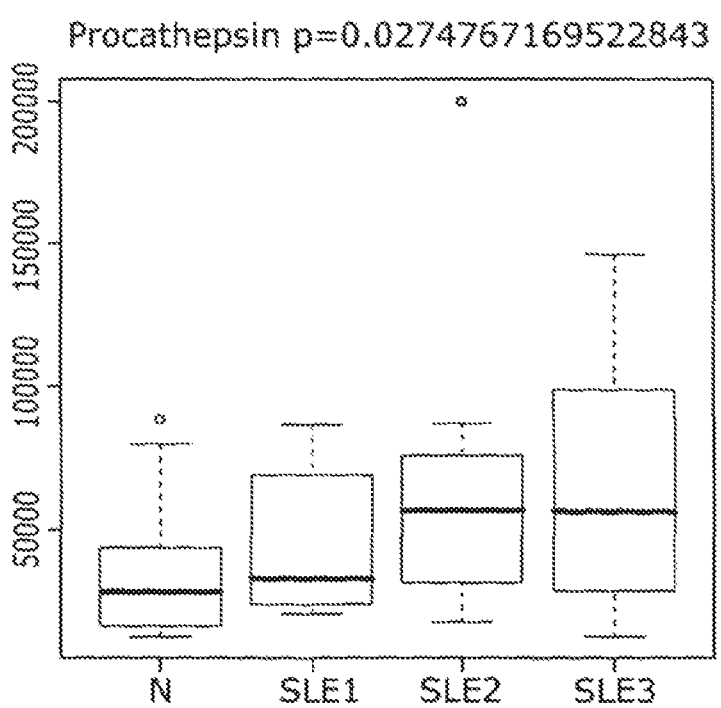
FIG. 12C depicts a box plot demonstrating signal intensities for Procathepsin.
Figure 14A:
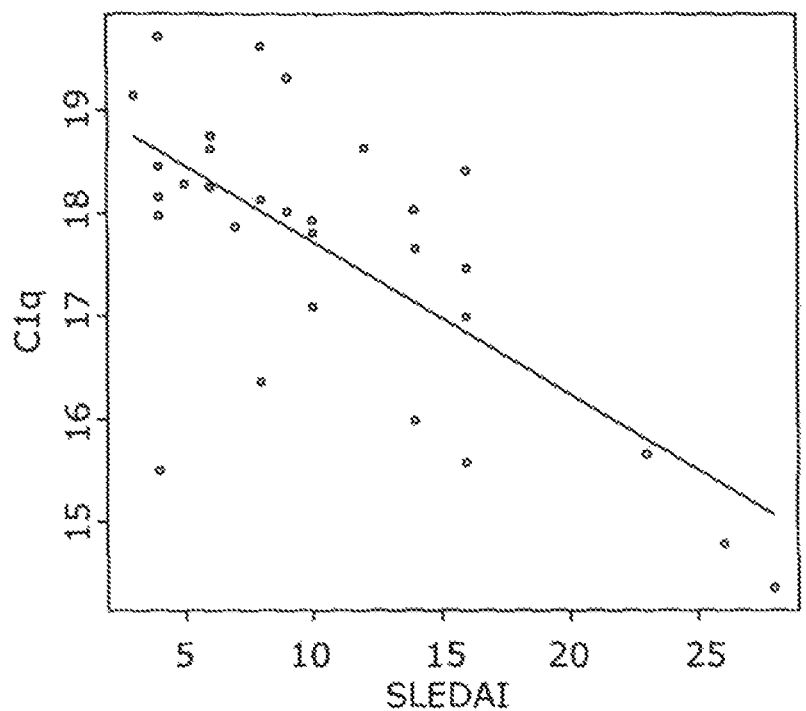
FIGS. 14A-14D depict correlation between SLE activity and serum levels of C1q, INF-α, TNF-α, and IL-1α(2).
Figure 14B:
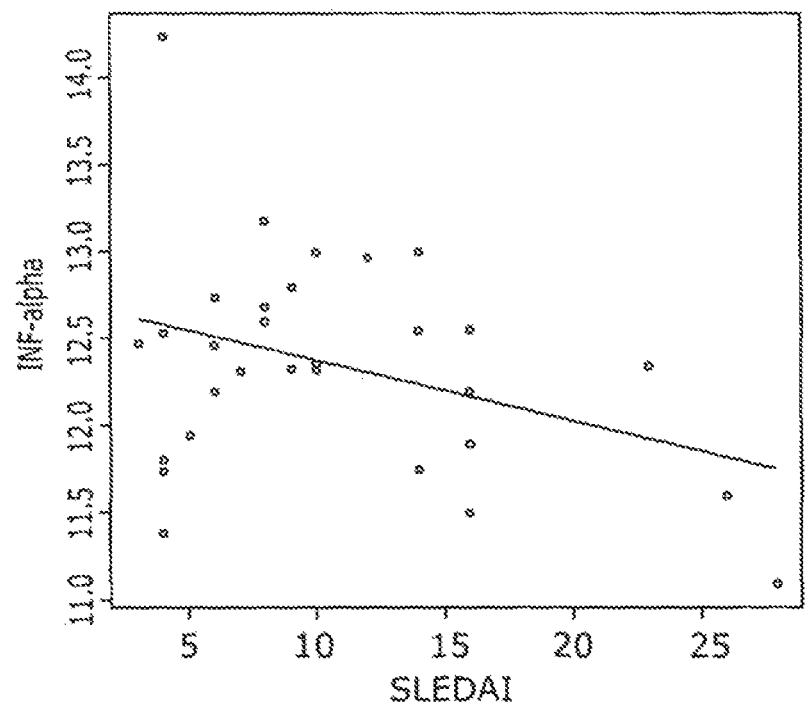
Figure 14C:
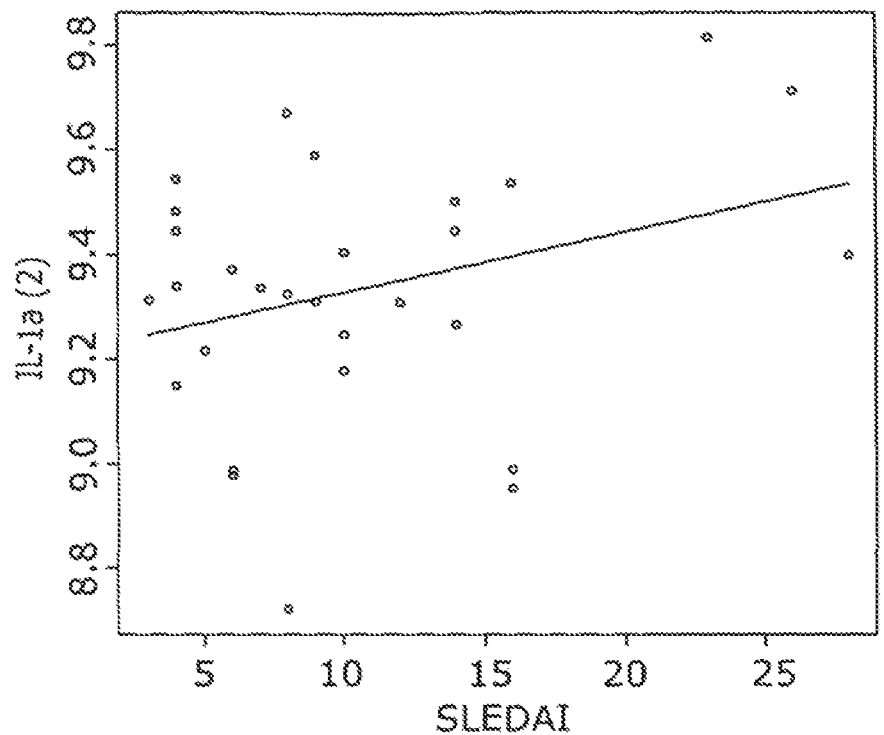
Figure 14D:
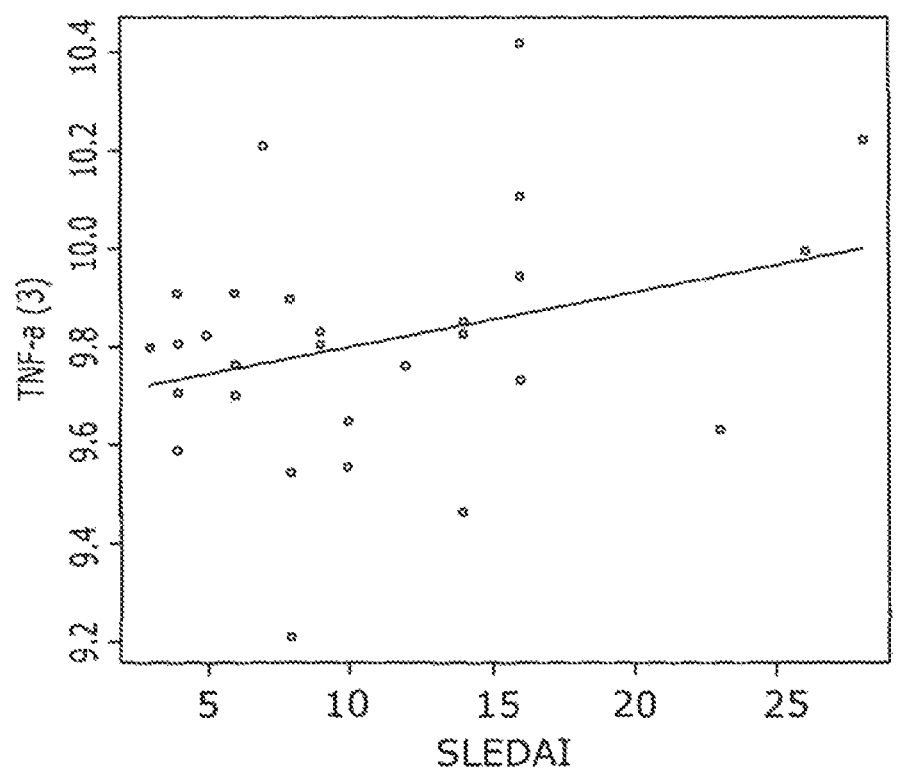

As could be expected, SLE3, the most severe disease stage with kidney involvement, displayed most significant differences vs. healthy controls. This is illustrated in FIG. 12A by a principle component analysis plot.

Several serum analytes were significantly up- and down-regulated in the samples from each of the SLE subgroups, including procathepsin (FIG. 5B), cytokines such as IL-13, TNF-α and complement factors C1q (FIG. 5C), C5. Interestingly, increased production of C5 was observed in the serum from all SLE sub-sets accompanied by decreased levels of another complement proteins, such as C1q, C3, C4.

Sub-Classification of Systematic Lupus Erythematosus Patient by Serum Protein Profiling In attempt to examine utility of our recombinant antibody microarray platform for separating the SLE patient sub phenotypes, we compared three cohorts of SLE individuals consisting of 10 patients in each. Patients were divided into subgroups: SLE1, SLE2 and SLE3 based on the results of laboratory test, clinical outcomes and disease severity. The result showed that that similar expression profiles were obtained for SLE1 vs. SLE2 and SLE 2 vs. SLE3, respectively. Hence, these co-horts could not be differentiated with confidence. However, the SLE1 patients vs. SLE3 individuals could readily be stratified using our microarray set-up, displaying an area under the curve of 0.87 (FIG. 13). Most interestingly, when analyzing the individual proteins, a consensus patterns in the expression levels of LDL(1) and C1q was observed in all of the subgroups (data not shown).

Correlation Between Serum Proteins Levels and SLE Activity

Monitoring of protein expression profiles related to SLE phenotype and disease activity is instrumental in order to optimize the treatment of this incurable disease. To this end, the serum protein profiles were compared between matched samples from the same individual when at flare or at remission. Patients were classified as active when they had an SLEDAI score of 4 or greater, and inactive when the SLEDAI score was 0.

Comparison of serum protein expression profiles for patients with active disease vs. inactive disease, showed that several analytes were found to be up-regulated as well as down-regulated (Table 9). As for example, LDL, INF-γ and IL-1α were found to be up-regulated, while Lewisx and CD40 were found to be down-regulated.

The comparison of elevated serum protein levels according to SLEDAI scores was performed in order to examine theirs correlation with disease activity. Relatively high negative correlations were observed between C1q (pvalue=0.00002) and disease activity. Moreover, the concentrations of INF-α was lower in patients with very active SLE form and negatively correlated with SLEDAI scores. On the other hand, TNF-α and IL-1α(2) were found to exhibit a positive correlation with disease activity, what is shown in FIG. 14.

Taken together, we have successfully confirmed the previous findings that our human recombinant antibody microarray technology platform could be used for differentiating SLE vs. healthy controls, taken the next step towards a novel improved way for SLE diagnosis. In a similar fashion we have again demonstrated that the technology can be used for delineating candidate biomarker signatures associated with the SLE phenotype and disease activity, providing a novel means of pin-pointing these key criteria before initiating therapy.

REFERENCES

1. D'Cruz, D. P., M. A. Khamashta, and G. R. Hughes, *Systemic lupus erythematosus*. Lancet, 2007. 369(9561): 587-96.
2. Hochberg, M. C., *Updating the American College of Rheumatology revised criteria for the classification of systemic lupus erythematosus*. Arthritis Rheum, 1997. 40(9):1725.
3. Ingvarsson, J., et al., *Detection of pancreatic cancer using antibody microarray-based serum protein profiling*. Proteomics, 2008. 8(11):2211-9.
4. Carlsson, A., et al., *Serum proteome profiling of metastatic breast cancer using recombinant antibody microarrays*. Eur J Cancer, 2008. 44(3):472-80.
5. Ellmark, P., et al., *Identification of protein expression signatures associated with Helicobacter pylori infection and gastric adenocarcinoma using recombinant antibody microarrays*. Mol Cell Proteomics, 2006. 5(9):1638-46.
6. Borrebaeck, C. A. and C. Wngren, *High-throughput proteomics using antibody microarrays: an update*. Expert Rev Mol Diagn, 2007. 7(5):673-86.
Borrebaeck, C. A. and C. Wingren, *Design of high-density antibody microarrays for disease proteomics: Key technological issues*. J Proteomics, 2009.
8. Wingren, C., et al., *Design of recombinant antibody microarrays for complex proteome analysis: choice of sample labeling-tag and solid support*. Proteomics, 2007. 7(17):3055-65.
9. Cook, R. J., et al., *Prediction of short term mortality in systemic lupus erythematosus with time dependent measures of disease activity*. J Rheumatol, 2000. 27(8):1892-5.
10. Eisen, M. B., et al., *Cluster analysis and display of genome-wide expression patterns*. Proc Natl Acad Sci USA, 1998. 95:14863-8.

EXAMPLE C

Systemic lupus erythematosus (SLE) is a potentially fatal autoimmune multisystem disease, characterized by chronic inflammations of various tissues and internal organs. The underlying mechanisms, not yet fully understood, involve immunological deficiencies as well as genetic, environmental and hormonal factors (1). Due to heterogeneous symptoms and an unpredictable course of disease, the management of SLE is one of the greatest challenges within the field of rheumatology (2).

Associated with poor long-term prognosis (3), SLE nephritis is one of the more severe manifestations of SLE that occurs in about 50% of all patients (1). Commonly, it is a result of antibody-antigen complex deposition in the glomerulus, i.e. the capillary network of the nephron, where the initial blood filtration takes place. These complexes activate the complement system which mediates local inflammatory events (4).

Standard treatment involves immunosuppressive agent cyclophosphamide. However, associated with side-effects and limited efficacy (5), such therapy would improve if the occurrence of flares could be predicted and readily monitored (6). For example, the development of prediction models (e.g. Generalized Estimating Equation framework) relies on biomarkers that can reflect renal flares (6). Furthermore, these biomarkers would aid in the assessment of disease activity, which is crucial in the clinical management of SLE (1). Despite considerable efforts, few biomarkers have been validated and adopted for clinical decision-making (2) (6) (7). New biomarkers may also reveal the underlying mechanisms and present potential drug targets that can act more specifically on the immune system, improving long-term prognosis (2). Conclusively, there is a great clinical need to validate and define new biomarkers for SLE nephritis flare.

The use of recombinant antibody microarrays to discover disease-related protein expression has, after methodological advances (8) (9), been successfully demonstrated (10) (11). Based on the highly specific antibody-antigen interaction, this approach enables rapid, multiplexed and high through-put profiling of crude proteomes (12) (13). The obtained biomarker signatures may, when validated, lead to better diagnostics, patient classification and prognosis (14).

The potential of analyzing SLE serum samples with our in-house recombinant antibody microarray platform for the purpose of patient classification and biomarker discovery has previously been demonstrated (Magdalena Kasendra, 2007) (Carlsson et al, manuscript in preparation). Here, expression profiles from different subclasses of SLE patients along with healthy individuals were compared, revealing biomarker panels capable of reflecting disease, disease activity and phenotypic subsets.

Beside serum, urine is another prospective source for biomarker discovery and classification, especially in lupus nephritis due to its renal involvement. In addition, sample collection is very easy and non-intrusive. A previous study (Karolina Olsson, 2007) has shown that urine can be analyzed with our in-house developed antibody microarray platform.

Thus, the aim of this study was to extend the previous efforts and confirm as well as pin-point novel biomarkers of SLE nephritis flare, and further investigate the classification potential of both serum and urine in terms of disease activity.

This was done on all samples, divided into two cohorts according to disease activity, as well as individually paired samples, i.e. two samples from within a patient, taken at different occasions and disease activity. Further protocol developments were made to optimize the labeling and analysis of urine.

We used our in-house developed recombinant antibody microarray, targeting 63 proteins related to the immune system (e.g. cytokines, complement, chemokines) with 147 single-chain fragment variables (scFvs), to analyze 59 serum samples matched with 58 urine samples.

We were able to demonstrate promising possibilities of classifying lupus nephritis according to disease activity with urine as sample format, using leave-one-out cross validation with a Support Vector Machine (SVM). These findings allow to flare prediction and improved assessment of disease activity. Ultimately, this will contribute to an optimized treatment of SLE nephritis patients.

Materials and Methods

Clinical Samples

This study was approved by the regional ethics review board in Lund, Sweden. All clinical samples were kindly provided by Prof. G. Sturfelt (Dept. of Rheumatology, Lund University Hospital, Lund, Sweden. In total, 58 serum and 57 urine samples from 27 patients were used (Table 14). All but one serum sample was matched with a urine sample, collected on the same day or within a few days time. From each patient, 1 to 4 samples were collected over time (time span up to 4 years). The SLE disease activity (DA) was denoted as 1 (active) or 0 (inactive). Analyzed urine samples contained inhibitors (benzamidinium chloride, EDTA, sodiumazide and tris(hydroxymethyl)-aminoethane), added at the time of collection. The samples were stored at −20° C. until further use.

Production and Purification of scFvs

All scFvs were produced in genetically modified $E.\ coli$, kindly provided by Bioinvent International AB (Lund, Sweden) as frozen glycerol stocks. A complete list of the scFvs are found in Table 10. Briefly, 5 ml 2×yeast extract tryptone (YT) medium (Sigma-Aldrich, St Louis, Mo.), containing 100 µg/ml ampicillin (Saveen Werner, Malmö, Sweden), were inoculated with glycerol stocks (stored at −80° C.) and incubated over night (220 rpm, 37° C.). 2 ml was transferred to 500 ml flasks, containing 100 ml 2×YT and 100 µg/ml ampicillin, and cultivated (220 rpm, 37° C.) until $OD_{600}$ reached 0.9-1.0. At that time, production of scFv was induced through the addition of 200 µl 0.5M isopropyl β-D-thiogalactopyranoside (IPTG) (Saveen Werner, Malmö, Sweden). The culture was incubated over night (37° C., 220 rpm). The solution was centrifuged (10,000 rpm, 4° C., 20 min) and the cell pellet discarded, while the supernatant was concentrated from 100 ml to 20 ml using Amicon Ultra 15 ml centrifugal filter device (MWCO 10,000) (Millipore Corporation Billerica, Mass., USA). The supernatant was then dialyzed (MWCO 12-14,000) against lysis buffer (10 mM imidazole, pH 8) over night at 4° C. One ml nickel-nitrilotriacetic acid ($Ni^{2+}$-NTA) agarose suspension (Qiagen, Hilden, Germany), previously equilibrated with 20 ml lysis buffer, was incubated with the scFv solution on rocking table over night at 4° C. Next, the suspension was added to 10 ml columns and washed with 3×5 ml washing buffer (20 mM imidazole, pH 8). One ml elution buffer (250 mM imidazole, pH 8) was used to elute any bound scFv. The eluted fraction was then dialyzed (MWCO 12-14,000) against PBS overnight at 4° C. The protein concentration was measured using NanoDrop ND-1000 (NanoDrop Technologies, Wilmington, USA), and the degree of purity was evaluated with SDS-PAGE (Invitrogen, Carlsbad, USA). Finally, azide was added to a final concentration of 0.05% (w/v) to prevent bacterial growth. The scFv preparations were stored at 4° C. until further use.

Sample Labeling

Biotinylation of crude serum was carried out according to previously optimized protocol (Wngren 2007), using EZ-Link Sulfo-NHC-LC-Biotin (PIERCE). Briefly, frozen serum samples were thawed on ice and centrifuged (13,000 rpm, 20 min, 4° C.). The samples were diluted 45 times in PBS to obtain suitable protein concentration (about 2 mg/ml). Biotin was added to a final concentration of 0.6 mM (molar ratio biotin:protein 15:1). The solution was stored on ice for 2 h, and vortexed every 20 min. Unconjugated biotin was eliminated through extensive dialysis against PBS (72 h, 4° C.), using Slide-A-Lyzer Mini Dialysis Units (MWCO 3,500) (Rockford, Ill., USA). Finally, labeled serum samples were aliquoted and stored at −20° C.

The labeling of crude urine was based on a recent study (Karolina Olsson, 2007) with some modifications. In order to optimize the pH during the labeling (pH 7 to 9), the possibility of dialyzing urine against PBS prior to labeling was investigated. In addition, ways to reduce dilution of urine samples during the dialysis step were explored.

Adjusting pH through dialysis against PBS was found to yield stronger signal intensities (data not shown). Furthermore, using larger volumes of urine during dialysis was found to reduce dilution. These procedures were adopted for the main study.

Briefly, frozen urine samples were thawed on ice and centrifuged (13,000 rpm, 20 min, 4° C.). The samples (200 µl) were dialyzed at 4° C. over night against PBS using Slide-A-Lyzer Mini Dialysis Units (MWCO 3,500). Biotin was then added to a final concentration of 0.45 mM (molar ratio biotin:protein 45:1). The solution was stored on ice for 2 h, while vortexed every 20 min. Unconjugated biotin was eliminated through extensive dialysis against PBS (72 h, 4° C.), using Slide-A-Lyzer Mini Dialysis Units (MWCO 3,500). Finally, labeled urine samples were stored as aliquots at −20° C.

Array Fabrication

The antibody microarrays were produced using sciFLEX-ARRAYER (Scienion, Berlin, Germany) and black polymer MaxiSorb slides (NUNC, Roskilde, Denmark). Each spot was generated from a single drop (330 µl) of purified scFv solution. To ensure sufficient statistics, each clone was spotted in 8 replicates. In total, 147 scFvs, twelve position markers (10 µg/ml SA-AL647 in PBS) and nine negative controls (PBS) were dispensed on each array. The same layout was used for both serum and urine. Two arrays were fitted on each slide.

The scFvs were diluted to suitable concentrations (range 0.05-0.4 mg/ml) according to previous optimization regarding serum samples (Magdalena Kasendra, 2009). For urine, spotting with high concentration of scFv (≤0.4 mg/ml) was compared to previously optimized concentrations for serum samples. Arrays spotted with 1 and 2 droplets were also compared.

Figure 15A:
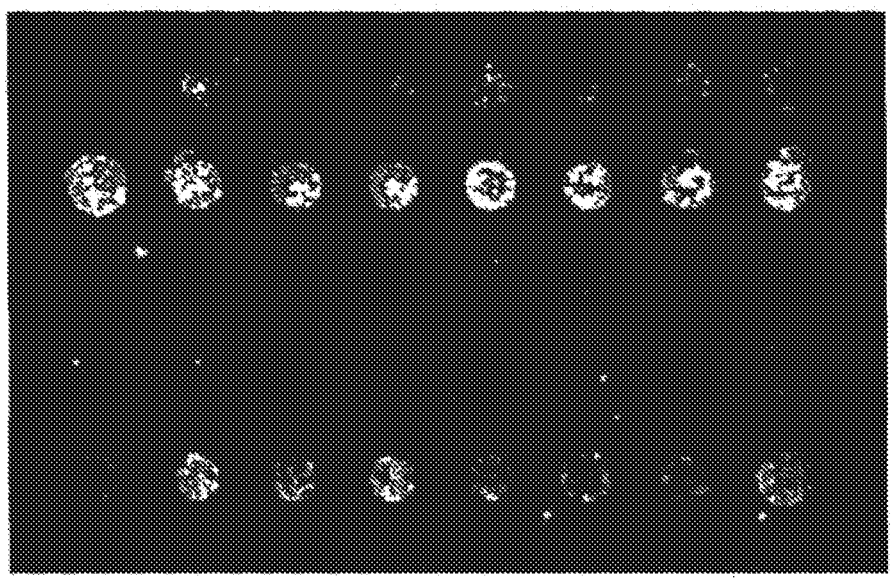
FIGS. 15A-15B depict spot morphology comparison.
Figure 15B:
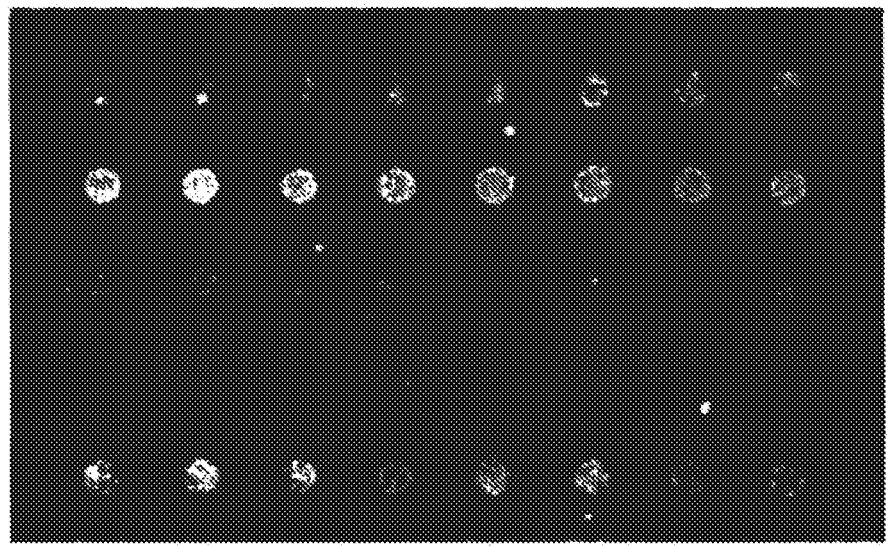

High concentration of scFvs (≤1.4 mg/ml) was found to give better signal intensities when analyzing urine (data not shown). Using only one drop when spotting was found superior due to slightly better spot morphology, as shown in FIG. 15. Hence, these settings were used during array fabrication in the subsequent studies.

A hydrophobic pen was used to draw a barrier around the arrays. Next, each array was blocked with 400 µl 5% (w/v) fat-free milk powder in PBS and incubated over night in a humidity chamber at room temperature. The arrays were then washed two times, with 200 µl 0.05% (v/v) Tween in PBS. 200 µl of the previously labeled samples, either serum or urine preparations, were added and incubated for 1 h. When using serum, samples were first diluted 1:9 in 1% (w/v) fat-free milk powder and 1% (v/v) Tween in PBS (1% PBS-MT). Urine samples were diluted with 2% PBS-MT in a ratio of 3:1. The arrays were then washed two times with 200 µl 0.05% (v/v) Tween in PBS, to remove unbound analytes. Next, the arrays were incubated with 200 µl 1 µg/ml streptavidin-linked Alexa-647 (SA-AL647) (Invitrogen) in 1% PBS-MT. After 1 h, the arrays were washed two times with 200 µl 0.05% Tween in PBS, and lastly covered with 200 µl PBS. The slides were dried with a stream of $N_2$ gas and scanned shortly after.

Scanning and Data Handling

The scanning was performed on a confocal microarray scanner (ScanArray Express HT, Perkin Elmer Life & Analytical Sciences). Serum arrays were scanned at PMT gain/laser: 50/70, 70/70, 80/80, 80/90 and 90/90. Urine arrays were scanned at 50/70, 70/70, 80/80 and 95/95. In both cases, scan resolution was set to 10 µm. The quantification was carried out in ScanArray Express software v 4.0 (Perkin Elmer Life & Analytical Sciences) using the fixed circle method. Circle diameter was set to 125 µm, background measurements were made between 210 and 300 µm from circle center.

The local background was subtracted and to compensate for possible local defects, the two highest and the two lowest replicates were automatically excluded and each data point represents the mean value of the remaining four replicates. Only non-saturated spots were chosen and scaled to a commonscan setting: 90/90 for serum and 95/95 for urine.

Chip-to-chip normalization of the data sets was performed, using a semi-global normalization approach, conceptually similar to the normalization developed for DNA microarrays. Thus, the coefficient of variation (CV) was first calculated for each analyte and ranked. Fifteen percent of the analytes that displayed the lowest CV values over all samples were identified, corresponding to 21 analytes, and used to calculate a chip-to-chip normalization factor. The normalization factor $N_i$ was calculated by the formula $N_i = S_i/\mu$, where $S_i$ is the sum of the signal intensities for the 21 analytes for each sample and µ is the sum of the signal intensities for the 21 analytes averaged over all samples. Each data set generated from one sample was divided with the normalization factor N.

Data Analysis

Classification of the grouped samples was carried out using a Support Vector Machine (SVM). This is a supervised learning method that creates a hyperplane that tries to separate two groups of data, in this case active and inactive SLE nephritis samples. The SMV was trained using leave-one-out cross-validation. In this iterative procedure, one sample is left out during the creation of a hyperplane, after which the classifier tries to appoint the left-out sample to the correct group. For each sample/iteration, a decision value is obtained that is based on the distance from the sample to the hyperplane. From these decision values, a Receiver Operating Characteristics (ROC) curve is created. Basically, the area under the curve (between 0 and 1) is a measurement of how well the two groups can be separated from each other. To obtain significantly differentiated analytes in serum and urine (grouped samples), Wilcoxon test was used. For the individually paired samples, paired t-tests were used. Coefficient of variation is defined as the standard deviation divided by the mean value.

Results

Figure 16A:
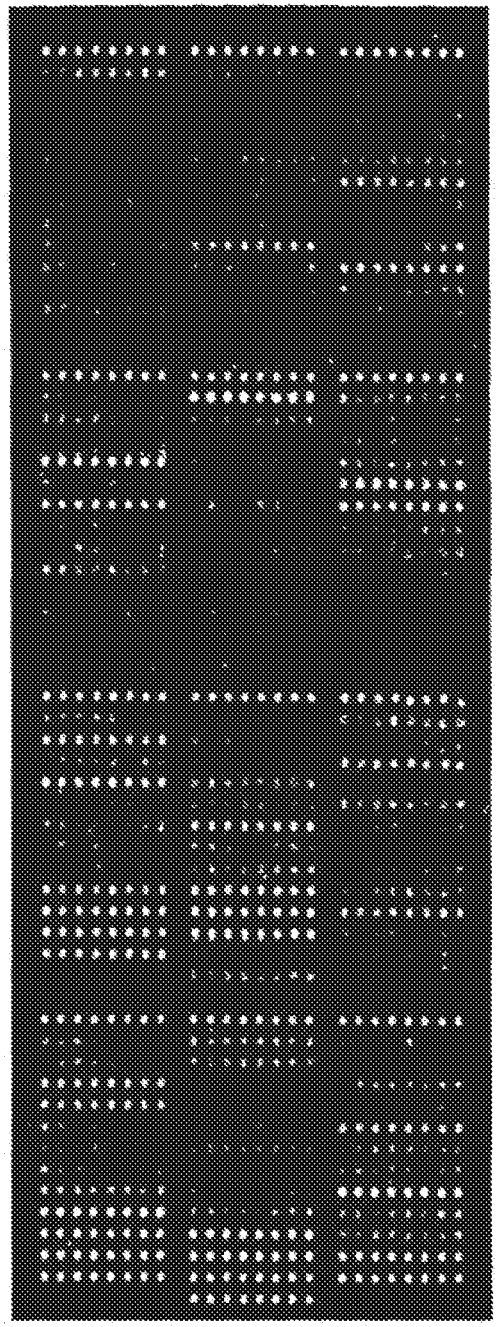
FIGS. 16A-16B depict scan images of serum flare and urine flare samples.
Figure 16B:
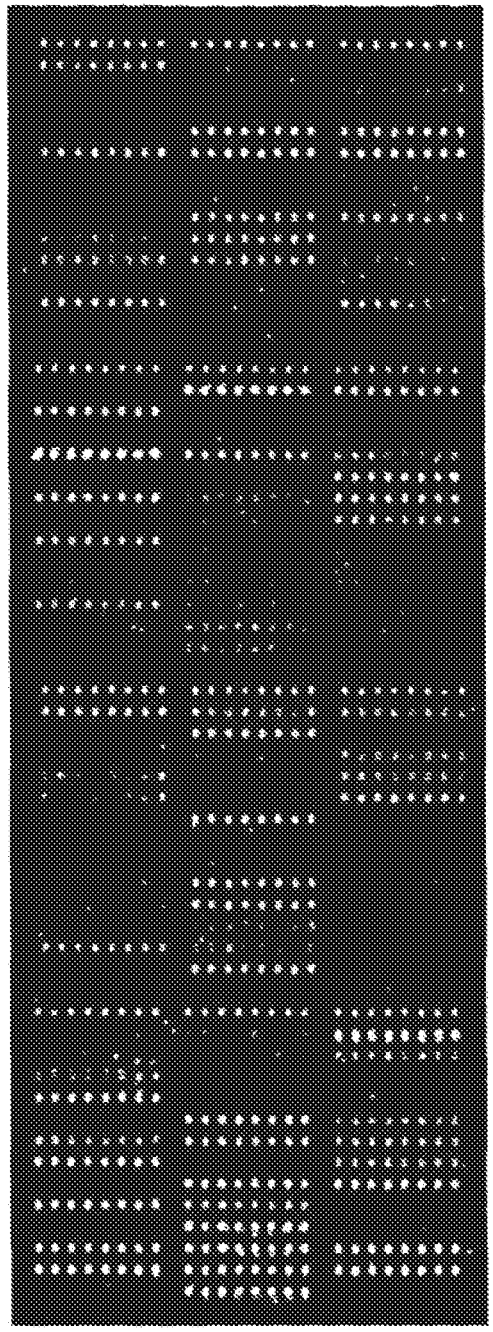

To find new biomarkers for SLE nephritis flare and investigate classification potential in terms of disease activity, we used our in-house developed recombinant antibody microarray, targeting 63 analytes with 147 scFvs, to analyze 59 and 58 matched serum and urine samples. All samples were labeled with biotin and incubated on array. Each array was scanned, quantified and finally processed and normalized. Representative scan images of both serum and urine samples are shown in FIG. 16. Notably, despite lower protein concentrations in urine than serum, equally strong signals were obtained.

To examine whether flares could be discriminated from remissions, SVM analyses were performed using data from all samples, divided in two cohorts according to activity. ROC curves and predictor plots are presented in FIG. 17 (see Table 5 for list). A moderate classification of serum samples, with a ROC area of 0.74, was established (sensitivity 76%, specificity 62%, threshold set to 0). Interestingly, urine samples were more easily classified with a ROC area of 0.87 (81% sensitivity, 76% specificity), indicating a more distinct difference in urine of patients with active versus inactive SLE nephritis. The difference between serum and urine is evident comparing the predictor plots, where urine samples are more correctly ordered.

Biomarkers of Flare Using all Samples

To identify significant biomarkers for SLE nephritis flare, quantified data from all samples were divided in two groups according to activity. The significant analytes in both serum and urine were then identified using Wilcoxon test. The result is presented in Table 5. Using $p<0.05$ for urine would yield 102 scFvs against 51 analytes, compared to serum: 31 scFvs against 23. At large, the identified biomarkers are up-regulated in both serum and urine during flare, indicating an increased inflammatory activity. Notably, only two proteins are down-regulated, both in serum: C1q and MCP-4(1).

The box-plots in FIG. 18B illustrate the distribution of intensities amongst flares and remissions, of the top three ranked analytes in serum and urine, i.e. displaying the lowest p-values.

Biomarkers of Flare Using Individually Paired Samples

Next, paired samples were compared to reduce biological variation between patients. This would either support already highlighted analytes, or discover new biomarkers that, in between patients show high variation, thereby concealing their significance. Therefore, paired t-tests were performed with paired flair/remission samples from five patients (denoted patients E, I, K, L and N). Table 6 shows the significant analytes (serum: $p<0.05$, urine: $p<0.001$). The highest ranked analytes (displaying the lowest p-values) are shown in FIG. 18B-C. Even with tougher constraints, it is clear that a high proportion of analytes differ in urine samples. This observation coincides with the obtained biomarker panels using all samples, FIG. 4.

REFERENCES

1. Schur, Peter H. Systemic Lupus Erythematosus. *Encyclopedia of Life Sciences*. 2009, pp. 1-11.
2. Liu, Chau-Ching and Ahearn, Joseph M. The search for lupus biomarkers. *Best practice & research clinical rheumatology*. 2009, Vol. 23, pp. 507-523.
3. Cordeiro, Ana C and Isenberg, David A. Novel therapies in lupus—focus on nephritis. *Acto reumatol port.* 2008, Vol. 33, pp. 157-169.
4. Cockwell, Paul and Adu, Dwomoa. Glomerulonephritis. *Encyclopedia of life sciences*. 2001, pp. 1-12.

5. Eisenberg, Robert. Why can't we find a new treatment for SLE? *Journal of autoimmunity.* 2009, Vol. 32, pp. 223-230.
6. Rovin, Brad H, et al. Biomarker discovery in human SLE nephritis. *Bulletin of the NYU hospital for joint diseases.* 2007, Vol. 65(3), pp. 187-93.
7. Yee, Chee-Seng, et al. Assessment of disease activity and quality of life in systemic lupus erythematosus—new aspects. *Best practice & research clinical rheumatology.* 2009, Vol. 23, pp. 457-467.
8. Wingren, Christer, et al. Design of recombinant antibody microarrays for complex proteome analysis: choice of sample labeling-tag and solid support. *Proteomics.* 2007, Vol. 7, pp. 3055-3065.
9. Ingvarsson, Johan, et al. Design of recombinant antibody microarrays for serum protein profiling: targeting of complement proteins. *Journal of proteome research.* 2007, Vol. 6, pp. 3527-3536.
10. Ingvarsson, Johan, et al. Detection of pancreatic cancer using antibody microarray-based serum protein profiling. *Proteomics.* 2008, Vol. 8, pp. 2211-2219.
11. Carlsson, Anders, et al. Serum proteome profiling of metastatic breast cancer using recombinant antibody microarrays. *European journal of cancer.* 2008, Vol. 44, pp. 472-480.
12. Borrebaeck, Carl A K and Wingren, Christer. Design of high-density antibody microarrays for disease proteomics: key technological issues. *Journal of proteomics.* 2009.
13. Wingren, Christer and Borrebaeck, Carl A K. Antibody-based microarrays. *Microchip methods in diagnostics.* 2009, Vol. 509, pp. 57-83.
14. Borrebaeck, Carl A K and Wingren, Christer. Transferring proteomic discoverys into clinical practice. *Expert rev. proteomics.* 2009, Vol. 6(1), pp. 11-13.
15. Schwartz, Noa, Michaelson, Jennifer S and Putterman, Chaim. Lipocalin-2, TWEAK, and other cytokines as urinary biomarkers for lupus nephritis. *Ann. N.Y. Acad. Sci.* 2007, Vol. 1109, pp. 265-274.
16. Borrebaeck, Carl A K and Wingren, Christer. High-throughput proteomics using antibody microarrays: an update. *Expert Rev. Mol. Diagn.* 2007, Vol. 7, pp. 673-686.
17. Rahman, Anisur and Isenberg, David A. Systemic lupus erythematosus-mechanisms of disease. *New england journal of medicin.* 2008, Vol. 358, pp. 929-939.
18. Klareskog, Lars, Saxne, Tore and Yvonne, Enman. *Reumatologi.* Studentlitteratur. 2005, p. 144.
19. Liu, Bi-Cheng, et al. Application of antibody array technology in the analysis of urinary cytokine profiles in patients with chronic kidney disease. *Am J Nephrol.* 2006, Vol. 26, pp. 483-490.
20. Thongboonkerd, Visith. Practical points in urinary proteomics. *Journal of proteome research.* 2007, Vol. 6, pp. 3881-3890.

The invention claimed is:

1. A method diagnosing and treating Systemic Lupus Erythematosus in a subject comprising the steps of:
   a) providing a blood or serum sample to be tested;
   b) measuring the presence and/or amount in the test sample of the proteins Glucagon-like peptide-1 (GLP-1) and Procathepsin-W using an array;
   c) diagnosing Systemic Lupus Erythematosus based on the presence and/or amount of GLP-1 and Procathepsin-W in the test sample, wherein the presence and/or amount in the test sample of GLP-1 and Procathepsin is indicative of a Systemic Lupus Erythematosus; and
   d) treating a subject diagnosed in step (c) as having Systemic Lupus Erythematosus with a therapeutic agent selected from the group consisting of immunosuppressant agents and antimalarial agents.

2. The method according to claim 1 further comprising the steps of:
   e) providing a control sample from an individual with a different Systemic Lupus Erythematosus-associated disease state to the test subject; and
   f) measuring the presence and/or amount in the control sample of the GLP-1 and Procathepsin-W measured in step (b);
   wherein the Systemic Lupus Erythematosus-associated disease state is identified in the event that the presence and/or amount in the test sample of the GLP-1 and Procathepsin-W measured in step (b) is different from the presence and/or amount in the control sample.

3. The method according to claim 2, wherein the control sample of step (c) is provided from a healthy individual or an individual with Systemic Lupus Erythematosus.

4. The method according to claim 2 wherein step (b) and/or step (d) is performed using a first binding agent capable of binding to GLP-1 and Procathepsin-W.

5. The method according to claim 4 wherein the first binding agent is an antibody or a fragment thereof.

6. The method according to claim 5 wherein the antibody or fragment thereof is selected from the group consisting of: scFv; Fab; and a binding domain of an immunoglobulin molecule.

7. The method according to claim 1 wherein step (b) comprises measuring the presence and/or amount in the test sample of all of the biomarkers from the group consisting of Glucagon-like peptide-1 (GLP-1), Procathepsin W, Angiomotin, C1 esterase inhibitor, C1q, C1s, C3, C4, C5, CD40, Eotaxin, Complement factor B (Factor B), IgM, IL-10, IL-11, IL-12, IL-13, IL-16, IL-18, IL-1α, IL-1-ra, IL-2, IL-3, IL-4, IL-5, IL-6, IFN-γ, Integrin alfa-10 (Integrin α-10), LDL, Leptin, Lewis x/CD15, Monocyte chemotactic protein-1 (MCP-1), Mucine 1, RANTES, Sialo Lewis x, TGF-β, Tumor necrosis factor-alfa (TNF-α), VEGF, IFN-α, Monocyte chemotactic protein-4 (MCP-4), Properdin, GM-CSF, IL-7, Integrin alfa-11 (Integrin α-11), TM peptide, Tumor necrosis factor beta (TNF-β), Tyrosine protein kinase JAK3, Tyrosine protein kinase BTK, IL-8, IL-1β, Monocyte chemotactic protein-3 (MCP-3), IL-9, Glucagon-like peptide-1 receptor (GLP-1 R), CD40 ligand (CD40-L), Lewis y, HLA-DR, ICAM-1, and Ku 70/80.

8. The method according to claim 1 wherein step (b) is performed using an assay comprising a second binding agent capable of binding to GLP-1 and Procathepsin-W proteins, the second binding agent having a detectable moiety.

9. The method according to claim 8 wherein the second binding agent is an antibody or a fragment thereof.

* * * * *